(12) United States Patent
Chiorini et al.

(10) Patent No.: US 8,685,722 B2
(45) Date of Patent: Apr. 1, 2014

(54) BOVINE ADENO-ASSOCIATED VIRAL (BAAV) VECTOR AND USES THEREOF

(75) Inventors: John A. Chiorini, Dayton, MD (US); Michael Schmidt, Kensington, MD (US); Ioannis Bossis, Columbia, MD (US); Giovanni Di Pasquale, Kensington, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/413,321

(22) Filed: Mar. 6, 2012

(65) Prior Publication Data

US 2012/0253018 A1 Oct. 4, 2012

Related U.S. Application Data

(62) Division of application No. 10/581,228, filed as application No. PCT/US2004/040825 on Dec. 6, 2004, now Pat. No. 8,137,960.

(60) Provisional application No. 60/526,786, filed on Dec. 4, 2003, provisional application No. 60/607,854, filed on Sep. 8, 2004.

(51) Int. Cl.
*C12N 15/86* (2006.01)

(52) U.S. Cl.
USPC ...................................... 435/320.1

(58) Field of Classification Search
None
See application file for complete search history.

(56) References Cited

U.S. PATENT DOCUMENTS

| | | | |
|---|---|---|---|
| 6,146,874 A | 11/2000 | Zolotukhin et al. | |
| 6,180,613 B1 | 1/2001 | Kaplitt et al. | |
| 6,221,349 B1 | 4/2001 | Couto et al. | |
| 6,309,634 B1 | 10/2001 | Bankiewicz et al. | |
| 6,391,858 B2 | 5/2002 | Podsakoff et al. | |
| 6,468,524 B1 | 10/2002 | Chiorini et al. | |
| 6,485,976 B1 | 11/2002 | Nadler et al. | |
| 6,855,314 B1 | 2/2005 | Chiorini et al. | |
| 6,984,517 B1 | 1/2006 | Chiorini et al. | |
| 7,056,502 B2 | 6/2006 | Hildinger et al. | |
| 7,259,151 B2 | 8/2007 | Arbetman et al. | |
| 2002/0076754 A1 | 6/2002 | Sun et al. | |
| 2003/0228282 A1 | 12/2003 | Gao et al. | |
| 2004/0086490 A1 | 5/2004 | Chiorini et al. | |
| 2004/0110266 A1 | 6/2004 | Chiorini et al. | |
| 2004/0115789 A1 | 6/2004 | Meruelo et al. | |
| 2005/0255089 A1 | 11/2005 | Chiorini et al. | |
| 2012/0253018 A1* | 10/2012 | Chiorini et al. ............ | 530/387.9 |

FOREIGN PATENT DOCUMENTS

| | | |
|---|---|---|
| DE | 44 36 664 A1 | 7/1996 |
| EP | 1 310 571 | 5/2003 |
| WO | WO 93/24641 | 12/1993 |
| WO | WO 95/11997 | 5/1995 |
| WO | WO 96/00587 A | 1/1996 |
| WO | WO 96/15777 A | 5/1996 |
| WO | WO 96/18727 | 6/1996 |
| WO | WO 97/06272 | 2/1997 |
| WO | WO 98/11244 | 3/1998 |
| WO | WO 98/41240 A | 9/1998 |
| WO | WO 98/45462 A | 10/1998 |
| WO | WO 99/61601 | 12/1999 |
| WO | WO 99/61601 A2 | 12/1999 |
| WO | WO 00/26254 | 5/2000 |
| WO | WO 00/28061 | 5/2000 |
| WO | WO 01/70276 | 9/2001 |
| WO | WO 01/83692 | 11/2001 |
| WO | WO 03/093479 | 11/2003 |
| WO | WO 2004/112727 | 12/2004 |
| WO | WO 2005/017101 | 2/2005 |
| WO | WO 2006/029196 | 3/2006 |
| WO | WO 2006/119432 | 11/2006 |

OTHER PUBLICATIONS

Schmidt et al., "Cloning and characterization of a bovine adeno-associated virus", Journal of Virology, Vo. 78, No. 12, Jun. 2004, pp. 6509-6516.
Chiorini et al. "Cloning and Characterization of AAV5", Journal of Virology, The American Society for Microbiology, vol. 73, No. 2, Feb. 1999, pp. 1309-1319.
Chiorini et al. "Cloning of adeno-sssociated virus type 4 (AAV4) and generation of recombinant AAV4 particleS" Journal of Virology, The American Society for Microbiology, vol. 71, No. 9, Sep. 1997, pp. 6823-6833.
Pasquale et al., "A novel bovine virus efficiently transduces inner ear neuroepithelial cells", Molecular Therapy, Academic Press, vol. 11, No. 6, Jun. 2005, pp. 849-855.
Hisako et al., "Identification of adeno-associated virus contamination in cell and virus stocks by PCR", Biotechniques, Apr. 2004, vol. 36, No. 4, Apr. 2004, pp. 676-680.
Coria et al., "Isolation and identification of bovine adenovirus type 3 with an adenovirus associated virus", American Journal of Veterinary Research, vol. 39, No. 12, 1978, pp. 1904-1906.
Alexander et al., "DNA-Damaging Agents Greatly Increase the Transduction of Nondividing Cells by Adeno-Associated Virus Vectors," Dec. 1994, *J. Virol.*, 68(12):8282-8287.
Alisky et al., "Transduction of Murine Cerebellar Neurons with Recombinant FIV and AAV5 Vectors," Aug. 2000, *Mol. Neurosci.*, 11(1221):2669-2673.
Alisky J.M. and Tolbert D.M., "Differential labeling of converging afferent pathways using biotinylated dextran amine and cholera toxin subunit B," 1994, *Journal of Neuroscience Methods*, 52:143-148.
Allen, J.M., Halbert, C.L. and Miller, A.D., "Improved adeno-associated virus vector production with transfection of a single helper adenovirus gene, E4orf6," 2000, *Mol Ther*, 1:88-95.

(Continued)

*Primary Examiner* — Michael Burkhart
(74) *Attorney, Agent, or Firm* — Sheridan Ross P.C.

(57) ABSTRACT

The present invention provides a bovine adeno-associated virus (BAAV) virus and vectors and particles derived therefrom. In addition, the present invention provides methods of delivering a nucleic acid to a cell using the BAAV vectors and particles.

2 Claims, 43 Drawing Sheets

(56) References Cited

OTHER PUBLICATIONS

Arnberg, N., A. H. Kidd, K. Edlund, J. Nilsson, P. Pring-Akerblom, and G. Wadell, "Adenovirus type 37 binds to cell surface sialic acid through a charge-dependent interaction," 2002, *Virology*, 302:33-43.
Atchison, R. W., B. C. Castro, and W. M. Hammon, "Adenovirus-Associated Defective Virus Particles,"1965, *Science*, 149:754-756.
Aurcchio et a "A Single-Step Affinity Column for Purification of Stereotype-5 Based Adeno-Associated Viral Vectors," Oct. 2001, *Mol Ther*, 4(4):372-374.
Bachmann, P.A., M.D. Hoggan, E. Kurstak, J.L. Melnick, H.G. Pereira, P. Tattersall, and C. Vago, "Parvoviridae: second report,"1979, *Interverology*, 11:248-254.
Bajocchi G, Feldman SH, Crystal RG, Mastrangeli A., "Direct in vivo gene transfer to ependymal cells in the central nervous system using recombinant adenovirus vectors," 1993, *Nat Genet*, 3:229-234.
Bantel-Schaal U, Delius H, Schmidt R. zur Hausen H., "Human adeno-associated virus type 5 is only distantly related to other known primate helper-dependent parvoviruses," 1999, *J Virol.*, 73(2):939-947.
Bantel-Schaal U, zur Hausen H., "Characterization of the DNA of a defective human parvovirus isolated from a genital site," 1984, *Virology*, 134(1):52-63, XP009028974.
Bantel-Schaal, U. and M. Stohr, "Influence of adeno-associated virus on adherence and growth properties of normal cells," 1992, *J. Virol.*, 66:773-779.
Bantel-Schaal, U., Hub, B. and Kartenbeck, J., "Endocytosis of adeno-associated virus typo 5 leads to accumulation of virus particles in the Golgi compartment," 2002, *J Virol*, 76:2340-2349.
Bartlett JS, Kleinschmidt J., Boucher RC, and Samulski RJ, "Targeted adeno-associated virus vector transduction of nonpermissive cells mediated by a bispecific F(ab'gamma)$_2$ antibody," 1999, *Nat Biotechnol*, 17:181-186.
Bartlett JS, Samulski RJ, McCown TJ., "Selective and rapid uptake of adeno-associated virus type 2 in brain," 1998, *Hum Gene Ther*, 9(8):1181-1186.
Bartet J.S., Wlcher R. and Samulsk, R.J., "Infectious entry pathway of adeno-associated virus and adeno-associated virus vectors," 2000, *J Virol*, 74:2777-2785.
Ben-Israel, H. and Kleinberger, T., "Adenovirus and cell cycle control," 2002, *Front Biosci*, 7:d1369-1395.
Chiorini JA, Afione S, Kotin RM, "Adeno-associated virus (AAV) type 5 Rep protein cleaves a unique terminal resolution site compared with other AAV serotypes," 1999a May, *J Virol.*, 73(5):4293-4298.
Chiorini, J.A., C.M. Wendtner, E. Urcelay, B. Safer, M. Hallek, and R.M. Kotin, "High-efficiency transfer of the T cell co-stimulatory molecule B7-2 to lymphoid cells using high-titer recombinant adeno-associated virus vectors,"1995, *Human Gene Therapy*, 6:1531-1541.
Chiorini, J.A., L. Yang, B. Safer, and R.M. Kotin, "Determination of adeno-associated virus Rep68 and Rep78 binding sites by random sequence oligonucleotide selection," 1995, *J. Virol.*, 69:7334-7338.
Chiorini, J.A., M.D. Weitzman, R.A. Owens, E. Urcelay, B. Safer, and R.M. Kotin, "Biologically active Rep. proteins of adeno-associated virus type 2 produced as fusion proteins in *Escherichia coli*," 1994a, *J. Virol.*, 68:797-804.
Chiorini, J.A., S.M. Wiener, R.M. Kotin, R.A. Owens, SRM Kyöstiö, and B. Safer, "Sequence requirements for stable binding and function of Rep68 on the adeno-associated virus type 2 inverted terminal repeats,"1994b, *J. Virol.*, 68:7448-7457.
Clark et al., "Highly Purified Recombinant Adeno-Associated Virus Vectors are Biologically Active and Free of Detectable Helper and Wild-Type Viruses," 1999, *Hum. Gene Ther.*, 10:1031-1039.
Cohen-Salmon et al., "Targeted ablation of connexin26 in the inner ear epithelial gap junction network causes hearing impairment and cell death," 2002, *Curr Biol*, 12:1106-1111.
Crystal RG, "Transfer of genes to humans: early lessons and obstacles to success," 1995, *Science*, 270(5235):404-410.
Database EMBL, Entry GGACTAA, GenBank Accession No. M61166, Mar. 27, 1991, XP002125220.
Davidson BL, Doran SE, Shewach DS, Latta JM, Hartman JW, Roessler BJ., "Expression of *Escherichia coil beta*-galactosidase and rat HPRT in the CNS of *Macaca mulatta* following adenoviral mediated gene transfer,"1994, *Exp Neuroi*, 125:258-267.
Davidson BL, Stein CS, Heth JA, Martins I, Kotin RM, Derksen TA, Zabner J, Ghodsi A, Chiorini JA, "Recombinant adeno-associated virus type 2, 4, and 5 vectors: Transduction of variant cell types and regions in the mammalian central nervous system," 2000, *Proc Natl Acad Sci U S A.*, 97(7):3428-3432.
Deonarain MP, "Ligand-targeted receptor-mediated vectors for gene delivery," 1998, *Molecular Conjugate Vectors*, 8(1):53-69.
Derby, M. L., M. Sena-Esteves, et al., "Gene transfer into the mammalian inner ear using HSV-1 and vaccinia virus vectors," 1999, *Hear Res*, 134(1-2):1-8,.
Di Pasquale, G., and J. A. Chiorini, "PKA/PrKX activity is a modulator of AAV/adenovirus interaction," 2003, *EMBO J*, 22:1716-1724.
Di Pasquale, G., B. L. Davidson, et al., "Identification of PDGFR as a receptor for AAV-5 transduction," 2003, *Nat Med*, 9(10):1306-1312.
Dixit, M., M.S. Webb, W.C. Smart, and S. Ohi, "Construction and expression of a recombinant adeno-associated virus that harbors a human *beta*-globin-encoding cDNA," 1991, *Gene*, 104:253-257.
Doll RF, Crandall JE, Dyer CA, Aucoin JM, Smith FL., "Comparison of promoter strengths on gene delivery into mammalian brain cells using AAV vectors," 1996, *Gene Ther*, 3:437-447.
Duan, D., Yue Y., Yan Z., McCray PBJr, and Engelhardt JF., "Polarity influences the efficiency of recombinant adenoassociated virus infection in differentiated airway epithelia," 1998, *Hum Gene Ther*, 9:2761-2776.
During MJ, Symes CW, Lawlor PA, Lin J, Dunning J, Fitzsimons HL, Poulsen D, Leone P, Xu R, Dicker BL, Lipski J, Young D, "An oral vaccine against NMDAR1 with efficacy in experimental stroke and epilepsy," 2000, *Science*, 287:1453-1460.
During MJ, Xu R, Young D, Kaplitt MG, Sherwin RS, Leone P., "Peroral gene therapy of lactose intolerance using an adeno-associated virus vector," 1998, *Nat Med*, 4(10):1131-1135.
During MJ, Leone P, "Adeno-associated virus vectors for gene therapy of neurodegenerative disorders," ' 1995-96, *Clin Neurosci*, 3(5):292-300, XP-002125034.
Erles, K., Sebokova, P. and Schlehofer, J.R., "Update on the prevalence of serum antibodies (IgG and IgM) to adeno-associated virus (AAV)," 1999, *J Med Virol*, 59:406-411.
Fan D-S, Ogawa M, Fujimoto K-I, Ikeguchi K, Ogasawara Y, Urabe M, Nishizawa M, Nakano I, Yoshida M, Nagatsu I, Ichinose H, Nagatsu T, Kurtzman GJ, Ozawa K, "Behavioral recovery in 6-hydroxydopamine-lesioned rats by cotransduction of striatum with tyrosine hydroxylase and aromatic L-amino acid decarboxylase genes using two separate adeno-associated virus vectors," 1998, *Hum Gene Ther*, 9:2527-2535.
Fisher, KJ, Jooss K., Alston J., Yang Y., Haecker SE, High K., Pathak R., Raper SE, and Wilson JM, "Recombinant adeno-associated virus for muscle directed gene therapy,":1997, *Nat Med*, 3:306-312.
Fisher, R.E., H.D. Mayor, "The evolution of defective and autonomous parvoviruses," 1991, *J Theor Biol*, 149:429-439.
Flannery et al., "Efficient Photoreceptor-targeted Gene Expression in vivo by Recombinant Adeno-Associated Virus," 1997, *Proc Nati Acad Sci USA*, 94:6916-6921.
Flotte TR, Solow R, Owens RA, Afione S, Zeitlin PL, Carter BJ, "Gene expression from adeno-associated virus vectors in airway epithelial cells," 1992, *Am J Respir Cell Mol Biol*, 7(3):349-356; XP000609213.
Flotte, T.R., S.A. Afione, C. Conrad, S.A. McGrath, R. Solow, H. Oka, P.L. Zeitlin, W.B. Guggino, and B.J. Carter, "Stable in vivo expression of the cystic fibrosis transmembrane conductance regulator with an adeno-associated virus vector," 1993, *Proc. Natl. Acad. Sci.*, 90:10613-10617.
Flotte, T.R., S.A. Afione, R. Solow, M.L. Drumm, D. Markakis, W.B. Guggino, P.L. Zeitlin, and B.J. Carter, "Expression of the cystic fibrosis transmembrane conductance regulator from a novel adeno-associated virus promoter," 1993, *J Biol Chem*, 268:3781-3790.
Frolenkov GI, Belyantseva IA, Friedman TB, Griffith AJ, "Genetic insights into the morphogenesis of inner ear hair cells," 2004, *Nat Rev Genet*, 5:489-498.

(56) References Cited

OTHER PUBLICATIONS

Gao, G., L. H. Vandenberghe, M. R. Alvira, Y. Lu, R. Calcedo, X. Zhou, and J. M. Wilson, "Clades of Adeno-associated viruses are widely disseminated in human tissues," 2004, *J Virol*, 78:6381-6388.
Gao, G.P., Alvira, M.R., Wang, L., Calcedo, R., Johnston, J. and Wilson, J.M., "Novel adeno-associated viruses from rhesus monkeys as vectors for human gene therapy," 2002, *Proc Natl Acad Sci USA*, 99:11854-11859.
GenBank Accession No. AY186198.
Georg-Fries B, Biederlack S, Wolf J, zur Hausen H, "Analysis of proteins, helper dependence, and seroepidemiology of a new human parvovirus," 1984, *Virology*, 134(1):64-71, XP002027460.
Ghodsi A., Stein C., Derksen T., Martins I., Anderson RD, & Davidson BL, "Systemic hyperosmolality improves beta-glucuronidase distribution and pathology in murine MPS VII brain following intraventricular gene transfer," 1999, *Exp Neurol*, 160:109-116.
Ghodsi A., Stein, C., Derksen T., Yang, G., Anderson R.D., Davidson B.L., "Extensive beta-glucuronidase activity in murine central nervous system after adenovirus-mediated gene transfer to brain,"1998, *Hum Gene Ther*, 9:2331-2340.
Girod A., Ried M., Wobus C., Lahm H., Leike K., Kleinschmidt J., Deleage G., and Hallek M., "Genetic capsid modifications allow efficient re-targeting of adeno-associated virus type 2," 1999, *Nat Med*, 5:1052-1056.
Grimm, D. and M. A. Kay, "From virus evolution to vector revolution: use of naturally occurring serotypes of adeno-associated virus (AAV) as novel vectors for human gene therapy," 2003, *Curr Gene Ther*, 3(4)::281-304.
Grimm D and Kern A, Rittner K Kleinschmidt JA, "Novel Tools for Production and Purification of Recombinant Adenoassociated Virus Vectors," 1998, *Human Gene Therapy*, 9:2745-2760.
Guy J., Qi X., Muzyczka N., and Hauswirth WW, "Reporter expression persists 1 year after adeno-associated virus-mediated gene transfer to the optic nerve," 1999, *Arch Ophthalmol*, 117:929-937.
Halbert CL, Standaert TA, Aitken ML, Alexander IE, Russell DW, and Miller AD, "Transduction by adeno-associated virus vectors in the rabbit airway: efficiency, persistence, and readministration," 1997, *J.Virol.*, 71:5932-5941.
Halbert, C. L., J. M. Allen, and A. D. Miller, "Adeno-associated virus type 6 (AAV6) vectors mediate efficient transduction of airway epithelial cells in mouse lungs compared to that of AAV2 vectors," 2001, *J Virol*, 75:6615-6624.
He, D. Z., J. Zheng, et al., "Development of acetylcholine receptors in cultured outer hair cells," 2001, *Hear Res*, 162(1-2):113-125.
Hehir K.M., Armentano D., Cardoza L.M., Choquette T.L., Berthelette P.B., White G.A., Couture L.A., Everton M.B., Keegan J., Martin J.M., Pratt D.A., Smith M.P., Smith A.E., Wadsworth S.C., "Molecular characterization of replication-competent variants of adenovirus vectors and genome modifications to prevent their occurrence," 1996, *J Virol*, 70(12):8459-8467.
Heister, T., Heid, I. Ackermann, M., Fraefel, C., "Herpes simplex virus type 1/adeno-associated virus hybrid vectors mediate site-specific integration at the adeno-associated virus preintegration site, AAVS1, on human chromosome 19," 2002, *J Virol*, 76(14):7163-7173.
Hermonat PL, Santin AD, De Greve J, De Rijcke M, Bishop BM, Han L, Mane M, Kokorina N, "Chromosomal latency and expression at map unit 96 of a wild-type plus adeno-associated virus (AAV)/Neo vector and identification of p81, a new AAV transcriptional promoter," Nov.-Dec. 1999, *J Hum Virol*, 2(6):359-368.
Hermonat, PL and N Muzyczka, "Use of adeno-associated virus as a mammalian DNA cloning vector: transduction of neomycin resistance into mammalian tissue culture cells," 1984, *Proc Nati Acad Sci USA*, 81:6466-6470.
Hermonat, P,L., M.A. Labow, R. Wright, K.. Berns, and N. Muzyczka, "Genetics of adeno-associated virus: isolation and preliminary characterization of adeno-associated virus type 2 mutants," 1984, *J. Virol.*, 51:329-339.
Hoggan, M. D., N. R. Blacklow, and W. P. Rowe, "Studies of small Dna viruses found in various adenovirus preparations: physical, biological, and immunological characteristics," 1966, *Proc Natl Aced Sci USA*, 55:1467-1474.
Hoggan, M.D., "Adenovirus associated viruses," 1970, *Prog Med Virol*, 12:211-239.
Holt, J. R., "Viral-mediated gene transfer to study the molecular physiology of the Mammalian inner ear" 2002, *Audiol Neurootol*, 7(3):157-160.
Holt, J. R., D. C. Johns, et al., "Functional expression of exogenous proteins in mammalian sensory hair cells infected with adenoviral vectors," 1999, *J Neurophysiol*, 81(4):1881-1888.
Hsueh Y-P, Sheng M., "Regulated expression and subcellular localization of syndecan heparan sulfate proteoglycans and the syndecan-binding protein CASK/LIN-2 during rat brain development," 1999, *J Neurosci*, 19(17):7415-7425.
Hsueh Y-P, Yang F-C, Kharazia V, Naisbitt S, Cohen AR, Weinberg RJ, Sheng M, "Direct interaction of CASK/LIN-2 and syndecan heparan sulfate proteoglycan and their overlapping distribution in neuronal synapses," 1998, *J Cell Biol*, 142(1):139-151.
Hull, R. N., J. R. Minner, and J. W. Smith, "New viral agents recovered from tissue cultures of monkey kidney cells. I. Origin and properties of cytopathogenic agents S.V.1, S.V.2, S.V.4, S.V.5, S.V.6, S.V.11, S.V.12 and S.V.15," 1956, *Am J Hyg*, 63:204-215.
Hull, R. N., and J. R. Minner, "New viral agents recovered from tissue cultures of monkey kidney cells. II. Problems of isolation and identification," 1957, *Ann NY Acad Sci*, 67:413-423.
Hull, R. N., J. R. Minner, and C. C. Mascoli, "New viral agents recovered from tissue cultures of monkey kidney cells. III. Recovery of additional agents both from cultures of monkey tissues and directly from tissues and excreta," 1958, *Am J Hyg*, 68:31-44.
Hunter, L.A. and R.J. Samulski, "Colocalization of adeno-associated virus Rep and capsid proteins in the nuclei of infected cells," 1992, *J. Virol.*, 66:317-324.
Im DS, Muzyczka N, "Partial purification of adeno-associated virus Rep78, Rep52, and Rep40 and their biochemical characterization," Feb. 1992, *J Virol.*, 66(2):1119-1128, XP002125031.
Inglis VI, Jones MP, Tse AD, Easton AS, "Neutrophils both reduce and increase permeability in a cell culture model of the blood-brain barrier," 2004, *Brain Res*, 998(2):218-229.
Ito, M. and H.D. Mayor, "Hemagglutinin of type 4 adeno-associated satellite virus," 1968, *J. Immunol*, 100:61-68.
Jaksch, M., K.D. Gerbitz, and C. Kilger, "Screening for mitochondrial DNA (mtDNA) point mutations using nonradioactive single strand conformation polymorphism (SSCP) analysis," 1995, *Clin. Biochem.*, 28:503-509.
Janik, J.E., M.M. Huston, K. Cho, and J.A. Rose, "Efficient syntheses of adeno-associated virus structural proteins requires both adenovirus DNA binding protein and VA I RNA," 1989, *Virology*, 168:320-329.
Jero J, Mhatre AN, Tseng CJ, Stern RE, Coling DE, Goldstein JA, Hong K, Zheng WW, Hogue AT, Lalwani AK., "Cochlear gene delivery through an intact round window membrane in mouse," 2001, *Hum Gene Ther*, 12(5):539-548.
Johansson CB, Momma S, Clarke DL, Risling M, Lendahl U, Frisen J, "Identification of a neural stem cell in the adult mammalian central nervous system," 1999, *Cell*, 96(1):25-34.
Kaludov et al., "Adeno-Associated Virus Serotype 4 (AAV4) and AAV5 Both Require Sialic Acid Binding for Hemagglutination and Efficient Transduction but Differ in Sialic Acid Linkage Specificity" 2001, *J. Virol.*, 75(15):6884-6893.
Kaludov et al., "Scalable Purification of Adeno-Associated Virus Type 2, 4 or 5 Using Ion-Exchange Chromatography," 2002, *Human Gene Therapy*, 13:1235-1243.
Kanzaki, S., K. Ogawa, et al., "Transgene expression in neonatal mouse inner ear explants mediated by first and advanced generation adenovirus vectors," 2002, *Hear Res*, 169(1-2):112-120.
Kaplitt, M.G., P. Leone, R.J. Samulski, X. Xiao, D.W. Pfaff, K.L. O'Malley, and J.M. During, "Long-term gene expression and phenotypic correction using adeno-associated virus vectors in the mammalian brain," 1994, *Nature Genetics*, 8:148-154.

(56) References Cited

OTHER PUBLICATIONS

Kelsell, D.P., Dunlop, J., Stevens, H.P., Lench, n. J., Liang, J.N., Parry, G., Mueller, R.F., Leigh, I.M., "Connexin 26 mutations in hereditary non-syndromic sensorineural deafness," 1997, *Nature*, 387(6628):80-83.

Kern, A., K. Schmidt, C. Leder, O. J. Muller, C. E. Wobus, K. Bettinger, C. W. Von der Lieth, J. A. King, and J. A. Kleinschmidt, "Identification of a heparin-binding motif on adeno-associated virus type 2 capsids," 2003, *J Virol*, 77:11072-11081.

Klein RL, Meyer EM, Peel AL, Zolotukhin S, Meyers C, Muzyczka N, King MA., "Neuron-specific transduction in the rat septohippocampal or nigrostriatal pathway by recombinant adeno-associated virus vectors," 1998, *Exp Neurol*, 150:183-194.

Kondo M., Finkbeiner WE, and Widdicombe JH., "Simple technique for culture of highly differentiated cells from dog tracheal epithelium," 1991, *Am.J.Physiol*, 261:L106-L117.

Kotin et al., "Organization of adeno-associated virus DNA in latently infected Detroit 6 cells," 1989, *Virology*, 170(2):460-467.

Kotin, R.M., M. Siniscalco, R.J. Samulski, X. Zhu, L. Hunter, C.A. Laughlin, S. McLaughlin, N. Muzyczka, M. Rocchi, and K.I. Berns, "Site-specific integration by adeno-associated virus," 1990, *Proc. Natl. Acad. Sci. USA*, 87:2211-2215.

Kovacs P, Pinter M, Csaba G, "Effect of glucosphingolipid synthesis inhibitor (PPMP and PDMP) treatment on *Tetrahymena pyriformis*: data on the evolution of the signaling system," 2000, *Cell Biochem Funct*, 18(4):269-280.

Kyo S, Nakamura M, Kiyono T, Maida Y, Kanaya T, Tanaka M, Yatabe N, Inoue M, "Successful immortalization of endometrial glandular cells with normal structural and functional characteristics," 2003, *Am J Pathol*, 163(6):2259-2269.

Kyostlo SR, Owens RA, Weitzman MD, Antoni BA, Chejanovsky N, Carter BJ, "Analysis of adeno-associated virus (AAV) wild-type and mutant Rep proteins for their abilities to negatively regulate AAV $p_5$ and $p_{19}$ mRNA levels," 1994, *J Virol*, 68(5):2947-2957, Xp-002125032.

Laughlin, C.A., M.W. Myers, D.L. Risin, B.J. Carter, "Defective-interfering particles of the human parvovirus adeno-associated virus," 1979, *Virology*, 94:162-174.

Laughlin, C.A., N. Jones, and B.J. Carter, "Effect of deletions in adenovirus early region 1 genes upon replication of adeno-associated virus," 1982, *J. Virol*, 41:868-876.

Lee K, Kim YG, Jo EC, "Shuttle PCR-based cloning of the infectious adeno-associated virus type 5 genome," 2003, *J Virol Methods*, 111(2):75-84.

Li J, Samulski RJ, Xiao X, "Role for Highly Regulated *rep* Gene Expression in Adeno-Associated Virus Vector Production," 1997, *J Virol*, 71(7):5236-5243.

Li Duan, M., T. Bordet, et al., "Adenoviral and adeno-associated viral vector mediated gene transfer in the guinea pig cochlea," 2002, *Neuroreport*, 13(10):1295-1299.

Liang Y, Annan RS, Carr SA, Popp S, Mevissen M, Margolis RK, Margolis RU., "Mammalian homologues of the *Drosophila* slit protein are ligands of the heparan sulfate proteoglycan glypican-1 in brain," 1999, *J Biol Chem*, 274(25):17885-17892.

Lo WD, Qu G, Sferra TJ, Clark R, Chen R, Johnson PR., "Adeno-associated virus-mediated gene transfer to the brain: duration and modulation of expression," 1999, *Hum Gene Ther*, 10:201-213.

Luchsinger, E., Strobbe, R., Dekegel, D. and Wellemans, G., "Use of B-IV zonal rotor centrifugation as a simple tool for the separation of adeno-associated X 7 virus (AAVX 7) from helper adenoviruses," 1971, *Arch Gesamte Virusforsch*, 33:251-258.

Luchsinger, E., Strobbe, R., Wellemans, G., Dekegel, D. and Sprecher-Goldberger, S., "Haemagglutinating adeno-associated virus (AAV) in association with bovine adenovirus type 1," 1970, *Brief report. Arch Gesamte Virusforsch*, 31:390-392.

Luebke, A. E., J, D. Steiger, et al., "A modified adenovirus can transfect cochlear hair cells in vivo without compromising cochlear function," 2001, *Gene Ther*, 8(10):789-794.

Luebke, A. E., P. K. Foster, et al., "Cochlear function and transgene expression in the guinea pig cochlea, using adenovirus- and adeno-associated virus-directed gene transfer," 2001, *Hum Gene Ther*, 12:773-781.

Maeda Y, Ikeda U, Ogasawara Y, Urabe M, Takizawa T, Saito T, Colosi P, Kurtzman G, Shimada K, Ozawa K, "Gene transfer into vascular cells using adeno-associated virus (AAV) vectors," 1997, *Cardiovasc Res*, 35(3):514-521, XP-002125030.

Mandel RJ, Rendahl KG, Spratt SK, Snyder RO, Cohen LK, Leff SE., "Characterization of intrastriatal recombinant adeno-associated virus-mediated gene transfer of human tyrosine hydroxylase and human GTP-cyclohydrolase I in a rat model of Parkinson's disease," 1998, *J Neurosci*, 18(11):4271-4284.

McCarty, D.M., J. Pereira, I. Zolotukhin, X. Zhou, J.H. Ryan, and N. Muzyczka, "Identification of linear DNA sequences that specifically bind the adeno-associated virus Rep protein," 1994, *J. Virol.*, 68:4988-4997.

McCown TJ, Xiao X, Li J, Breese Gr, Samulski RJ, "Differential and Persistent Expression Patterns of CNS Gene Transfer by an Adeno-Associated Virus (AAV) Vector," 1996, *Brain Res*, 713:99-107.

McPherson, R. A., L. J. Rosenthal, and J. A. Rose, "Human cytomegalovirus completely helps adeno-associated virus replication," 1985, *Virology*, 147:217-222.

Mendelson, E., J.P. Trempe, and B.J. Carter "Identification of the trans-acting Rep proteins of adeno-associated virus by antibodies to a synthetic oligopeptide," 1986, *J. Virol.*, 60:823-832.

Meyers, C., Mane, M., Kokorina, N., Alam, S. And Hermonat, P:L., "Ubiquitous human adeno-associated virus type 2 autonomously replicates in differentiating keratinocytes of a normal skin model," 2000, *Virology*, 272:338-346.

Mitrani E, Ziv T, Thomsen G, Shimoni Y, Melton DA, Bril A, "Activin can induce the formation of axial structures and is expressed in the hypoblast of the chick," 1990, *Cell*, 63(3):495-501.

Mizukami, H., N.S. Young, and K.E. Brown, "Adeno-associated virus type 2 binds to a 150-kilodalton cell membrane glycoprotein," 1996, *Virology*, 217:124-130.

Mori, S., L. Wang, T. Takeuchi, and T. Kanda, "Two novel adeno-associated viruses from cynomolgus monkey: pseudotyping characterization of capsid protein," 2004, *Virology*, 330:375-383.

Mouw, M.B. and Pintel, D.J., "Adeno-associated virus RNAs appear in a temporal order and their splicing is stimulated during coinfection with adenovirus," 2000, *J Virol*, 74:9878-9888.

Muramatsu S-I, et al., "Nucleotide Sequencing and Generation of an Infectious Clone of Adeno-Associated Virus 3," 1996, *Virology*, 221:208-217, XP000608965.

Muster et al., "Physical Mapping of Adeno-Associated Virus Serotype 4 DNA" 1980, *J. Virol.*, 35(3):653-661; XP002058632.

Muzyczka, N, "Use of adeno-associated virus as a general transduction vector for mammalian cells," 1992, *Curr Top Microbiol Immunol*, 158:97-129.

Myrup, A.C., Mohanty, S.B. and Hetrick, F.M., "Isolation and characterization of adeno-associated viruses from bovine adenovirus types 1 and 2," 1976, *Am J Vet Res*, 37(8):907-910.

Naz, S., Griffit,h A.J., Riazuddin, S., Hampton, L.L., Battey, J.F. Jr, Khan, S.N., Riazuddin, S,, Wilcox, E.R., Friedman, T.B., "Mutations of *ESPN* cause autosomal recessive deafness and vestibular dysfunction," 2004, *J Med Genet*, 41(8):591-595.

No D, Yao TP, Evans RM., "Ecdysone-inducible gene expression in mammalian cells and transgenic mice," 1996, *Proc Natl Acad Sci USA*, 93(8):3346-3351.

Ogston, P., K. Raj, and P. Beard, "Productive replication of adeno-associated virus can occur in human papillomavirus type 16 (HPV-16) episome containing keratinocytes and is augmented by the HPV-16 E2 protein," 2000, *J Virol*, 74:3494-3504.

Opie et al., "Identification of amino acid residues in the capsid proteins of adeno-associated virus type 2 that contribute to heparan sulfate proteoglycan binding," 2003, *J Virol*, 77:6995-7006.

O'Riordan et al., "Scaleable Chromatographic Purification Process for Recombinant Adeno-Associated Virus (rAAV)," 2000, *J Gene Med*, 2:444-454.

Parks, W.P., J.L. Melnick, R. Rongey, and H.D. Mayor, "Physical assay and growth cycle studies of a defective adeno-satellite virus," 1967, *J. Virol.*, 1:171-180.

(56) References Cited

OTHER PUBLICATIONS

Podsakoff, G., K.K. Jr Wong, and S. Chatterjee, "Efficient gene transfer into nondividing cells by adeno-associated virus-based vectors," 1994, *J. Virol.*, 68:5656-5666.

Polishchuk R, Di Pentima A, Lippincott-Schwartz J, "Delivery of raft-associated, GPI-anchored proteins to the apical surface of polarized MDCK cells by a transcytotic pathway," 2004, *Nat Cell Biol*, 6(4):297-307.

Prasad KM, Zhou C, Trempe JP, "Characterization of the Rep78/adeno-associated virus complex," 1997, *Virology*, 229(1):183-192, XP-002125033.

Qing K, Mah C, Hansen J, Zhou S, Dwarki V, Srivastava A., "Human fibroblast growth factor receptor 1 is a co-receptor for infection by adeno-associated virus 2," 1999, *Nat Med*, 5(1):71-77.

Qiu J, Brown KE., "Integrin *alphaVbeta*5 is not involved in adeno-associated virus type 2 (AAV2) infection," 1999, *Virology*, 264(2):436-440.

Rabinowitz et al., "Cross-Packaging of a Single Adeno-Associated Virus (AAV) Type 2 Vector Genome into Multiple AAV Serotypes Enables Transduction with Broad Specificity," 2002, *J Virol*, 76(2):791-801, XP002247245.

Rabinowitz JE, Bowles DE, Faust SM, Ledford JG, Cunningham SE, Samulski RJ., "Cross-dressing the virion: the transcapsidation of adeno-associated virus serotypes functionally defines subgroups," 2004, *J Virol*, 78(9):4421-4432.

Reddy, V. S., P. Natarajan, B. Okerberg, K. Li, K. V. Damodaran, R. T. Morton, C. L. Brooks, 3rd, and J. E. Johnson, "Virus Particle Explorer (VIPER), a website for virus capsid structures and their computational analyses," 2001, *J Virol*, 75:11943-11947.

Rich DP, Couture LA, Cardoza LM, Guiggio LM, Armentano D., Espino PC, Hehir K., Welsh MJ, Smith AE, and Gregory RJ, "Development and analysis of recombinant adenoviruses for gene therapy of cystic fibrosis," 1993, *Hum. Gene Ther.*, 4:461-476.

Richardson, W. D., and H. Westphal, "Requirement for either early region 1a or early region 1b adenovirus gene products in the helper effect for adeno-associated virus," 1984, *J Virol*, 51:404-410.

Rose, J.A., M.D. Hoggan, F. Koczot, and A.J. Shatkin, "Genetic relatedness studies with adenovirus-associated viruses," 1968, *J. Virol.*, 2:999-1005.

Rosenfeld et al., "Adeno-associated viral vector gene transfer into leptomeningeal xenografts," 1997, *J Neuro-Oncology*, 34(2):139-144.

Russell et al., "Adeno-Associated Virus Vectors Preferentially Transduce Cells in S Phase," 1994, *Proc. Natl. Acad. Sci. USA*, 91:8915-8919.

Rutledge EA Halbert CL, and Russell DW, "Infectious Clones and Vectors Derived from Adeno-Associated Virus (AAV) Serotypes other Than AAV Type 2," 1998, *J. Virol.*, 72(1):309-319.

Ryan, J.H., S. Zolotukhin, and N. Muzyczka, "Sequence requirements for binding of Rep68 to the adeno-associated virus terminal repeats," 1996, *J. Virol.*, 70:1542-1553.

Rzadzinska, A. K., M. E. Schneider, et al., "An actin molecular treadmill and myosins maintain stereocilia functional architecture and self-renewal," 2004, *J Cell Biol*, 164(6):887-897.

Saffer, L. D., R. Gu, et al., "An RT-PCR analysis of mRNA for growth factor receptors in damaged and control sensory epithelia of rat utricles," 1996, *Hear Res*, 94(1-4):14-23.

Salo R. and Mayor H., "Structural Polypeptides of Parvoviruses," 1977, *Virology*, 78:340-345; XP002058634.

Samulski RJ, Chang LS, Shenk T, "Helper-free stocks of recombinant adeno-associated viruses: normal integration does not require viral gene expression," 1989, *J. Virol.*, 63(9):3822-3828, XP000283071.

Samulski, R. J., and T. Shenk, "Adenovirus E1B 55-$M_r$ polypeptide facilitates timely cytoplasmic accumulation of adeno-associated virus mRNAs," 1988, *J Virol*, 62:206-210.

Samulski, R.J., K.I. Berns, M. Tan, and N. Muzyczka, "Cloning of adeno-associated virus into pBR322: rescue of intact virus from the recombinant plasmid in human cells," 1982, *Proc Natl Acad Sci USA*, 79:2077-2081.

Sanes JR, JLR Rubenstein, and JF Nicolas, "Use of a recombinant retrovirus to study post-implantation cell, lineage in mouse embryos," 1986, *EMBO J*, 5:3133-3142.

Sanlioglu, S., Benson, P.K., Yang, J., Atkinson, E.M., Reynolds, T. and Engelhardt, J.F., "Endocytosis and nuclear trafficking of adeno-associated virus type 2 are controlled by rad and phosphatidylinositol-3 kinase activation," 2000, *J Virol*, 74:9184-9196.

Schinkel AH, "P-Glycoprotein, a gatekeeper in the blood-brain barrier," 1999, *Adv Drug Deliv Rev*, 36:179-194.

Schlehofer JR, Heilbronn R, Georg-Fries B, zur Hausen H, "Inhibition of initiator-induced SV40 gene amplification in SV40-transformed Chinese hamster cells by infection with a defective parvovirus," 1983, *Int J Cancer*, 32(5):591-595, XP009010321.

Schlehofer, J. R., M. Ehrbar, and H. zur Hausen, "Vaccinia virus, herpes simplex virus, and carcinogens induce DNA amplification in a human cell line and support replication of a helpervirus dependent parvovirus," 1986, *Virology*, 152:110-117.

Schmidt M, Grot E, Cervenka P, Wainer S, Buck C, Chiorini JA, "Identification and characterization of novel adeno-associated virus isolates in ATCC virus stocks," 2006, *J Virol*, 80(10):5082-5085.

Schneider, M. E., I. A. Belyantseva, et al., "Rapid renewal of auditory hair bundles," 2002, *Nature*, 418(6900):837-838.

Schwede, T., J. Kopp, N. Guex, and M. C. Peitsch, "Swiss-Model: An automated protein homology-modeling server," 2003, *Nucleic Acids Res*, 31:3381-3385.

Seiler MP, Miller AD, Zabner J, Halbert CL, "Adeno-associated virus types 5 and 6 use distinct receptors for cell entry," 2006, *Hum Gene Ther*, 17:10-19.

Seiler, M. P., C. L. Halbert, J. A. Chiorini, A. D. Miller, and J. Zabner, "AAV5 and AAV6 Mediate Gene Transfer to Human Airway Epthelia Via Different Receptors," 2002, *Mol Ther*, 5:S40.

Senapathy, P., J.D. Tratschin, and B.J. Carter, "Replication of adeno-associated virus DNA. Complementation of naturally occurring rep-mutants by a wild-type genome or an ori- mutant and correction of terminal palindrome deletions," 1984, *J Mol Biol*, 179:1-20.

Shou, J., J. L. Zheng, et al., "Robust generation of new hair cells in the mature mammalian inner ear by adenoviral expression of *Hath1*," 2003, *Mol Cell Neurosci*, 23(2):169-179.

Smith, R. H., S. A. Afione, et al., "Transposase-mediated construction of an integrated adeno-associated virus type 5 helper plasmid," 2002, *Biotechniques*, 33(1):204-206,208,210-211.

Snyder RO, Miao CH, Patijn GA, Spratt SK, Danos O., Nagy D., Gown AM, Winther B., Meuse L., Cohen LK, Thompson AR, and Kay MA, "Persistent and therapeutic concentrations of human factor IX in mice after hepatic gene transfer of recombinant AAV vectors," 1997, *Nat Genet*, 16:270-276.

Sobkowicz, H. M., J. M. Loftus, et al., "Tissue culture of the organ of Corti," 1993, *Acta Otolaryngol Suppl*, 502:3-36.

Srivastava et al., "Nucleotide Sequence and Organization of the Adeno-Associated Virus 2 Genome," 1983, *J. Virol.*, 45(2):555-564; XP002058633.

Staecker H, Li D, O'Malley BW Jr, Van De Water TR., "Gene expression in the mammalian cochlea: A study of multiple vector systems," 2001, *Acta Otolatyngol*, 121(2):157-163.

Stracker, T. H., G. D. Cassell, P. Ward, Y. M. Loo, B. van Breukelen, S. D. Carrington-Lawrence, R. K. Hamatake, P. C. van der Vliet, S. K. Weller, T. Melendy, and M. D. Weitzman, "The Rep protein of adeno-associated virus type 2 interacts with single-stranded DNA-binding proteins that enhance viral replication," 2004, *J Virol*, 78:441-453.

Summerford C, Bartlett JS, Samulski RJ., "*AlphaVbeta*5 integrin: a co-receptor for adeno-associated virus type 2 infection," 1999, *Nat Med*, 5(1):78-82.

Summerford, C. and R. J. Samulski, "Membrane-associated heparan sulfate proteoglycan is a receptor for adeno-associated virus type 2 virions," 1998, *J Virol*, 72(2):1438-1445.

Superti, F., M. L. Marziano, A. Tinari, and G. Donelli, "Effect of polyions on the infectivity of SA-11 rotavirus in LCC-MK2 cells," 1993, *Comp Immunol Microbiol Infect Dis*, 16:55-62.

Suzuki, H., Y. Katori, at al., "Carbohydrate distribution in the living utricular macula of the guinea pig detected by lectins," 1995, *Hear Res*, 87(1-2):32-40.

(56) References Cited

OTHER PUBLICATIONS

Teramoto, S., Bartlett Js, McCarty DXX, Samulski RJ, and Boucher RC, "Factors influencing adeno-associated virus-mediated gene transfer to human cystic fibrosis airway epithelial cells: comparison with adenovirus vectors," 1998, *J Virol*, 72:8904-8912.

Thomas CE, Storm TA, Huang Z, Kay MA, "Rapid uncoating of vector genomes is the key to efficient liver transduction with pseudotyped adeno-associated virus vectors," 2004, *J Virol*, 78(6):3110-3122.

Tratschin, J. D., M. H. West, T. Sandbank, and B. J. Carter, "A human parvovirus, adeno-associated virus, as a eucaryotic vector: transient expression and encapsidation of the procaryotic gene for chloramphenicol acetyltransferase," 1984, *Mol Cell Biol*, 4:2072-2081.

Tratschin, J.D., I.L. Miller, and B.J. Carter, "Genetic analysis of adeno-associated virus: properties of deletion mutants constructed in vitro and evidence for an adeno-associated virus replication function," 1984, *J. Virol.*, 51:611-619.

Trempe, J.P. and B.J. Carter, "Regulation of adeno-associated virus gene expression in 293 cells: control of mRNA abundance and translation," 1988, *J. Virol*, 62:68-74.

Trempe, J.P., E. Mendelson, and B.J. Carter, "Characterization of adeno-associated virus rep proteins in human cells by antibodies raised against rep expressed in *Escherichia coli*," 1987, *Virology*, 161:18-28.

Tuma PL and Hubbard AL, "Transcytosis: crossing cellular barriers," 2003, *Physiol Rev*, 83(3):871-932.

Voutetakis A, Kok MR, Zheng C, Bossis, Wang J, Cotrim AP, Marracino N, Goldsmith CM, Chiorini JA, Loh YP, Nieman LK, Baum BJ, "Reengineered salivary glands are stable endogenous bioreactors for systemic gene therapeutics," 2004, *Proc Natl Acad Sci USA*, 101(9):3053-3058.

Walsh, C.E., J.M. Liu, X. Xiao, N.S. Young, A.W. Nienhuis, and R.J. Samulski, "Regulated high level expression of a human gamma-globin gene introduced into erythroid cells by an adeno-associated virus vector," 1992, *Proc Natl Acad Sci USA*, 89:7257-7261.

Walters, R.W., Yi, S.M., Keshavjee, S., Brown, K.E., Welsh, M.J., Chiorini, J.A. and Zabner, J., "Binding of adeno-associated virus type 5 to 2,3-linked sialic acid is required for gene transfer," 2001, *J Biol Chem*, 276:20610-20616.

Walters, RW, Duan D., Engelhardt JF, and Welsh MJ., "Incorporation of adeno-associated virus in a calcium phosphate coprecipitate improves gene transfer to airway epithelia in vitro and in vivo," 2000, *J. Virol.*, 74:535-540.

Walters, RW, Grunst T., Bergelson JM, Finberg RW, Welsh MJ, and Zabner J., "Basolateral localization of fiber receptors limits adenovirus infection from the apical surface of airway epithelia," 1999, *J. Biol. Chem.*, 274:10219-10226.

Walz, C., A. Deprez, T. Dupressoir, M. Durst, M. Rabreau, and J. R. Schlehofer, "Interaction of human papillomavirus type 16 and adeno associated virus type 2 co-infecting human cervical epithelium," 1997, *J Gen Virol*, 78(Pt 6):1441-1452.

Wang G., Davidson BL, Melchert P., Slepushkin VA, van Es HH, Bodner M., Jolly DJ, and McCray PBJr., "Influence of cell polarity on retrovirus-mediated gene transfer to differentiated human airway epithelia," 1998, *Journal of Virology*, 72:9818-9826.

Wang X S, and A Srivastava, "Rescue and autonomous replication of adeno-associated virus type 2 genomes containing Rep-binding site mutations in the viral p5 promoter," 1998, *J Virol*, 72:4811-4818.

Ward, P., F. B. Dean, M. E. O'Donnell, and K. I. Berns, "Role of the adenovirus DNA-binding protein in in vitro adeno-associated virus DNA replication," 1998, *J Virol*, 72:420-427.

Weindler, F. W., and R. Heilbronn, "A subset of herpes simplex virus replication genes provides helper functions for productive adeno-associated virus replication," 1991, *J Virol*, 65:2476-2483.

Winocour, E., M.F. Callaham, and E. Huberman, "Perturbation of the cell cycle by adeno-associated virus," 1988, *Virology*, 167:393-399.

Xiao, W., N. Chirmule, S. C. Berta, B. McCullough, G. Gao, and J. M. Wilson, "Gene therapy vectors based on adeno-associated virus type 1," 1999, *J Virol*, 73:3994-4003.

Xiao et al., "Efficient Long-Term Gene Transfer into Muscle Tissue of Immunocompetent Mice by Adeno-Associated Virus Vector," 1996, *J. Virol.*, 70(11):8098-8108.

Xiao XM Li J, Samulski RJ, "Production of High-Titer Recombinant Adeno-Associated Virus Vectors in the Absence of Helper Adenovirus," 1997, *J Virol*, 72(3):2224-2232.

Xie Q. and Chapman MS, "Canine parvovirus capsid structure, analyzed at 2.9 Åresolution," 1996, *J Mol Biol*, 264:497-520.

Yalkinoglu, A.O., Heilbronn, R., Burkle, A., Schlehofer, J.R. and zur Hausen, H., "DNA amplification of adeno-associated virus as a response to cellular genotoxic stress," 1988, *Cancer Res*, 48:3123-3129.

Yakobson, B., Hrynko, T.A., Peak, M.J. And Winocour, E., "Replication of adeno-associated virus in cells irradiated with UV light at 254 nm," 1989, *J Virol*, 63:1023-1030.

Yamano, S., Huang, L.Y., Ding, C., Chiorini, J.A., Goldsmith, C.M., Wellner, R.B., Golding, B., Kotin, R.M., Scott, D.E. and Baum, B.J., "Recombinant adeno-associated virus serotype 2 vectors mediate stable interleukin 10 secretion from salivary glands into the bloodstream," 2002, *Hum Gene Ther*, 13:287-298.

Yamaya, M., Finkbeiner WE, Chun SY, and Widdicombe JH, "Differentiated structure and function of cultures from human tracheal epithelium," 1992, *Am.J.Physiol*, 262:L713-L724.

Zabner J, Seiler M, Walters R, Kotin Rm, Fulgeras W, Davidson BL, Chiorini JA, "Adeno-associated virus type 5 (AAV5) but not AAV2 binds to the apical surfaces of airway epithelia and facilitates gene transfer," 2000, *J Virol.*, 74(8):3852-3858, XP002197205.

Zabner, J., Zeiher BG, Friedman E, and Welsh MJ, "Adenovirus-mediated gene transfer to ciliated airway epithelia requires prolonged incubation time," 1996, *J.Virol.*, 70:6994-7003.

Zhang JR, Mostov Ke, Lamm ME, Nanno M, Shimida S, Ohwaki M, Tuomanen E, "The polymeric immunoglobulin receptor translocates pneumococci across human nasopharyngeal epithelial cells," 2000, *Cell*, 102(6):827-837.

Zhu ZB, Makhija SK, Lu B, Wang M, Rivera AA, Preuss M, Zhou F, Siegal GP, Alvarez RD, Curiel DT, "Transport across a polarized monolayer of Caco-2 cells by transferrin receptor-mediated adenovirus transcytosis," 2004, *Virol*, 325:116-128.

Zolotukhin et al., "Recombinant Adeno-Associated Virus Purification using Novel Methods Improves Infectious Titer and Yield," 1999, *Gene Ther*, 6:973-985.

Schmidt, et al., "Cloning and Characterization of a Bovine Adeno-Associated Virus," Journal of Virology, vol. 78, No. 12, Jun. 2004, pp. 6509-6516.

Chiorini, et al., "Cloning and Characterization of Adeno-Associated Virus Type 5," Journal of Virology, vol. 73, No. 2, Feb. 1999, pp. 1309-1319.

Chiorini, et al., "Cloning of Adeno-Associated Virus Type 4 (AAV4) and Generation of Recombinant AAV4 Particles," Journal of Virology, vol. 71, No. 9, Sep. 1997, pp. 6823-6833.

Pasquale, et al., "A Novel Bovine Virus Efficiently Transduces Inner Ear Neuroepithelial Cells," Molecular Therapy, vol. 11, No. 6, Jun. 2005, pp. 849-855.

Katano, et al., "Identification of adeno-associated virus contamination in cell and virus stocks by PCR," Biotechniques, Apr. 2004, vol. 36, No. 4, Apr. 2004, pp. 676-680.

Coria, et al., "Isolation and identification of bovine adenovirus type 3 with an adenovirus-associated virus," American Journal of Veterinary Research, vol. 39, No. 12, 1978, pp. 1904-1906.

GenBank Accession No. AY186198.1, dated Jun. 5, 2003.

Bergelson, JM, Cunningham JA, Droguett G., Kurt-Jones EA, Krithivas A., Hong JS, Horwitz MS, Crowell RL, and Finberg RW, "Isolation of a common receptor for Coxsackie B viruses and adenoviruses 2 and 5," 1997, *Science*, 275:1320-1323.

Berns, K. I., "Parvoviridae: the viruses and their replication," in F. B. N., K. D. M., and H. P. M. (ed.), *Fields virology*, 3rd ed. Lippincott-Raven Publishers, Philadelphia, PA, p. 2173-2197.

Blacklow, et al., "Serologic Evidence for Human Infection With Adenovirus-Associated Viruses," 1968, *J NCI*, 40(2):319-327.

Blacklow, N.R., Hoggan, M.D. and Rowe, W.P. "Isolation of adenovirus-associated viruses from man," 1967, *Proc Natl Acad Sci U S A*, 58:1410-1415.

(56) References Cited

OTHER PUBLICATIONS

Bomsel M, Alfsen A, "Entry of viruses through the epithelial barrier: pathogenic trickery," 2003, *Nat Rev Mol Cell Biol*, 4:57-68.

Bomsel M, David V, "Mucosal gatekeepers: selecting HIV viruses for early infection," 2002, *Nat Med*, 8:114-116.

Bossis, I. and Chiorini, J.A., "Cloning of an Avian Adeno-Associated Virus (AAAV) and Generation of Recombinant AAAV Particles," 2003, *J Virol*, 77(12):6799-6810.

Burcin, M.M., O'Malley, B.W. and S.Y. Tsai, "A regulatory system for target gene expression," 1998, *Frontiers in Bioscience*, 3:c1-7.

Carter, B. J., B. A. Antoni, and D. F. Klessig, "Adenovirus containing a deletion of the early region 2A gene allows growth of adeno-associated virus with decreased efficiency," 1992, *Virology*, 191:473-476.

Carter, B. J., C. A. Laughlin, L. M. de la Maza, and M. Myers, "Adeno-associated virus autointerference," 1979, *Virology*, 92:449-462.

Casto, B. C., R. W. Atchison, and W. M. Hammon, "Studies on the relationship between adeno-associated virus type I (AAV-1) and adenoviruses. I. Replication of AAV-1 in certain cell cultures and its effect on helper adenovirus," 1967a, *Virology*, 32:52-59.

Casto, B. C., J. A. Armstrong, R. W. Atchison, and W. M. Hammon, "Studies on the relationship between adeno-associated virus type 1 (AAV-1) and adenoviruses. II. Inhibition of adenovirus plaques by AAV; its nature and specificity," 1967b, *Virology*, 33:452-458.

Chang, L.S. and Shenk, T., "The adenovirus DNA-binding protein stimulates the rate of transcription directed by adenovirus and adeno-associated virus promoters," 1990, *J Virol*, 64:2103-2109.

Chang, L.S., Y. Shi, and T. Shenk, "Adeno-associated virus P5 promoter contains an adenovirus E1A-inducible element and a binding site for the major late transcription factor,"1989, *J. Virol.*, 63:3479-3488.

Chao H et al., "Several Log Increase in Therapeutic Transgene Delivery by Disticnt Adeno-Associated Viral Serotype Vectors," 2000, *Molecular Therapy*, 2(6):619-623.

Chejanovsky, N. and B.J. Carter, "Replication of a human parvovirus nonsense mutant in mammalian cells containing an inducible amber suppressor," 1989a, *Virology*, 171:239-247.

Chejanovsky, N. and B.J. Carter, "Mutagenesis of an AUG codon in the adeno-associated virus rep gene: effects on viral DNA replication," 1989b, *Virology*, 173:120-128.

* cited by examiner

FORMATTED ALIGNMENTS OF AAV GENOMES

```
              10          20          30          40
AAV2   T T G G C C A C T C C C T C T C T G C G C G C T C G C T C G C T C A C
AAV4   T T G G C C A C T C C C T C T A T G C G C G C T C G C T C A C T C A C
AAV5   T G G C A C T C T C C C C C C T G T C G C G T T C G C T C G C T C G C T G G C
BAAV   G T G G C A C T C C C C C C C C T G T C G C G T T C G C T C G T T C G C T G G C
       G T G G C W Y K S C C M C Y C C Y K Y Y V Y G Y K C G C T C G C T C G C T S R C
              50          60          70          80
AAV2   T G A G G C C G G C G A C C A A A G G T C G C C C G A C G C C G G G C T T T
AAV4   T C G G C C C T G G A G A C C A A A G G T C T C C A G A C T G C C G G C C T C T
AAV5   T C G T T T G G G G G G T G G C A G C T C A A A G A G C T G C C A G A C G A C
BAAV   T C G A T T G G G C G G T G G C A G C T C A A A G A G C T G C C A G A C G A C
       T C G D B Y S G G G V G R Y S R M A G S T C D M M V R R C T G C C R G V C K H Y
              90         100         110         120
AAV2   G C C C G G G C G G C C T C A G T G A G C G A G C G A G C G C G C A G A G A G G
AAV4   G G C C G G C A G G G C C G A G T G A G T G A G C G A G C G C G C A T A G A G G
AAV5   G G C C C T C T G G - - C C G T C G C C C C C C A A A C G A G C - - - C A G C
BAAV   G G C C C T C T G G G - C C G T C G C C C C C C A A T C G A G C - - - C A G C
       G G C C S K C H G G G C C C R K Y G M S C S M S C R A D C G M G C A K A S A G S
             130         140         150         160
AAV2   G A G T G G C C A A C T C C A T C A C T A G G G G T T - - - - - - - - - - - - -
AAV4   G A G T G G C C A A C T C C A T C A T C T A G G T T T G C C C A C T G A C G T C
AAV5   G A G C G A G C G A A C G C G A C A G G G G G G A G A G T - - - - - G C C A C
BAAV   G A A C G A G C G A A C G C G A C A G G G G G G G G A G T - - - - - G C C A C
       G A G Y G R S C R A M Y S C R W C A B B D G G G D K W G T C C A C T G G C C A C
             170         180         190         200
AAV2   - - - - - - - C C T G G A G - - - G G T G G - - - - - - - - - A G T C
AAV4   A T G T G A C G T C C T A G G G T T A G G G A G G T C C C T G T A T T A G C A
AAV5   A C T C T C A A G C A A G G G G G T T T T G T A A G C A G T G A T G T C A T A A
BAAV   A C T C T C T A G C A A G G G G G T T T T G T A G G T G G T G A T G T C A T T G
       A C T C T C A A G C M M K G G G G T T T K G K A G G T V G T G A T G T C A K H V
             210         220         230         240
AAV2   G T G A C G T G A A T - - - T A C G T C A T A G G G T T A G G G A G G T C C T
AAV4   G T C A C G T G A G T G T C G T A T T T C G C G G A G C G T A G C G G A G C G C
AAV5   T - G A T G T A A T G C T T A T T G T C A C G C G A T A G T T A A T G A T T A
BAAV   T T G A T G T C A T T A T A G T T G T C A C G C G A T A G T T A A T G A T T A
       K T G A Y G T V A D T V T H G T A T G T C A C G S G R T D D D K V A K G D Y B H
```

```
          490              500              510              520
AAV2  A A T G G A G T T G C C G C C A G A T T C T G A C A T G G A T C T G A A T C T
AAV4  A A T G G A G C T G C C G C C G G A T T C T G A C A T G G A C T T G A A T C T
AAV5  T T T G G A G C T G C C T C C A G A G T C A G A T T T A A A T T T G A C T C T
BAAV  T T T G G A G C T G C C T C C C G A G T C A G A T T T G A A T T T G A C T C T
      W W T G G G A G C T G C C K C C V G A K T C W G A Y W T G R A T T T G A M T C T
          530              540              550              560
AAV2  G A T T G A G C A G G C A C C C T G A C C G T G G C C G A G A A G C T G C A G
AAV4  G A T T G A G C A G G C A C C C T G A C C G T G G C C G A A A A G C T G C A A
AAV5  G G T T G A A C A G C C T C A G T T G A C G G T G G C T G A T A G A A T T C G C
BAAV  G A T T G A G C A G C C T C A G C T G A C G G T G G C T G A C A G A A T T C G C
      G A T T G A G C A G S C W C M S C T G A C S G T G G C Y G A   A R R M T K C R V
          570              580              590              600
AAV2  C G C G A C T T T C T G A C G G A A T G G C G C C G T G T G A G T A A G G C C C
AAV4  C G C G A G T T C C T G G T C G A G T G G C G C C G C G T G A G T A A G G C C C
AAV5  C G C G T G T T C C T G T A C G A G T G G A A C A A A T T T T C C A A G - - - C
BAAV  C G C G T G T T C C T G T A C G A G T G G A A C A A A T T T T C C A A G - - - C
      C G C G W G T T C C T G D H C G A G T G G M R C M R H K T K W S Y A A G G C C C
          610              620              630              640
AAV2  C G G A G G C C C T T T C T T T G T G C A A T T T G A G A A G G A G A G A G
AAV4  C G G A G G C C C T C T C T T C T T T G T C C A G T T C G A G A A G G G G A C A G
AAV5  A G G A G T C C A A A T T C T T T G T G C A G T T T G A A A A G G A T C T G A
BAAV  A G G A G A G C A A A T T C T T T G T G C A G T T T G A A A A G G A T C T G A
      M G G A G D C C M W H T T C T T T G T G C A G T T T G A R A A G G G A K M B R R
          650              660              670              680
AAV2  C T A C T T C C A C A T G C A C G T G C T C G T G G A A A C C A C C G G G G T G
AAV4  C T A C T T C C A C C T G C A C A T C C T G G T G G A G A C C G T G G G C G T C
AAV5  A T A T T T T C A T C T G C A C A C G C T T G T G G A G A C C T C C G G C A T C
BAAV  A T A T T T T C A T C T G C A C A C G C T T G T G G A G A C C T C C G G C A T C
      M T A Y T T Y C A Y C T G C A C A Y G C T B G T G G A G A C C D C C G G C R T C
          690              700              710              720
AAV2  A A A T C C A T G G T T T T G G A C G T T C C T G A G T C A G A T T C G C G
AAV4  A A A T C C A T G G T G G G T G G G C C G C T A C G T G A G C C A G A T T A A A G
AAV5  T C T T C C A T G G T C C T C G G C C G C T A C G T G A G T C A G A T T C G C G
BAAV  T C T T C T T A T G G T C C T T G G C C G C T A C G T G A G T C A G A T T C G C G
      W M W T C C A T G G T B B T B G G C C G C T A C G T G A G T C A G A T T C G C G
```

FIG.1A (CONTINUED)

```
              730              740              750              760
AAV2  A A A A A C T G A T T C A G A G A A T T T A C C G C G G G A T C G A G C C G A C
AAV4  A G A A G C T G G T G A C C C G C A T C T A C C G C G G G T C G A G C C G C A
AAV5  C C C A G C T G G T G A A A G T G G T C T T C C A G G G A A T T G A A C C C A
BAAV  C C C A G C T G G T G A A G G T G G T G T T C C A G A A C A T T G A G C C G C G
      M V M A G C T G G T G A A V V K V R T B T W C C R S G G V A T Y G A G C C G C V
              770              780              790              800
AAV2  T T T G C C A A A C T G G T T C G C G G T C A C A A A G A C C A G A A T G G C
AAV4  G C T T C C G A A C T G G T T C G C G G T G A C C A A G A C G C G T A A T G G C
AAV5  G A T C A A C G A C T G G T C G C C A T C A C C A A G G T A A A G A A G G C G -
BAAV  G A T T A A C G A C T G G T C G C C A T C A C C A A G G T A A A G A A G G G -
      G H T B M M V R A C T G G K T C G C S R T C A C C A A G R Y V A R D A A K G G C
              810              820              830              840
AAV2  G C C G G A G G C G G G A A C A A G G T G G T G G A T G A G T G C T A C A T C C
AAV4  G C C G G A G G C G G G A A C A A G G T G G T G G A C G A C T G C T A C A T C C
AAV5  - - C G G A G C C - - A A T A A G G T G G T G G A T T C T G G T A T A T T C
BAAV  - - C G G A G C C - - A A T A A G G T G G T G G A T T C T G G G T A T A T T C
      G C C G G A G S C G G G A A Y A A G G T G G T G G A T K M B K G S T A Y A T Y C
              850              860              870              880
AAV2  C C A A T T A C T G C T C C C C A A A A C C C A G C C T G A G C T C C A G T G
AAV4  C C A A C T A C C T G C T C C C C A A G A C C C A G C C C G A G C T C C A G T G
AAV5  C C G C C T A C C T G C T G C C G A A G G T C C A A C C G G A G C T T C A G T G
BAAV  C C G C C T A C C T G C T G C C G A A G G T C C A A C C A G A G C T T C A G T G
      C C R M C T A C C T G C T S C C S A A G R Y C C A R C C   G A G C T Y C A G T G
              890              900              910              920
AAV2  G C G T G G A C T A A T A T G G A A C A G T A T T T A A G C G C C T G T T T G
AAV4  G G C G T G G A C T A A C A T G G A C C A G T A T A T A A G C G C C T G T T T G
AAV5  G G C G T G G A C A A A C C T G G A C G A G T A T A A A T T G G C C G C C C T G
BAAV  G G C G T G G A C T A A C C T C G A A G A G T A T A A A T T G G C C G C C C T C
      G G C G T G G A C T A A C M T G G A M S A G T A T A W A W K S G C C K S Y Y T G
              930              940              950              960
AAV2  A A T C T C A C G G A G C G T A A A C G G T T G C T G G C G G C A G C A T C T G A
AAV4  A A T C T C G C G G A G C G T A A A C G G C T G G T G G G C G C A G C A T C T G A
AAV5  A A T C T G G A G G A G C G C A A A C G G C T C G T C G C G C A G T T T C T G G
BAAV  A A T C T G G A G G A G C G C A A A C G G C T C G T C G C T C A G T T T C A G C
      A A T C T S G M G G A G C G Y A A A C G G C T S G T S G C G C A G Y W T C T G V
```

```
              1210              1220              1230              1240
AAV2  T G A G C C T G A C T A A A A C C G C C C C G A C T A C C T G G T G G G C C A
AAV4  T G A G C C T G A C A A A G A C G G C T C C G G A C T A C C T G G T G G G C C A
AAV5  T G A G T C T G A C A A A A G C G C G G T G G A C T A C C T C G T G G G G A G
BAAV  T G A G T C T G A C C A A T C T G C C T C A G A C T A T C T C G T G G A C A
      T G A G Y C T G A C H A A A A C B G C B B C V G A C T A C C T S G T G G G V C A
              1250              1260              1270              1280
AAV2  G C A G C C C G T G G A G G A C A T T T C C A G C A A T C G G A T T T A T A A A
AAV4  G A A C C C G C C G G A G G A C A T T T C C A G C A A C G C A T C T A C C G A
AAV5  C T C C G T T C C C G A G G A C A T T T C A A A A A A C A G A A T C T G G C A A
BAAV  G A C T G T T C C A G A G G A C A T T T C T G A A A A C A G A A T C T G G C A G
      G H M B S Y B C C V G A G G A C A T T T C H A R M A A C M G V A T C T R B C A A
              1290              1300              1310              1320
AAV2  A T T T T G A A C T A A A C G G T A C G A T C C C C A A T A T G C G G C T T
AAV4  A T C C T C G A G A T G A A C G G G T A C G A T C C G C A G T A C G C G G C C T
AAV5  A T T T T T G A G A T G A A T G G C T A C G A C C C G G C C T A C G C G G G A T
BAAV  A T T T T T G A T C T C A A C G G C T A C G A C C C G G C A T A C G C G G G C T
      A T T T T B G A D M T V A A C G G S T A C G A Y C C G S M V T A C G C G G S H T
              1330              1340              1350              1360
AAV2  C C G T C T T T C T G G G A T G G C C A C G A A A A A G T A C G G C A A G A G
AAV4  C C G T C T T T C C T G G G C T G G C G C G C A A A A G A A G T T C G G G A A G A G
AAV5  C C A T C C T C T A C G G C T G G T G T C A G C G C T C C T T C A A C A A G A G
BAAV  C T G T T C T C T A C G G C T G G T G C A C T C G C G C C T T T G G A A A G A G
      C C G T C Y T C Y W S G G C T G G K S B M M D M R V D M S T T C G G V A A G A G
              1370              1380              1390              1400
AAV2  G A A C A C C A T C T G G C T G T T T G G C C T G C A A C T A C C G G A A G
AAV4  G A A C A C C A T C T G G C T C T T T G G C C G G C C A C G A C G G G T A A A
AAV5  G A A C A C C G T C T G G C T C T A C G G A C C G C C A C G A C C G G C A A G
BAAV  G A A C A C C G T C T G G C T G T A T G G A C C C G C A C C A C C G G A A A G
      G A A C A C C R T C T G G C T S T W T G G R C C B G C V A C B A C C G G   A A G
              1410              1420              1430              1440
AAV2  A C C A A C A T C G C G G A G C C A T A G C C C A C A C T G T G C C C T T C T
AAV4  A C C A A C A T C G C G G A A G C C A T C G C C C A C G C C G T G C C C T T C T
AAV5  A C C A A C A T C G C G G A G G C C A T C G C C C A C A C T G T G C C C T T T T
BAAV  A C C A A C A T C G C G G A A G C C A T C T C T C A C A C C G T G C C C T T Y T
      A C C A A C A T C G C G G A R G C C A T C G C C C A C A C Y G T G C C C T T Y T
```

```
                3370              3380              3390              3400
AAV2    C C G C C G T T C C C A G C A G A C G T C T T C A T G C T G C C A C A G T A T G
AAV4    C C T C C T T T T T C C C A A C G A C G T C T T T A T G C T G C C C C A G T A C G
AAV5    C C G G C T T C C C T C C G C A G G T C T T T A C G C T G C C G C A G T A C G
BAAV    C C T C C T T T C C C C A A C G A C G T G T T C A T G C T G C C T C A G T A C G
        C C K C C B T T C C C H V M V G A C G T C T T Y A T G G T G C C   C A G T A C G
                3410              3420              3430              3440
AAV2    G A T A C T C A C C C T G A A C A A C G G G A G T - - C A G G C A G T A G G A
AAV4    G C T A T G T G G A C T G G T G A C C G G C A A C A C T T C G C A G C A A C A
AAV5    G T T A C - G C C A - - C G C T G A A C C G C G A C A A C A G A A A A T C C
BAAV    G G T A C T G C G G A C T G G T A A C C G G A G G C A G C T C T C A A A C C A
        G   T A C T G C G V A C T G V T V A M C G G V R R C A V C W C D C A R H A   C A
                3450              3460              3470              3480
AAV2    C G C T C - - - - - - - T T C A T T T A C T G C C T G G A G T A C T T T C C T
AAV4    G A C T G A C A G A A A T G C C T T C T A C T G C C T G G A G T A C T T T C C T
AAV5    C A C C G A G A G G A G C A G C T T C T T C T G C C T A G A G T A C T T T C C C
BAAV    G A C A G A C A G A A A T G C C T T C T A C T G T C T G G A G T A C T T T C C C
        S A C H G A C A G A A A T D C C T T C T A C T G C C T G G A G T A C T T T C C Y
                3490              3500              3510              3520
AAV2    T C T C A G A T G C T G C G T A C C G G A A A C A A C T T T A C C T T C A G C T
AAV4    T C G C A G A T G C T G C G G A C T G G C A A C A A C T T T G A A A T T A C G T
AAV5    A G C A A G A T G C T G A G A A C G G G C A A C A A C T T T G A G T T T A C C T
BAAV    A G C C A G A T G C T G A G A A C C G G A A A C A A C T T T G A G A T G G T G T
        W S B C A G A T G C T G M G D A C B G G M A A C A A C T T T G A V W T B A B S T
                3530              3540              3550              3560
AAV2    A C A C T T T T G A G G A C G T T C C T T T C C A C A G C A G C T A C G C T C A
AAV4    A T A G T T T T G A G A A G G T G C C T T T C C A C T G A T G T A C G C G C A
AAV5    A C A A C T T T G A G G A G G T G C C C T T C C A C T C C A G C T T C G C T C C
BAAV    A C A A G T T T G A A A A C G T G C C C T T C C A C T C C A T G T A C G C T C A
        A C A V B T T T G A G R A S G T G C C Y T T C C A C T C C A K S T A C G C T C A
                3570              3580              3590              3600
AAV2    C A G C C A G A G T C T G G A C C G T C T T C A T G A A T C C T C T C A T C G A C
AAV4    C A G C C A G A G C C T G G A C C G G C T G A T G A A C C C T C T C A T C G A C
AAV5    C A G T C A G A A C C T G T T C A A G T C G C C A A C C G C T G G T G G A C
BAAV    C A G C C A G A G C C T G G A T A G G C T G A T G A A C C C G C T G C T G G A C
        C A G C C A G A G C C T G G A C M G G C T G A T G A A C C C K C T S V T S G A C
```

FIG.1A (CONTINUED)

```
              3610           3620            3630           3640
AAV2  CAGTACCTGT ATTACTT GAGCAGA ACAAACACT CCAA GTG
AAV4  CAGTACCTGT GGGGACT GCAATCG ACCACCAC CGGA ACCA
AAV5  CAGTA T TGT ACCGCTT CGTGAGC AC-------AA A T AA
BAAV  CAGTACCTGT GGGAGCT CCAGTCT ACCACCT CTGG AGGAA
      C A G T A C C T G T R B B R V Y T S V D V W S   A C C A C C A C T G V A A B H A
              3650           3660            3670           3680
AAV2  G A A C C A C C A C G C A G T C A A - - G G C T T C A G T T T T C T C A G G C C
AAV4  C C C T G A A T G C C G G G A C T G C C A C C C A A C T T T C C A A G C T
AAV5  C A T G G C G G A G T C C A G T T C A A C A A G - - - - - - - - - - A A C T
BAAV  C T C T C A A C C A G G C A A T T C A G C C A C C A A C T T T G C C A A G C T
      C H C T S A M B V M G B V S A V T D C A R C C A B C A A C T T T V C C A A G C T
              3690           3700            3710           3720
AAV2  G G A G C G - A G T G A C A T T C G G G A C C A G T C T A G G A A C T G G C T T
AAV4  G C G G C C T A C C A A C T T T C C A A C T T T A A A A A G A A C T G G C T G
AAV5  G G C C G G G A G A T A C G - - - C A A C A C C T A C A A A A A C T G G T T C
BAAV  G A C C A A A A C A A A C T T T T C T G G C T A C C G C A A A A A C T G G C T C
      G V V S V V D A S H D A C D T T T C B R A C H H B H V H A A R A A C T G G C T B
              3730           3740            3750           3760
AAV2  C C T G G A C C T G T T A C G C C A G C A G C A G T A T C A A G A C A T
AAV4  C C C G G G C C T T C A A T C A A G C A G C A G G G C T T C T C A A A G A C T G
AAV5  C C G G G G C C C A T G G - - - - - - - - G C C G A A - - - C C C A G C G C T G
BAAV  C G G G G C C C A T G A T G A A G C A G C A G A T T C T C A A G A C T G
      C C B G G G C C C W B D D T C A A G C A G C A G V G A T T C T C M A A G A C T G
              3770           3780            3790           3800
AAV2  C T G C G G A T A A C A A C A C A G - - - T G A A T A C T C G T G G A C T G G
AAV4  C C A A T C A A A A C T A C A A G A T C C C T G C C A C C G G G T C A G A C A G
AAV5  G - A A C C T G G G C T C C G G G G T C A A C C G C G C A G T G T C A G C - G
BAAV  C C A G T C A A A A C T A C A A G A T T C C C C A G G G A A G A A A C A A C A G
      C C A V B C A D A A C T A C A A G A T C C C Y S V V D V C D G D D   V A V C A G
              3810           3820            3830           3840
AAV2  A G C T A C C A A G T A C C A C C T C A A T G G C A - - - - - G A G A C T C T C
AAV4  T C T C A T C A A T A C G A G A C G C A C A G C A C T C T G G A C G G A A G A
AAV5  C C T T C G C C A C G A C C A A - - T A G G A T G G A G C T C G A G G G C G C G
BAAV  T C T G C T C C A T T A T G A G A C C A G A A C T A C C C T C G A C G G A A G A
      H C T B M B C M A   T A C S A V A C B A R   A B B A C B C T C G A S G G H V B V
```

FIG.1A (CONTINUED)

```
                3850           3860           3870           3880
AAV2  T G G T G A A T C C G G C C C - - - - - - G G C A T G G C A A G C A C A
AAV4  T G G A G T G C C C T G A C C C C - - - - G G A C C T C C A A T G G C A C G
AAV5  A G T T A C C A G G T G C C C C G C A G C G G A A C G G C A T G A C C A A C A
BAAV  T G G A G C A A T T T T G C C C C G - - - G G A A C G G C C A T G G C A C C
      T G G W G H V H B B T G V C C C C G C A G C G G A M C D B C V H D R G C M A C V 3890           3900           3910           3920
AAV2  A G G A C G A - - T G A A G A A A G T T T T T T C C T C A G A G C G G G G T T
AAV4  G C T G G A C - - C T G C G G A C A G C A A G T T C A G C A A C A G C A G C T
AAV5  A C C T C A G G G C A G C A A C A C C T A T G C C C T G G A G A A C A C T A T
BAAV  G C A G C A - - A C G A C G C A C A C C T C T C A G G C C A C T
      R C   D C V A G G   B R V S R A C A S C D A B T T C H B B V A V R V C V V G H T 3930           3940           3950           3960
AAV2  C T C A T C T T T G G - - - A A G C A A G G C T C A G A G A A A - A C A A A T
AAV4  C A T C T T T G C G G G - - G C C T A A A C A G A A C G G C A A C A C G G C C
AAV5  G A T C T T C A A C A G C A G C C G G C G A A C C C G G G C A A C A C C G C C
BAAV  C A T C T T T G C G G G - - - G C C C A A C A T C A C C G G C A A C A C C A C C
      C A T C T T T D H G G G C C A G C C B A A V V H B M M S G G C A A C A C V R C C 3970           3980           3990           4000
AAV2  G T G G A C A T T G A A - - - A G G G T C A T G A T T A C A G A C G A A G A G G
AAV4  A C C G T A C C C G G G - - - A C T C T G A T C T T C A C T C T G A G G A G G
AAV5  A C G T A C C T G A G G G C A A C A T G C T C A T C A C C A G C G A G A G C G
BAAV  A C A G A T G C C A A - - - T A A C C T G A T G T T C A C T T C A G A A G A T G
      A C V G A H V Y C G A G G G Y A A B V T G A T S W T C A C H D V H G A R G A B G 4010           4020           4030           4040
AAV2  A A T C A G C A C A A A C A A T C C G G T G G C T A C G G C A G T A T G G
AAV4  A G C T G G C A G C C A C C A A C G C C A C C G A T A C G G A C A T G T G G G
AAV5  A G A C G C A G C C G G T G A A C C G C G T G G C G T A C A A C G T C G G C G
BAAV  A A C T A G G C G C C A C C A A C C C C G G G A C A C T G A C C T G T T T G G
      A R M T B V V G V C V A C C A A C C C C V B G G M A C B G A C V T G T D B G G 4050           4060           4070           4080
AAV2  T T C T G T A T C T A C C A A C T C C A G A G A G G C A A C A G A C A A G C A
AAV4  C A A C C T A C C T G G C G G T G A C C A G A G C A A C G C A A C C T G C C G
AAV5  G C A G A T G G C C A C C A A C A A C C A G A G C T C A C C A C T G C C C C C
BAAV  C C A C T G G C A A C C A A C C A G C A A A C G G C A C A C C G T T C C T
      B H A B V T R B C H A C C A A C V A C C A G A G C D V C A V C A V H S H   C C
```

```
         4570           4580           4590           4600
AAV2  TTCAGTGAACTTTGGTCTCTGCGTATTTCTT-TCTTATC
AAV4  TTCAGTGAACTTTGGTCTCCGTGTCCTTCTTATCCTATC
AAV5  GTCAGTAAAATACTGCCTCTTGTGGTCATCAATGAATAA
BAAV  TTCAGTAAAATACTGCCTCTTGTGGTCATCGGCGTACAA
      TTCAGTWRAAYWYTGSYYYYTGTGKHCWTYYDATSTWHWM
         4610           4620           4630           4640
AAV2  TAGTTCCATGCTAC---GTAGTAAGTAGC----------
AAV4  TCGTTCCATGCTACTGCGTACATAAGCAGCGGCCTGCG
AAV5  CAGCTTACA--ACATC----TACAAAACCTCC-------
BAAV  CAGCTTACA--ACACC---AACAAACCCC---------
      YAGYTTMCATGRCWACTGCGTACAWAASCHSCGGCCTGCG
         4650           4660           4670           4680
AAV2  ---------------------ATGGCGGGTTAATCATT
AAV4  GCGCTTGCGCTTCGCGGTTTACAACTGCCGGTTAATCAGT
AAV5  --------------------TTGCTTGAGAGTGTGG
BAAV  --------------------TTGCTAGAGAGTGTGG
      GCGCTTGCGCTTCGCGGTTTACAATTGCBDGWKARTSWGK
         4690           4700           4710           4720
AAV2  AACTACAAGGAACCCCTAGTGATGGAGTTGGCCACTCCCT
AAV4  AACTTCTGGCAAACCAGA-TGATGGAGTTGGCCACATTAG
AAV5  CACTCTCCCCCCTGTCGCGTTCGCTCGCTCGCTGGCTCGT
BAAV  CACTCTCCCCCCCTGTCGCGTTCGCTCGCTGCTGGCTCGA
      MACTHCHVSCMMHSYCGMGTKMKSKMGTTSGCYRSHTCVD
         4730           4740           4750           4760
AAV2  CTCTGCCGCTCGCTCGCTCACTGAGGCCGGGCGACCAAA
AAV4  CTATGCCGCTCGCTCACTCACTCGGCCCCTCGAGACAAA
AAV5  TTGGGGGCGGT--GCAGCTCA--AGAGCTGCCAGACGAC
BAAV  TTGGGGGCGGT--GCAGCTCA--AGAGCTGCCAGACGAC
      YTVKGSGSGYTCGSYMGCTCACTVAGVSCTGSCRRMCRAM
         4770           4780           4790           4800
AAV2  GGTCGCCCGACGCCCGGGCTTTGCCCGGGCGGCCTCAGTG
AAV4  GGTCTCCAGACTGCCGGCCTCTGGCCGGCAGGCCGGAGTG
AAV5  GGCCCCTCTGG---CCGTCGCCCCCCCAAAACGAGCC-AGCG
BAAV  GGCCCCTCTGG---CCGTCGCCCCCCAATCGAGCC-AGCG
      GGYCBYCHGRCKSCCGKCSYCYSCCCRR CGRGCCSAGYG
```

FIG.1A (CONTINUED)

```
              4810              4820              4830          4840
AAV2  A G C G A G C G A G C G C G C A G A G A G G G A G T G C C A A
AAV4  A G T G A G C G A G C G C G C A T A G A G G G A G T G C C A A
AAV5  A G C G A G C G A A C G C G A C A G G G G G G A G A T G C C A C
BAAV  A A C G A G C G A A C G C G A C A G G G G G G G A G T G C C A C
      A G C G A G C G A R C G C G M M D R G R G G G A G W G K S C M A C
```

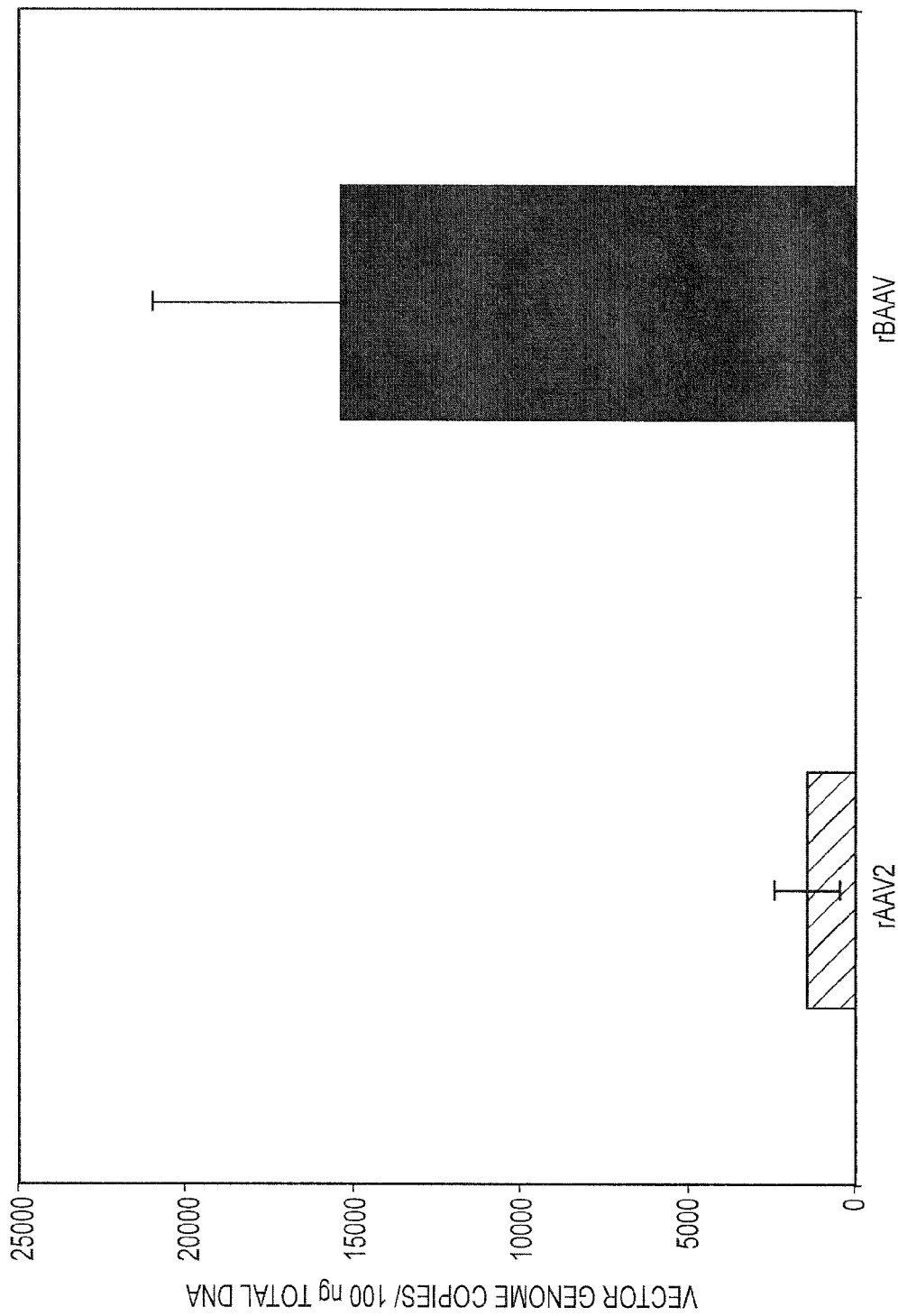

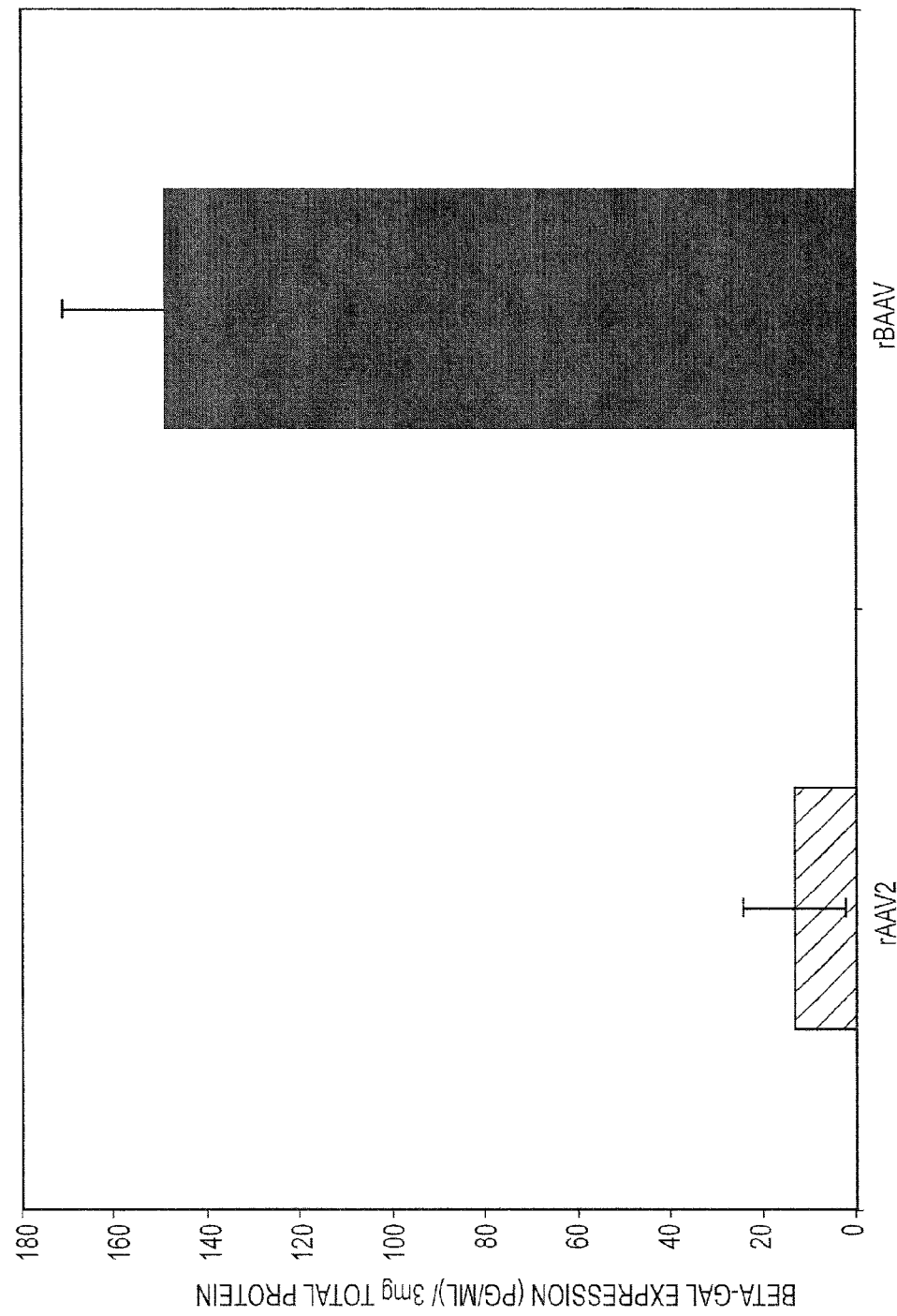

BOVINE ADENO-ASSOCIATED VIRAL (BAAV) VECTOR AND USES THEREOF

CROSS-REFERENCE TO RELATED APPLICATIONS

This application is a divisional of U.S. patent application Ser. No. 10/581,228, filed Oct. 26, 2006; which is a 371 national phase filing of PCT/US04/40825, filed Dec. 6, 2004; which claims the benefit of U.S. Provisional Application No. 60/526,786, filed Dec. 4, 2003 and U.S. Provisional Application No. 60/607,854 filed Sep. 8, 2004; all of which are entitled "Bovine Adeno-Associated Viral (BAAV) Vector and Uses Thereof" and hereby incorporated herein by reference in their entirety.

BACKGROUND OF THE INVENTION

1. Field of the Invention

The present invention provides bovine adeno-associated virus (BAAV) and vectors derived therefrom. Thus, the present invention relates to BAAV vectors for and methods of delivering nucleic acids to cells of subjects.

2. Background Art

Adeno-associated virus (AAV) is a member of the Parvoviridae, a virus family characterized by a single stranded linear DNA genome and a small icosahedral shaped capsid measuring about 20 nm in diameter. AAV was first described as a contamination of tissue culture grown simian virus 15, a simian adenovirus and was found dependent on adenovirus for measurable replication. This lead to its name, adeno-associated virus, and its classification in the genus Dependovirus (reviewed in Hoggan et al., 1970). AAV is a common contaminant of adenovirus samples and has been isolated from human virus samples (AAV2, AAV3, AAV5), from samples of simian virus-15 infected cells (AAV1, AAV4) as well as from stocks of avian (AAAV) (Bossis and Chiorini, 2003), bovine, canine and ovine adenovirus and laboratory adenovirus type 5 stock (AAV6). DNA spanning the entire rep-cap ORFs of AAV7 and AAV8 was amplified by PCR from heart tissue of rhesus monkeys (Gao et al., 2002).

With the exception of AAVs 1 and 6, all cloned AAV isolates appear to be serologically distinct. Nine isolates have been cloned, and recombinant viral stocks have been generated from each isolated virus.

AAV appears to commonly infect humans. 50%-80% of adults in North America are seropositive for AAV. A steep rise in antibody response against AAV1-3 was observed in the age group between 1-10 years (Blacklow et al., 1968). AAV2 and 3 were readily isolated from anal and throat specimens from children (Blacklow et al., 1967) whereas isolation from adults was not observed. It appears that AAV spreads primarily in the young population (Hoggan, 1970). Prevalence of antibodies against AAV was found to be similar in Europe, Brazil and Japan, which suggests a global spread of AAV (Erles et al., 1999). Infection with AAV appears to be benign in man and laboratory animals. Currently, no disease has been associated with AAV infections.

AAV2 is the best characterized adeno-associated virus and will be discussed as an AAV prototype. The AAV2 genome consists of a linear single stranded DNA of 4,780 nucleotides. Both polarities of DNA are encapsulated by AAV with equal efficiency. The AAV2 genome contains 2 open reading frames (ORF) named rep and cap. The rep ORF encodes the nonstructural proteins that are essential for viral DNA replication, packaging and AAV integration. The cap ORF encodes the capsid proteins. The rep ORF is transcribed from promoters at map units P5 and P19. The rep transcripts contain an intron close to the 3' end of the rep ORF and can be alternatively spliced. The rep ORF is therefore expressed as 4 partially overlapping proteins, which were termed according to their molecular weight Rep78, 68, 52 and 40. The cap ORF is expressed from a single promoter at P40. By alternative splicing and utilization of an alternative ACG start codon, cap is expressed into the capsid proteins VP1-3 which range in size from 65-86 kDa. VP3 is the most abundant capsid protein and constitutes 80% of the AAV2 capsid. All viral transcripts terminate at a polyA signal at map unit 96.

During a productive AAV2 infection, unspliced mRNAs from the p5 promoter encoding Rep78 are the first detectable viral transcripts. In the course of infection, expression from P5, P19 and P40 increase to 1:3:18 levels respectively. The levels of spliced transcripts increased to 50% for P5, P19 products and 90% of P40 expressed RNA (Mouw and Pintel, 2000).

The AAV2 genome is terminated on both sides by inverted terminal repeats (ITRs) of 145 nucleotides (nt). 125 nt of the ITR constitute a palindrome which contains 2 internal palindromes of 21 nt each. The ITR can fold back on itself to generate a T-shaped hairpin with only 7 non-paired bases. The stem of the ITR contains a Rep binding site (RBS) and a sequence that is site and strand specifically cleaved by Rep— the terminal resolution site (TRS). The ITR is essential for AAV2 genome replication, integration and contains the packaging signals.

The single-stranded AAV2 genome is packaged into a non-enveloped icosahedral shaped capsid of about 20-25 nm diameter. The virion consists of 26% DNA and 74% protein and has a density of 1.41 g/cm$^3$. AAV2 particles are extremely stable and can withstand heating to 60° C. for 1 hour, extreme ph, and extraction with organic solvents.

Rep proteins are involved in almost every step of AAV2 replication including AAV2 genome replication, integration, and packaging. Rep78 and Rep68 possess ATPase, 3'-5' helicase, ligase and nicking activities and bind specifically to DNA. Rep52 and Rep40 appear to be involved in the encapsidation process and encode ATPase and 3'-5' helicase activities. Mutational analysis suggests a domain structure for Rep78. The N-terminal 225 aa are involved in DNA binding, DNA nicking and ligation. Rep78 and Rep68 recognize a GCTC repeat motif in the ITR as well as in a linear truncated form of the ITR (Chiorini et al., 1994) with similar efficiencies. Rep78 and Rep68 possess a sequence and strand specific endonuclease activity, which cleaves the ITR at the terminal resolution site (TRS). Rep endonuclease activity is dependent on nucleoside triphosphate hydrolysis and presence of metal cations. Rep 78 and 68 can also bind and cleave single stranded DNA in a NTP independent matter. In addition, Rep78 catalyzes rejoining of single stranded DNA substrates originating from the AAV2 origin of replication—i.e., sequences containing a rep binding and terminal resolution element.

The central region of AAV2 Rep78, which represents the N-terminus of Rep52 and Rep40, contains the ATPase and 3'-5' helicase activities as well as nuclear localization signals. The helicase activity unwinds DNA-DNA and DNA-RNA duplexes, but not RNA-RNA. The ATPase activity is constitutive and independent of a DNA substrate. The C-terminus of Rep78 contains a potential zinc-finger domain and can inhibit the cellular serine/threonine kinase activity of PKA as well as its homolog PRKX by pseudosubstrate inhibition. Rep68 which is translated from a spliced mRNA that encodes the N-terminal 529 amino acids (aa) of Rep78 fused to 7 aa unique for Rep68, doesn't inhibit either PKA or PRKX. In addition to these biochemical activities, Rep can affect intracellular conditions by protein-protein interactions. Rep78 binds to a variety of cellular proteins including transcription factors like SP-1, high-mobility-group non-histone protein 1 (HMG-1) and the oncosuppressor p53. Overexpression of Rep results in pleiotrophic effects. Rep78 disrupts cell cycle progression and inhibits transformation by cellular and viral oncogenes. In susceptible cell lines, overexpression of Rep resulted in apoptosis and cell death. Several of Rep78 activities contribute to cytotoxicity, including its constitutive ATPase activity, interference with cellular gene expression and protein interactions.

The first step of an AAV infection is binding to the cell surface. Receptors and coreceptors for AAV2 include heparan sulfate proteoglycan, fibroblast growth factor receptor-1, and $\alpha_\nu\beta_5$ integrins whereas N-linked 2,3-linked sialic acid is required for AAV5 binding and transduction (Walters et al., 2001). In HeLa cells, fluorescently labeled AAV2 particles appear to enter the cell via receptor-mediated endocytosis in clathrin coated pits. More than 60% of bound virus was internalized within 10 min after infection. Labeled AAV particles are observed to have escaped from the endosome, been trafficked via the cytoplasm to the cell nucleus and accumulated perinuclear, before entering the nucleus, probably via nuclear pore complex (NPC). AAV2 particles have been detected in the nucleus, suggesting that uncoating takes place in the nucleus (Bartlett et al., 2000; Sanlioglu et al., 2000). AAV5 is internalized in HeLa cells predominantly by clathrin coated vesicles, but to a lesser degree also in noncoated pits. AAV particles can also be trafficked intercellularly via the Golgi apparatus (Bantel-Schaal et al., 2002). At least partial uncoating of AAV5 was suggested to take place before entering the nucleus since intact AAV5 particles could not be detected in the nucleus (Bantel-Schaal et al., 2002) After uncoating, the single stranded genome is converted into duplex DNA either by leading strand synthesis or annealing of input DNA of opposite polarity. AAV replication takes place within the nucleus.

During a co-infection with a helper virus such as Adenovirus, herpes simplex virus or cytomegalovirus, AAV is capable of an efficient productive replication. The helper functions provided by Adenovirus have been studied in great detail. In human embryonic kidney 293 cells, which constitutively express the Adenovirus E1A and E1B genes, the early Adenovirus gene products of E2A, E4 and VA were found sufficient to allow replication of recombinant AAV. Allen et al. reported that efficient production of rAAV is possible in 293 cells transfected with only an E4orf6 expression plasmid (Allen et al., 2000). E1A stimulates S phase entry and induces unscheduled DNA synthesis by inactivating the pRB checkpoint at the G1/S border by interaction with pRB family proteins which results in the release of E2F (reviewed in (Ben-Israel and Kleinberger, 2002). This leads to either induction or activation of enzymes involved in nucleotide synthesis and DNA replication. Since unscheduled DNA synthesis is a strong apoptotic signal, anti-apoptotic functions are required. E1B-19k is a Bcl-2 homolog and E1B-55k is a p53 antagonist. Both proteins have anti-apoptotic functions. E4orf6 forms a complex with E1B-55k and results in degradation of p53. It is also reported to cause S-phase arrest (Ben-Israel and Kleinberger, 2002). E2A encodes a single strand DNA binding protein, which appears to be non-essential for DNA replication but effects gene expression (Chang and Shenk, 1990) (Fields 39, 40). The VA transcription unit affects AAV2 RNA stability and translation (Janik et al., 1989). E1A has a more direct effect on AAV2 gene expression. The cellular transcription factor YY-1 binds and inhibits the viral P5 promoter. E1A relieves this transcriptional block. None of the late Ad gene products have been found to be essential for AAV2 replication. The main function of the helper virus appears to be the generation of a cellular environment with active DNA replication machinery and blocked pro-apoptotic functions that allows high-level AAV replication rather than a direct involvement in AAV replication.

While AAV is usually dependent on a helper virus for efficient replication, low level AAV replication was observed under conditions of genotoxic stress (Yakinoglu et al., 1988; Yakobson et al., 1989). AAV DNA replication and particle formation was also observed in differentiating keratinocytes in the absence of helper virus infection (Meyers et al., 2000). This demonstrates that AAV is not defective per se but rather depends on the helper virus to establish the favorable cellular condition and to provide factors for efficient replication The ability of AAV vectors to infect dividing and non-dividing cells, establish long-term transgene expression, and the lack of pathogenicity has made them attractive for use in gene therapy applications. Lack of cross competition in binding experiments suggests that each AAV serotype may have a distinct mechanism of cell entry. Comparison of the cap ORFs from different serotypes has identified blocks of conserved and divergent sequence, with most of the latter residing on the exterior of the virion, thus explaining the altered tissue tropism among serotypes (19-21, 48, 56). Vectors based on new AAV serotypes may have different host range and different immunological properties, thus allowing for more efficient transduction in certain cell types. In addition, characterization of new serotypes will aid in identifying viral elements required for altered tissue tropism.

Hearing and balance depend on the function of inner ear sensory epithelia, which consists of hair cells and a number of supporting cells that provide mechanical support for the sensory cells. The development of efficient transgene delivery for the inner ear is an important step towards potential application of gene-based therapies for cochlear disorders. Recently, a number of genes implicated in inherited peripheral hearing and vestibular disorders that affect specific cell types have been described. For example, a mutation of espin causes stereocilia degeneration (Naz, S., et al. J Med. Genet. 2004 August; 41(8):591-5), while mutations in connexins disrupt junctions between supporting cells (Kelsell, D. P., et al. Nature. 1997 May 1; 387(6628):80-3), these references herein incorporated by reference for the teaching of these mutations.

Some hereditary hearing loss disorders as well as progressive forms of deafness such as age-related hearing loss comprise excellent targets for gene therapy.

Currently, methods for introducing transgenes into neuroepithelial cells in the inner ear are unsatisfactory. Several gene transfer vectors including adeno-, lenti-, herpes simplex, and adenoassociated virus were characterized both in vivo and in vitro using cultured inner ear sensory epithelia explants. While promising, each system had limitations concerning transduction efficiency, tropism, or non-specific pathology induced by the vector (Holt 2002)(Derby, Sena-Esteves et al. 1999; Holt, Johns et al. 1999). Conventional transfection methods using cationic lipids, DEAE-Dextran or calcium phosphate or electroporation are not effective in inner ear epithelia and cause tissue degeneration. Transgenes may be introduced into sensory and nonsensory cells using a Gene Gun™, where plasmids precipitated on gold carriers are introduced into cells using high-pressure helium. While this approach offers the advantage of rapid and simultaneous gene expression in all transfected cells, and the ability to use easily manipulated plasmid DNA's, the extremely low yield of transfection as well as nonspecific structural damage to epithelia restricts its utility.

Provided is a vector comprising the BAAV virus or a vector comprising subparts of the virus, as well as BAAV viral particles. While BAAV is similar to AAV1-8, the viruses are found herein to be physically and genetically distinct. These differences endow BAAV with some unique properties and advantages, which better suit it as a vector for gene therapy or gene transfer applications.

As shown herein, BAAV capsid proteins are distinct from primate and avian AAV capsid proteins and BAAV exhibits a distinct cell tropism, thus making BAAV capsid-containing particles suitable for transducing cell types for which primate or avian recombinant AAV particles are unsuited or less well-suited. BAAV is serologically distinct from other AAVs and humans are not reported to have neutralizing antibodies against BAAV, thus in a gene therapy application, BAAV would allow for transduction of a patient who already possesses neutralizing antibodies to primate isolates either as a result of natural immunological defense or from prior exposure to other vectors. Thus, by providing these new recombinant vectors and particles based on BAAV, a new and highly useful series of vectors and methods of using them are provided.

SUMMARY OF THE INVENTION

A nucleic acid vector comprising a pair of bovine adeno-associated virus (BAAV) inverted terminal repeats and a promoter between the inverted terminal repeats is provided.

Further provided is a BAAV particle containing a vector comprising a pair of BAAV inverted terminal repeats.

Further provided is a BAAV particle containing a vector comprising a pair of AAV1 inverted terminal repeats.

Further provided is a BAAV particle containing a vector comprising a pair of AAV2 inverted terminal repeats.

Further provided is a BAAV particle containing a vector comprising a pair of AAV3 inverted terminal repeats.

Further provided is a BAAV particle containing a vector comprising a pair of AAV4 inverted terminal repeats.

Further provided is a BAAV particle containing a vector comprising a pair of AAV5 inverted terminal repeats.

Further provided is a BAAV particle containing a vector comprising a pair of AAV6 inverted terminal repeats.

Further provided is a BAAV particle containing a vector comprising a pair of AAV7 inverted terminal repeats.

Further provided is a BAAV particle containing a vector comprising a pair of AAV8 inverted terminal repeats.

Further provided is a BAAV particle containing a vector comprising a pair of AAAV inverted terminal repeats.

Further provided is a BAAV particle containing a vector comprising a pair of AAV5 inverted terminal repeats.

Further provided is an AAV1 particle containing a vector comprising a pair of BAAV inverted terminal repeats.

Further provided is an AAV2 particle containing a vector comprising a pair of BAAV inverted terminal repeats.

Further provided is an AAV3 particle containing a vector comprising a pair of BAAV inverted terminal repeats.

Further provided is an AAV4 particle containing a vector comprising a pair of BAAV inverted terminal repeats.

Further provided is an AAV5 particle containing a vector comprising a pair of BAAV inverted terminal repeats.

Further provided is an AAV6 particle containing a vector comprising a pair of BAAV inverted terminal repeats.

Further provided is an AAV7 particle containing a vector comprising a pair of BAAV inverted terminal repeats.

Further provided is an AAV8 particle containing a vector comprising a pair of BAAV inverted terminal repeats.

Further provided is an AAAV particle containing a vector comprising a pair of BAAV inverted terminal repeats.

Further provided is a dependovirus particle containing a vector comprising a pair of BAAV inverted terminal repeats.

Additionally, provided is an isolated nucleic acid comprising the nucleotide sequence set forth in SEQ ID NO:1 (BAAV genome). Furthermore, provided is an isolated nucleic acid consisting essentially of the nucleotide sequence set forth in SEQ ID NO:1 (BAAV genome).

Provided is an isolated nucleic acid encoding a BAAV Rep78 protein, for example, the nucleic acid as set forth in SEQ ID NO:2. Additionally provided is an isolated full-length BAAV Rep78 protein as set forth in SEQ ID NO:3 or a unique fragment thereof. Additionally provided is an isolated BAAV Rep 52 protein encoded by nucleic acid as set forth in SEQ ID NO:4 having the amino acid sequence set forth in SEQ ID NO:5, or a unique fragment thereof. The sequences for these proteins as well as the nucleotide sequence of the corresponding open reading frames are provided below in the Sequence Listing and elsewhere in the application where the proteins are described.

Further provided is an isolated BAAV capsid protein, VP1, encoded by nucleic acid as set forth in SEQ ID NO:6 having the amino acid sequence set forth in SEQ ID NO:7, or a unique fragment thereof. Additionally provided is an isolated BAAV capsid protein, VP2, encoded by nucleic acid as set forth in SEQ ID NO:8 having the amino acid sequence set forth in SEQ ID NO:9, or a unique fragment thereof. Also provided is an isolated BAAV capsid protein, VP3, encoded by nucleic acid as set forth in SEQ ID NO:10 having the amino acid sequence set forth in SEQ ID NO:11, or a unique fragment thereof.

Additionally provided is an isolated nucleic acid comprising a BAAV p5 promoter having the nucleic acid sequence set forth in SEQ ID NO: 15, or a unique fragment thereof.

Provided is a method of screening a cell for infectivity by BAAV comprising contacting the cell with BAAV and detecting the presence of BAAV in the cells.

Further provided is a method of delivering a nucleic acid to a cell comprising administering to the cell a BAAV particle containing a vector comprising the nucleic acid inserted between a pair of AAV inverted terminal repeats, thereby delivering the nucleic acid to the cell.

Further provided is a method of delivering a nucleic acid to a subject comprising administering to a cell from the subject a BAAV particle comprising the nucleic acid inserted between a pair of AAV inverted terminal repeats, and returning the cell to the subject, thereby delivering the nucleic acid to the subject.

Further provided is a method of delivering a nucleic acid to a cell in a subject comprising administering to the subject a BAAV particle comprising the nucleic acid inserted between a pair of AAV inverted terminal repeats, thereby delivering the nucleic acid to a cell in the subject.

Further provided is a method of delivering a nucleic acid to a cell in a subject having antibodies to other serotypes of AAV comprising administering to the subject a BAAV particle comprising the nucleic acid, thereby delivering the nucleic acid to a cell in the subject.

Further provided is a BAAV particle comprising a capsid protein consisting essentially of the amino acid sequence set forth in SEQ ID NO:7, or a unique fragment thereof. Further provided is a BAAV particle comprising a capsid protein consisting essentially of the amino acid sequence set forth in SEQ ID NO:9, or a unique fragment thereof. Further provided is a BAAV particle comprising a capsid protein consisting essentially of the amino acid sequence set forth in SEQ ID NO:11, or a unique fragment thereof.

Additionally provided is an isolated nucleic acid comprising a BAAV p5 promoter having the nucleic acid sequence set forth in SEQ ID NO:15, or a unique fragment thereof.

Provided is a method of screening a cell for infectivity by BAAV, comprising contacting the cell with BAAV and detecting the presence of BAAV in the cells.

Further provided is a method of delivering a nucleic acid to a cell comprising administering to the cell a BAAV particle containing a vector comprising the nucleic acid inserted between a pair of AAV inverted terminal repeats, thereby delivering the nucleic acid to the cell.

Further provided is a method of delivering a nucleic acid to a subject comprising administering to a cell from the subject a BAAV particle comprising the nucleic acid inserted between a pair of BAAV inverted terminal repeats, and returning the cell to the subject, thereby delivering the nucleic acid to the subject.

Further provided is a method of delivering a nucleic acid to a cell in a subject comprising administering to the subject a BAAV particle comprising the nucleic acid inserted between a pair of BAAV inverted terminal repeats, thereby delivering the nucleic acid to a cell in the subject.

Further provided is a method of delivering a nucleic acid to a cell in a subject having antibodies to primate AAVs comprising administering to the subject a BAAV particle comprising the nucleic acid, thereby delivering the nucleic acid to a cell in the subject.

Provided is a vector system for producing infectious virus particles having a characteristic of BAAV comprising: at least one vector comprising a nucleic acid selected from the group consisting of a pair of BAAV inverted terminal repeats, a nucleic acid encoding a BAAV capsid protein, and a nucleic acid encoding a BAAV Rep protein.

BRIEF DESCRIPTION OF THE DRAWINGS

FIG. 6 is a comparison of rAAV2 and rBAAV transduction of salivary glands. $10^{10}$ particles of AAV2-RnlacZ and BAAV-RnlacZ were injected into submandibular glands of BALB/c mice by retrograde ductal instillation. 4 weeks after infection, glands were removed and analyzed for the presence of vector genome DNA by real time PCR (A) and expression of beta-gal by an ELISA (B). Values given are means of data from 7 animals, error bars represent standard deviation.

DETAILED DESCRIPTION OF THE INVENTION

Figure 1B:
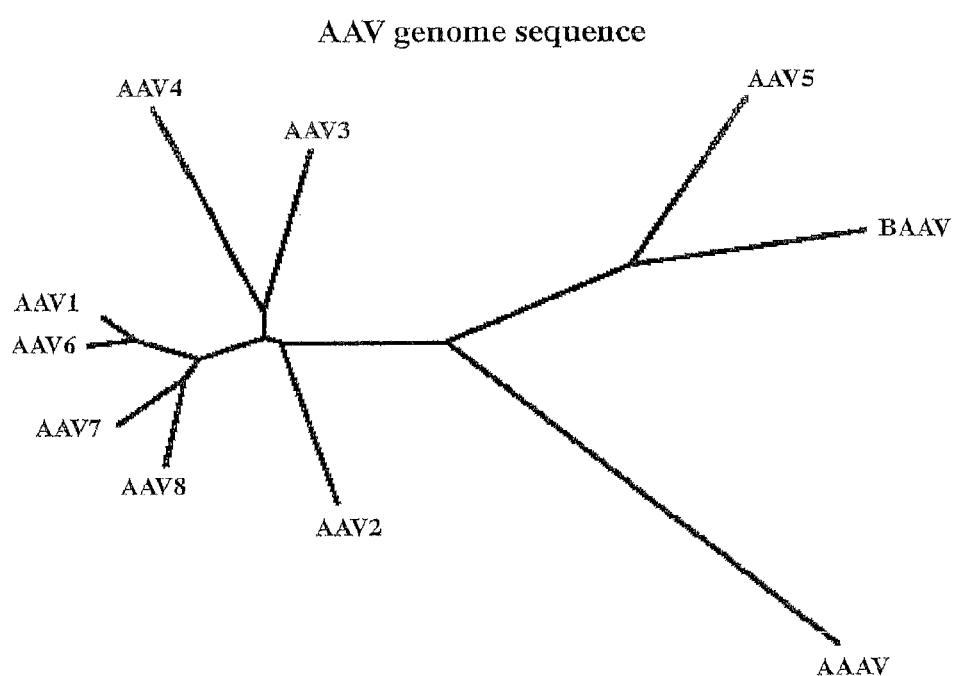
FIG. 1 shows an example of the BAAV genome. (A) The genomes of BAAV (SEQ ID NO:1), AAV2 (SEQ ID NO:26), AAV4 (SEQ ID NO:27), and AAV5 (SEQ ID NO:28), were aligned using MACVECTORT™ (Oxford Molecular). Nucleotides identical in at least 2 AAV serotypes are displayed boxed and shaded. (B) Phylogenetic relationship of BAAV to other serotypes is illustrated by an unrooted tree diagram.

As used in the specification and in the claims, "a" can mean one or more, depending upon the context in which it is used. The terms "having" and "comprising" are used interchangeably herein, and signify open ended meaning.

The present application provides a recombinant bovine adeno-associated virus (BAAV). The application provides the isolation, subcloning, and sequencing of BAAV. This virus has one or more of the characteristics described below. The compositions provided herein do not include wild-type BAAV. The methods provided herein can use either wild-type BAAV or recombinant BAAV-based delivery.

Provided herein are recombinant BAAV particles, recombinant BAAV vectors and recombinant BAAV virions. As used herein, "recombinant" refers to nucleic acids, vectors, polypeptides, or proteins that have been generated using DNA recombination (cloning) methods and are distinguishable from native or wild-type nucleic acids, vectors, polypeptides, or proteins. A BAAV particle is a viral particle comprising a BAAV capsid protein. A recombinant BAAV vector is a nucleic acid construct that comprises at least one unique, isolated nucleic acid of BAAV. The recombinant BAAV vector can further comprise at least one non-BAAV nucleic acid. As used herein, a "virion" refers to an infectious virus particle, and "infectious" refers to the ability of a virion to deliver genetic material to a cell. Thus, a recombinant BAAV virion is a particle containing a recombinant BAAV vector, wherein the particle can be either a BAAV particle as described herein or a non-BAAV particle. Alternatively, a recombinant BAAV virion can be a BAAV particle containing a recombinant vector, wherein the vector can be either a BAAV vector as described herein or a non-BAAV vector. A BAAV particle can further be an "empty particle", wherein the particle does not contain a nucleic acid, vector or plasmid, and is therefore not infectious. These vectors, particles, virions, nucleic acids and polypeptides are described below.

Provided herein is the nucleotide sequence of the BAAV genome and vectors and particles derived there from. Specifically, provided herein is a nucleic acid vector, comprising a pair of BAAV inverted terminal repeats (ITRs) and a promoter between the inverted terminal repeats. The rep proteins of AAV5 and BAAV will bind to the BAAV ITR and it can function as an origin of replication for packaging of recombinant AAV particles. The minimum sequence necessary for this activity is the TRS site where Rep cleaves in order to replicate the virus. Minor modifications in an ITR are contemplated and are those that will not interfere with the hairpin structure formed by the ITR as described herein and known in the art. Furthermore, to be considered within the term it must retain the Rep binding site described herein.

The D-region of the AAV2 ITR, a single stranded region of the ITR, inboard of the TRS site, has been shown to bind a factor which depending on its phosphorylation state correlates with the conversion of the AAV from a single stranded genome to a transcriptionally active form that allows for expression of the viral DNA. This region is conserved between AAV2, 3, 4, and 6 but is divergent in AAV5 and BAAV (SEQ ID NO: 13). The D+ region is the reverse complement of the D− region.

The promoter can be any desired promoter, selected by known considerations, such as the level of expression of a nucleic acid functionally linked to the promoter and the cell type in which the vector is to be used. That is, the promoter can be tissue/cell-specific. Promoters can be prokaryotic, eukaryotic, fungal, nuclear, mitochondrial, viral or plant promoters. Promoters can be exogenous or endogenous to the cell type being transduced by the vector. Promoters can include, for example, bacterial promoters, known strong promoters such as SV40 or the inducible metallothionein promoter, or an AAV promoter, such as an AAV p5 promoter. Additionally, chimeric regulatory promoters for targeted gene expression can be utilized. Examples of these regulatory systems, which are known in the art, include the tetracycline based regulatory system which utilizes the tet transactivator protein (tTA), a chimeric protein containing the VP 16 activation domain fused to the tet repressor of *Escherichia coli*, the IPTG based regulatory system, the CID based regulatory system, and the Ecdysone based regulatory system (No, D., et al., Proc Natl Acad Sci USA. 93(8):3346-3351 (1996)).

Other promoters include promoters derived from actin genes, immunoglobulin genes, cytomegalovirus (CMV), adenovirus, bovine papilloma virus, adenoviral promoters, such as the adenoviral major late promoter, an inducible heat shock promoter, respiratory syncytial virus, Rous sarcomas virus (RSV), etc., specifically, the promoter can be AAV2 p5 promoter or AAV5 p5 promoter or BAAV p5 promoter. More specifically, the BAAV p5 promoter can be in about the same location in SEQ ID NO: 1 as the AAV2 p5 promoter, in the corresponding AAV2 published sequence. Additionally, the p5 promoter may be enhanced by nucleotides 1-173 of SEQ ID NO:1. Furthermore, smaller fragments of p5 promoter that retain promoter activity can readily be determined by standard procedures including, for example, constructing a series of deletions in the p5 promoter, linking the deletion to a reporter gene, and determining whether the reporter gene is expressed, i.e., transcribed and/or translated. The promoter can be the promoter of any of the AAV serotypes, and can be the p19 promoter (SEQ ID NO: 16) or the p40 promoter set forth in the sequence listing as SEQ ID NO: 17.

It should be recognized that any errors in any of the nucleotide sequences disclosed herein can be corrected, for example, by using the hybridization procedure described below with various probes derived from the described sequences such that the coding sequence can be re-isolated and re-sequenced. Rapid screening for point mutations can also be achieved with the use of polymerase chain reaction-single strand conformation polymorphism (PCR-SSCP). The corresponding amino acid sequence can then be corrected accordingly.

The BAAV-derived vector provided herein can further comprise an exogenous nucleic acid functionally linked to the promoter. By "exogenous" nucleic acid is meant any nucleic acid that is not normally found in wild-type BAAV that can be inserted into a vector for transfer into a cell, tissue or organism. The exogenous nucleic acid can be a nucleic acid not normally found in the target cell, or it can be an extra copy or copies of a nucleic acid normally found in the target cell. The terms "exogenous" and "heterologous" are used herein interchangeably.

By "functionally linked" is meant that the promoter can promote expression of the exogenous nucleic acid, as is known in the art, and can include the appropriate orientation of the promoter relative to the exogenous nucleic acid. Furthermore, the exogenous nucleic acid preferably has all appropriate sequences for expression of the nucleic acid. The nucleic acid can include, for example, expression control sequences, such as an enhancer, and necessary information processing sites, such as ribosome binding sites, RNA splice sites, polyadenylation sites, and transcriptional terminator sequences.

The exogenous nucleic acid can encode beneficial proteins or polypeptides that replace missing or defective proteins required by the cell or subject into which the vector is transferred or can encode a cytotoxic polypeptide that can be directed, e.g., to cancer cells or other cells whose death would be beneficial to the subject. The exogenous nucleic acid can also encode antisense RNAs that can bind to, and thereby inactivate, mRNAs made by the subject that encode harmful proteins. The exogenous nucleic acid can also encode ribozymes that can effect the sequence-specific inhibition of gene expression by the cleavage of mRNAs. In one aspect, antisense polynucleotides can be produced from an exogenous expression cassette in an AAV5 vector construct where the expression cassette contains a sequence that promotes cell-type specific expression (Wirak et al., *EMBO* 10:289 (1991)). For general methods relating to antisense polynucleotides, see *Antisense RNA and DNA*, D. A. Melton, Ed., Cold Spring Harbor Laboratory, Cold Spring Harbor, N.Y. (1988).

Examples of exogenous nucleic acids which can be administered to a cell or subject as part of the present BAAV vector can include, but are not limited to the following: nucleic acids encoding secretory and nonsecretory proteins, nucleic acids encoding therapeutic agents, such as tumor necrosis factors (TNF), such as TNF-α; interferons, such as interferon-α, interferon-β, and interferon-γ; interleukins, such as IL-1, IL-1β, and ILs-2 through -14; GM-CSF; adenosine deaminase; cellular growth factors, such as lymphokines; soluble CD4; Factor VIII; Factor IX; T-cell receptors; LDL receptor; ApoE; ApoC; alpha-1 antitrypsin; ornithine transcarbamylase (OTC); cystic fibrosis transmembrane receptor (CFTR); insulin; Fc receptors for antigen binding domains of antibodies, such as immunoglobulins; anti-HIV decoy tar elements; and antisense sequences which inhibit viral replication, such as antisense sequences which inhibit replication of hepatitis B or hepatitis non-A, non-B virus. The nucleic acid is chosen considering several factors, including the cell to be transfected. Where the target cell is a blood cell, for example, particularly useful nucleic acids to use are those which allow the blood cells to exert a therapeutic effect, such as a gene encoding a clotting factor for use in treatment of hemophilia. Another target cell is the lung airway cell, which can be used to administer nucleic acids, such as those coding for the cystic fibrosis transmembrane receptor, which could provide a gene therapeutic treatment for cystic fibrosis. Other target cells include muscle cells where useful nucleic acids, such as those encoding cytokines and growth factors, can be transduced and the protein the nucleic acid encodes can be expressed and secreted to exert its effects on other cells, tissues and organs, such as the liver. Furthermore, the nucleic acid can encode more than one gene product, limited only, if the nucleic acid is to be packaged in a capsid, by the size of nucleic acid that can be packaged.

Furthermore, suitable nucleic acids can include those that, when transferred into a primary cell, such as a blood cell, cause the transferred cell to target a site in the body where that cell's presence would be beneficial. For example, blood cells such as TIL cells can be modified, such as by transfer into the cell of a Fab portion of a monoclonal antibody, to recognize a selected antigen. Another example would be to introduce a nucleic acid that would target a therapeutic blood cell to tumor cells. Nucleic acids useful in treating cancer cells include those encoding chemotactic factors which cause an inflammatory response at a specific site, thereby having a therapeutic effect.

Cells, particularly blood cells, muscle cells, airway epithelial cells, brain cells and endothelial cells having such nucleic acids transferred into them can be useful in a variety of diseases, syndromes and conditions. For example, suitable nucleic acids include nucleic acids encoding soluble CD4, used in the treatment of AIDS and α-antitrypsin, used in the treatment of emphysema caused by α-antitrypsin deficiency. Other diseases, syndromes and conditions in which such cells can be useful include, for example, adenosine deaminase deficiency, sickle cell deficiency, brain disorders such as Alzheimer's disease, thalassemia, hemophilia, diabetes, phenylketonuria, growth disorders and heart diseases, such as those caused by alterations in cholesterol metabolism, and defects of the immune system.

Other cells in which a gene of interest can be expressed include, but are not limited to, fibroblasts, neurons, retinal cells, kidney cells, lung cells, bone marrow stem cells, hematopoietic stem cells, retinal cells and neurons. The cells in which the gene of interest can be expressed can be dividing cells such as MDCK cells, BHK cells, HeLa cells, 3T3 cells, CV1 cells, COS7 cells, HOS cells and 293 cells. The cells can also be embryonic stem cells of mouse, rhesus, human, bovine or sheep origin, as well as stem cells of neural, hematopoietic, muscle, cardiac, immune or other origin. Non-dividing cells can also be contacted with a particle provided herein to express a gene of interest. Such cells include, but are not limited to hematopoietic stem cells and embryonic stem cells that have been rendered non-dividing.

As another example, hepatocytes can be transfected with the present vectors having useful nucleic acids to treat liver disease. For example, a nucleic acid encoding OTC can be used to transfect hepatocytes (ex vivo and returned to the liver or in vivo) to treat congenital hyperammonemia, caused by an inherited deficiency in OTC. Another example is to use a nucleic acid encoding LDL to target hepatocytes ex vivo or in vivo to treat inherited LDL receptor deficiency. Such transfected hepatocytes can also be used to treat acquired infectious diseases, such as diseases resulting from a viral infection. For example, transduced hepatocyte precursors can be used to treat viral hepatitis, such as hepatitis B and non-A, non-B hepatitis, for example by transducing the hepatocyte precursor with a nucleic acid encoding an antisense RNA that inhibits viral replication. Another example includes transferring a vector provided herein having a nucleic acid encoding a protein, such as γ-interferon, which can confer resistance to the hepatitis virus.

For a procedure using transfected hepatocytes or hepatocyte precursors, hepatocyte precursors having a vector provided herein transferred in can be grown in tissue culture, removed from the tissue culture vessel, and introduced to the body, such as by a surgical method. In this example, the tissue would be placed directly into the liver, or into the body cavity in proximity to the liver, as in a transplant or graft. Alternatively, the cells can simply be directly injected into the liver, into the portal circulatory system, or into the spleen, from which the cells can be transported to the liver via the circulatory system. Furthermore, the cells can be attached to a support, such as microcarrier beads, which can then be introduced, such as by injection, into the peritoneal cavity. Once the cells are in the liver, by whatever means, the cells can then express the nucleic acid and/or differentiate into mature hepatocytes which can express the nucleic acid.

The provided viral particles can be administered to cells, as described herein, with a Multiplicity of Infection (MOI) of 10. The MOI is the ratio of infectious virus particles to the number of cells being infected. Thus, an MOI of 0.1 results in the average inoculation of 1 virus particle for every 10 cells. The general theory behind MOI is to introduce one infectious virus particle to every host cell that is present in the culture. However, more than one virus may infect the same cell which leaves a percentage of cells uninfected. This occurrence can be reduced by using a higher MOI to ensure that every cell is infected. The provided viral particles can therefore be administered to cells, as described herein, with a MOI of 0.01 to 100, such as for example 1, 2, 3, 4, 5, 6, 7, 8, 9, 10, 11, 12, 13, 14, 15, 16, 17, 18, 19, 20, 30, 40, 50, 60, 70, 80, 90, 100.

The BAAV-derived vector can include any normally occurring BAAV nucleic acid sequences in addition to an ITR and promoter. The BAAV-derived vector can also include sequences that are at least 60%, 70%, 80%, 90%, 95%, 96%, 97%, 98%, or 99% identical to the BAAV nucleic acids set forth herein. Examples of vector constructs are provided below.

The present vector or BAAV particle or recombinant BAAV virion can utilize any unique fragment of these present BAAV nucleic acids, including the BAAV nucleic acids set forth in SEQ ID NOS: 1, 2, 4, 6, 8, 10 and 12-17. A unique fragment consists of a sequence that is not present anywhere else on a genome. To be unique, the fragment must be of sufficient size to distinguish it from other known sequences, which is most readily determined by comparing any nucleic acid fragment to the nucleotide sequences of nucleic acids in computer databases, such as GenBank. Such comparative searches are standard in the art. Typically, a unique fragment useful as a primer or probe will be at least about 8 or 10, preferable at least 20 or 25 nucleotides in length, depending upon the specific nucleotide content of the sequence. Additionally, fragments can be, for example, at least about 30, 40, 50, 75, 100, 200 or 500 nucleotides in length and can encode polypeptides or be probes. The nucleic acid can be single or double stranded, depending upon the purpose for which it is intended. Where desired, the nucleic acid can be RNA.

It is understood that as discussed herein the use of the terms "homology" and "identity" mean the same thing as similarity. Thus, for example, if the use of the word homology is used to refer to two non-natural sequences, it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related.

In general, it is understood that one way to define any known variants and derivatives or those that might arise, of the disclosed nucleic acids and polypeptides herein, is through defining the variants and derivatives in terms of homology to specific known sequences. In general, variants of nucleic acids and polypeptides herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two polypeptides or nucleic acids. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.; the BLAST algorithm of Tatusova and Madden FEMS Microbiol. Lett. 174: 247-250 (1999) available from the National Center for Biotechnology Information (http://www.ncbi.nlm.nih.gov/blast/b12seq/b12.html), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989, which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

Further provided herein is a BAAV capsid protein that can combine with other capsid proteins to form a BAAV particle to contain the disclosed vectors. Also provided herein is a BAAV particle, comprising a BAAV capsid protein. The capsid protein can be selected from a group consisting of VP1, VP2 and VP3. The capsid protein of the BAAV particle can have the amino acid sequences of SEQ ID NOS: 7, 9, or 11. The capsid protein of the BAAV particle can be encoded by the nucleic acid sequences of SEQ ID NOS: 6, 8, or 10. For example, provided is a BAAV particle, comprising all three BAAV capsid proteins, i.e., VP1, VP2 and VP3, SEQ ID NOS: 7, 9, and 11, respectively. Also provided is a BAAV particle, comprising each BAAV capsid protein individually or in combination. Also provided is a particle comprising VP1 and VP3 capsid proteins, i.e., lacking any VP2 capsid proteins. Thus, a BAAV particle comprising a BAAV capsid protein comprises at least one BAAV capsid protein (VP1, VP2 or VP3) or a funtional fragment thereof. One of skill in the art understands that it is the non-conserved amino acids, as demonstrated in FIG. 3, that are contributing to the properties of BAAV that make it distinct from the other serotypes. Provided therefore is a capsid protein comprising a mutation, deletion or substitution in the conserved regions, including, for example, a substitution with a homologous region from another AAV serotype.

A BAAV particle comprising a BAAV capsid protein can be utilized to deliver a nucleic acid vector to a cell, tissue or subject. For example, the herein described BAAV vectors can be encapsidated in a BAAV capsid-derived particle and utilized in a gene delivery method. Furthermore, other viral nucleic acids can be encapsidated in the BAAV particle and utilized in such delivery methods. For example, an AAV1-8 or AAAV vector (e.g. AAV1-8 or AAAV ITR and nucleic acid of interest) can be encapsidated in a BAAV particle and administered. Furthermore, a BAAV chimeric capsid incorporating AAV1-8 or AAAV capsid sequences and BAAV capsid sequences can be generated, by standard cloning methods, selecting regions from the known sequences of each protein as desired. For example, particularly antigenic regions of the BAAV capsid protein can be replaced with the corresponding region of the AAV2 capsid protein. In addition to chimeric capsids incorporating AAV2 capsid sequences, chimeric capsids incorporating AAV1, 3-8, and AAV5 capsid sequences can be generated, by standard cloning methods, selecting regions from the known sequences of each protein as desired. Alternatively a chimeric capsid can be made by the addition of a plasmid that expresses AAV1-8 capsid proteins at a ratio with the BAAV capsid expression plasmid that allows only a few capsid proteins to be incorporated into the BAAV particle. Thus, for example, a chimeric particle may be constructed that contains 6 AAV2 capsid proteins and 54 BAAV capsid proteins if the complete capsid contains 60 capsid proteins. Methods for generating chimeric AAVs are known in the art and can be found in Rabinowitz J E, et al. J. Virol. 2004 May; 78(9):4421-32, herein incorporated by reference for these methods. Examples of chimeric capsids would be to combine the VP1, 2, 3 proteins of BAAV and the VP1, 2, 3 proteins of AAV5 such that a new tropism would arise. An example would be a vector that could both transduce and have transcytosis activity in Caco-2 cells or a vector that could transduce a cell that was not previously permissive for either BAAV or AAV5.

The capsids can also be modified to alter their specific tropism by genetically altering the capsid to encode a specific ligand to a cell surface receptor.

Alternatively, the capsid can be chemically modified by conjugating a ligand to a cell surface receptor. By genetically or chemically altering the capsids, the tropism can be modified to direct BAAV to a particular cell or population of cells. The capsids can also be altered immunologically by conjugating the capsid to an antibody that recognizes a specific protein on the target cell or population of cells.

Provided are two regions in the capsid of BAAV that are on the virus surface and could tolerate substitution. These two regions are aa 257-264 (GSSNASDT SEQ ID NO:18) and aa 444-457 (TTSGGTLNQGNSAT SEQ ID NO:19). Other regions of the BAAV capsid could also accommodate the substitution of amino acids that would allow for epitope presentation on the surface of the virus. All of these regions would have surface exposure and the ability to support a substitution of sequence to insert the epitope while still allowing for capsid assembly. The substitutions can include non-BAAV epitopes and non-BAAV ligands.

Because of the symmetry of the AAV particles, a substitution in one subunit of the capsid will appear multiple times on the capsid surface. For example the capsid is made of approximately 50 VP3 proteins, 5 VP1 and 5 VP2. Therefore an epitope incorporated in the VP3 protein could be expressed 55 times on the surface of each particle increasing the likelihood of the epitope forming a stable interaction with its target. In some cases this may be too high of a ligand density for functional binding or this high density of epitope may interfere with capsid formation. The epitope density could be lowered by introducing another plasmid into the packaging system for production of recombinant particles and the ratio between the packaging plasmid with the modified VP3 protein and the wt VP3 protein altered to balance the epitope density on the virus surface. Thus, the ratio between the modified VP3 and the wt VP3 can be 0:50 to 50:0, including, for example, 1:49, 2:48, 3:47, 4:46, 5:45, 6:44, 7:43, 8:42, 9:41, 10:40, 11:39, 12:38, 13:37, 14:36, 15:35, 16:34, 17:33, 18:32, 19:31, 20:30, 21:29, 22:28, 23:27, 24:27, 25:25, 26:24, 27:23, 28:22, 29:21, 30:20, 31:19, 32:18, 33:17, 34:16, 35:15, 36:14, 37:13, 38:12, 39:11, 40:10, 41:9, 42:8, 43:7, 44:6, 45:5, 46:4, 47:3, 48:2, or 49:1.

Epitopes could be incorporated into the virus capsid for the purpose of 1) altering the tropism of the virus 2) blocking an immune response directed at the virus 3) developing a host immune response to the epitope for the purpose of vaccination. Examples of epitopes that could be added to BAAV capsids include but are not limited to:
LH receptor binding epitope
RGD integrin binding epitope
CD13 binding epitope NGRAHA SEQ ID NO:20

The Retanef polyprotein vaccine candidate for HIV-1
single chain antibody fragments directed against tumor cells
Endothelial cell binding epitope SIGYPLP SEQ ID NO:21
serpin receptor ligand, KFNKPFVFLI SEQ ID NO:22
protective B-cell epitope hemagglutinin (HA) 91-108 from influenza HA
NDV B-cell immunodominant epitope (IDE) spanning residues 447 to 455
Major immunogenic epitope for parvovirus B19 (NISLDN-PLENPSSLFDLVARIK SEQ ID NO:23) that can elicit protective antibody titers.

The capsids can also be assembled into empty particles by expression in mammalian, bacterial, fungal or insect cells. For example, AAV2 particles are known to be made from VP3 and VP2 capsid proteins in baculovirus. The same basic protocol can produce an empty BAAV particle comprising BAAV capsid proteins and also full particles. The empty BAAV particles can be used to deliver, for example, antigens, drugs, proteins, or metals to cells or cells in a subject. Antigens can be directly incorporated into the capsid of an empty BAAV particle. An antigen can further be coupled via an antibody-antigen complex to the empty particle. Also disclosed is the coupling of drugs, proteins, or metals on the inside of the empty particles.

The herein described recombinant BAAV nucleic acid derived vector can be encapsidated in a viral particle. The viral particle can be a parvovirus particle. The parvovirus particle can be a dependovirus particle. The viral particle can be an AAV particle. In particular, the recombinant BAAV nucleic acid derived vector can be encapsidated in a BAAV, AAV1, AAV2, AAV3, AAV4, AAV5, AAV6, AAV7, AAV8, or AAAV particle, a particle comprising a portion of any of these capsids, or a chimeric capsid particle as described above, by standard methods using the appropriate capsid proteins in the encapsidation process, as long as the nucleic acid vector fits within the size limitation of the particle utilized. The encapsidation process itself is standard in the art. The BAAV replication machinery, i.e. the rep initiator proteins and other functions required for replication, can be utilized to produce the BAAV genome that can be packaged in an AAV1-8 or AAAV capsid.

The recombinant BAAV virion containing a vector can also be produced by recombinant methods utilizing multiple plasmids. In one example, the BAAV rep nucleic acid would be cloned into one plasmid, the BAAV ITR nucleic acid would be cloned into another plasmid and the AAV1-8 capsid nucleic acid would be cloned on another plasmid. These plasmids would then be introduced into cells. The cells that were efficiently transduced by all three plasmids, would exhibit specific integration as well as the ability to produce BAAV recombinant virus. Additionally, two plasmids could be used where the BAAV rep nucleic acid would be cloned into one plasmid and the BAAV ITR and BAAV capsid would be cloned into another plasmid. These plasmids would then be introduced into cells. The cells that were efficiently transduced by both plasmids, would exhibit specific integration as well as the ability to produce BAAV recombinant virus.

A BAAV capsid composed of VP1, VP2, and VP3 polypeptide can overall have greater than 56% homology to the polypeptide having the amino acid sequence encoded by nucleotides in SEQ ID NOS:6, 8 and 10.

The capsid protein can have about 70% homology, about 75% homology, 80% homology, 85% homology, 90% homology, 95% homology, 98% homology, 99% homology, or even 100% homology to the protein having the amino acid sequence encoded by the nucleotides set forth in SEQ ID NOS:6, 8 or 10. The percent homology used to identify proteins herein, can be based on a nucleotide-by-nucleotide comparison or more preferable is based on a computerized algorithm as described herein. Variations in the amino acid sequence of the BAAV capsid protein are contemplated herein, as long as the resulting particle comprising a BAAV capsid protein remains antigenically or immunologically distinct from AAV1-8 or AAAV capsid, as can be routinely determined by standard methods. Specifically, for example, ELISA and Western blots can be used to determine whether a viral particle is antigenically or immunologically distinct from AAV2 or the other serotypes. Furthermore, the BAAV particle preferably retains tissue tropism distinction from other AAVs, such as that exemplified in the examples herein. A BAAV chimeric particle comprising at least one BAAV coat protein may have a different tissue tropism from that of a BAAV particle consisting only of BAAV coat proteins, but is still distinct from the tropism of an AAV2 particle.

Provided herein is a recombinant BAAV virion, comprising a BAAV particle containing, i.e., encapsidating, a vector comprising a pair of AAV1, AAV2, AAV3, AAV4, AAV5, AAV6, AAV7, AAV8, AAAV, or BAAV inverted terminal repeats. The recombinant vector can further comprise a BAAV Rep-encoding nucleic acid. The vector encapsidated in the particle can further comprise an exogenous nucleic acid inserted between the inverted terminal repeats.

Further contemplated are chimeric recombinant ITRs that contain a rep binding site and a TRS site recognized by that Rep protein. By "Rep protein" is meant one or more of the Rep proteins, Rep 40, Rep 78, Rep 52, Rep 68. Alternatively, "Rep protein" could be all four of the Rep proteins described herein. One example of a chimeric ITR would consist of a BAAV D region (SEQ ID NO: 13), a BAAV TRS site (SEQ ID NO: 14), an AAV2 hairpin and an AAV2 Rep binding site. Another example would be a BAAV D region, a BAAV TRS site, an AAV3 hairpin and an AAV3 Rep binding site. In these chimeric ITRs, the D region can be from AAV1-8 or AAAV. The hairpin can be derived from AAV1-8 or AAAV. The binding site can be derived from any of AAV1-8 or AAAV. Preferably, the D region and the TRS are from the same serotype.

The chimeric ITRs can be combined with BAAV Rep protein and any of the AAV serotype capsids to obtain a recombinant virion. For example, a recombinant virion can be produced by a BAAV D region, a BAAV TRS site, an AAV2 hairpin, an AAV2 binding site, BAAV Rep protein and AAV1 capsid. This recombinant virion would possess the cellular tropism conferred by the AAV1 capsid protein and would possess the efficient replication conferred by the BAAV Rep.

Other examples of the combinations of ITR, Rep protein and Capsids that will produce recombinant virus include but are not limited to:
BAAV ITR+BAAV Rep+BAAV Cap=virus
AAV5 ITR+BAAV Rep+BAAV Cap=virus
AAV5 ITR+BAAV Rep+AAV1 Cap=virus
AAV5 ITR+BAAV Rep+AAV2 Cap=virus
AAV5 ITR+BAAV Rep+AAV3 Cap=virus
AAV5 ITR+BAAV Rep+AAV4 Cap=virus
AAV5 ITR+BAAV Rep+AAV5 Cap=virus
AAV5 ITR+BAAV Rep+AAV6 Cap=virus
AAV5 ITR+BAAV Rep+AAV7 Cap=virus
AAV5 ITR+BAAV Rep+AAV8 Cap=virus
AAV5 ITR+BAAV Rep+AAAV Cap=virus
BAAV ITR+AAV5 Rep+BAAV Cap=virus
BAAV ITR+AAV5 Rep+AAV1 Cap=virus
BAAV ITR+AAV5 Rep+AAV2 Cap=virus
BAAV ITR+AAV5 Rep+AAV3 Cap=virus
BAAV ITR+AAV5 Rep+AAV4 Cap=virus BAAV ITR+AAV5 Rep+AAV5 Cap=virus
BAAV ITR+AAV5 Rep+AAV6 Cap=virus
BAAV ITR+AAV5 Rep+AAV7 Cap=virus
BAAV ITR+AAV5 Rep+AAV8 Cap=virus
BAAV ITR+AAV5 Rep+AAAV Cap=virus
AAV1 ITR+AAV1 Rep+BAAV Cap=virus
AAV2 ITR+AAV2 Rep+BAAV Cap=virus
AAV3 ITR+AAV3 Rep+BAAV Cap=virus
AAV4 ITR+AAV4 Rep+BAAV Cap=virus
AAV5 ITR+AAV5 Rep+BAAV Cap=virus
AAV6 ITR+AAV6 Rep+BAAV Cap=virus
AAV7 ITR+AAV7 Rep+BAAV Cap=virus
AAV8 ITR+AAV8 Rep+BAAV Cap=virus
AAAV ITR+AAAV Rep+BAAV Cap=virus One of skill in the art would know how to employ standard techniques to obtain the sequences from any of AAV1-8 or AAAV in order to combine them with BAAV sequences. Examples of BAAV sequences that can be utilized in these constructs can be found herein and under GenBank Accession No. AY388617 and these sequences are hereby incorporated in their entireties by this reference. Examples of AAV1 sequences that can be utilized in these constructs can be found in GenBank under Accession No. AF063497 and these sequences are hereby incorporated in their entireties by this reference. Examples of AAV2 sequences that can be utilized in these constructs can be found in GenBank under Accession No. AF043303 and these sequences are hereby incorporated in their entireties by this reference. Examples of AAV3 sequences that can be utilized in these constructs can be found in GenBank under Accession No. NC 001729 and these sequences are hereby incorporated in their entireties by this reference. Examples of AAV4 sequences that can be utilized in these constructs can be found in GenBank under Accession No. U89790 and these sequences are hereby incorporated in their entireties by this reference. Examples of AAV5 sequences that can be utilized in these constructs can be found in GenBank under Accession No. AF085716 and these sequences are hereby incorporated in their entireties by this reference. Examples of AAV6 sequences that can be utilized in these constructs can be found in GenBank under Accession No. NC_001862 and AF028704 and these sequences are hereby incorporated in their entireties by this reference. Examples of AAV7 sequences that can be utilized in these constructs can be found in GenBank under Accession No. AF513851 and these sequences are hereby incorporated in their entireties by this reference. Examples of AAV8 sequences that can be utilized in these constructs can be found in GenBank under Accession No. AF513852 and these sequences are hereby incorporated in their entireties by this reference. Examples of AAAV sequences that can be utilized in these constructs can be found in GenBank under Accession No. AY186198 and these sequences are hereby incorporated in their entireties by this reference.

In any of the constructs described herein, inclusion of a promoter is preferred. As used in the constructs herein, unless otherwise specified, Cap (capsid) refers to any of BAAV VP1, BAAV VP2, BAAV VP3, combinations thereof, functional fragments of any of VP1, VP2 or VP3, or chimeric capsids as described herein. The ITRs of the constructs described herein, can be chimeric recombinant ITRs as described elsewhere in the application.

Conjugates of recombinant or wild-type BAAV virions and nucleic acids or proteins can be used to deliver those molecules to a cell. For example, the purified BAAV can be used as a vehicle for delivering DNA bound to the exterior of the virus. Examples of this are to conjugate the DNA to the virion by a bridge using poly-L-lysine or other charged molecule.

Also contemplated are virosomes that contain BAAV structural proteins (BAAV capsid proteins), lipids such as DOTAP, and nucleic acids that are complexed via charge interaction to introduce DNA into cells.

Also provided herein are conjugates that utilize the BAAV capsid or a unique region of the BAAV capsid protein (e.g. VP1, VP2 or VP3 or combinations thereof) to introduce DNA into cells. For example, the BAAV VP3 protein or fragment thereof, can be conjugated to a DNA on a plasmid that is conjugated to a lipid. Cells can be infected using the targeting ability of the VP3 capsid protein to achieve the desired tissue tropism, specific to BAAV. BAAV VP1 and VP2 proteins can also be utilized to introduce DNA or other molecules into cells. By further incorporating the Rep protein and the AAV TRS into the DNA-containing conjugate, cells can be transduced and targeted integration can be achieved. For example, if BAAV specific targeted integration is desired, a conjugate composed of the BAAV VP3 capsid, BAAV rep or a fragment of BAAV rep, BAAV TRS, the rep binding site, the exogenous DNA of interest, and a lipid, can be utilized to achieve BAAV specific tropism and BAAV specific targeted integration in the genome.

Further provided herein are chimeric viruses where BAAV vectors can be encapsidated by herpes simplex virus (HSV) (Heister, T., et al. J. Virol. 2002 July; 76(14):7163-73), incorporated herein for its teaching of HSV/AAV hybrid vectors), baculovirus or other viruses to achieve a desired tropism associated with another virus. For example, the BAAV ITRs could be encapsidated by HSV and cells could be infected. Post-infection, the ITRs of BAAV could be acted on by BAAV rep provided in the system or in a separate vehicle to rescue BAAV from the genome. Therefore, the cellular tropism of HSV can be combined with BAAV rep mediated targeted integration. Other viruses that could be utilized to construct chimeric viruses include lentivirus, retrovirus, pseudotyped retroviral vectors and adenoviral vectors.

Provided herein are isolated nucleic acids of BAAV. For example, provided is an isolated nucleic acid comprising the nucleotide sequence set forth in SEQ ID NO:1 (BAAV genome). This nucleic acid, or portions thereof, can be inserted into vectors, such as plasmids, yeast artificial chromosomes, or other viral vector (particle), if desired, by standard cloning methods. Also provided is an isolated nucleic acid consisting essentially of the nucleotide sequence set forth in SEQ ID NO:1.

The phrase "consisting essentially of" is used herein to refer to a composition that comprises the essential characteristics of the identified composition. By "essential" is meant the characteristics that contribute to the structure or function of the disclosed molecule. Thus, any substitution, deletion or addition to the provided composition that does not significantly alter the defining characteristics of the composition are considered therein.

For example, if an amino acid sequence X is disclosed, then a provided polypeptide consisting essentially of the amino acid sequence X includes, for example, conservative amino acid substitutions (as described below) that do not significantly alter the essential characteristics of the polypeptide, e.g., secondary/tertiary structure or function of the protein. The provided polypeptide can further constitute a fusion protein or otherwise have additional N-terminal, C-terminal, or intermediate amino acid sequences, e.g., linkers or tags. "Linker", as used herein, is an amino acid sequences or insertion that can be used to connect or separate two distinct polypeptides or polypeptide fragments, wherein the linker does not otherwise contribute to the essential function of the composition. A polypeptide provided herein, can have an amino acid linker comprising, for example, the amino acids GLS, ALS, or LLA. A "tag", as used herein, refers to a distinct amino acid sequence that can be used to detect or purify the provided polypeptide, wherein the tag does not otherwise contribute to the essential function of the composition. The provided polypeptide can further have deleted N-terminal, C-terminal or intermediate amino acids that do not contribute to the essential activity of the polypeptide.

As another example, if a nucleic acid X is disclosed, then a provided nucleic acid consisting essentially of nucleic acid sequence X, includes, for example, nucleotide substitutions that do not alter the amino acid sequence of the encoded polypeptide, i.e., due to degeneracy. If sequence X comprises introns and exons, then the provided nucleic acid can further be the cDNA sequence that lacks the introns but comprises the exons of sequence X. To the extent that specific genes within a genome are identified herein, it is further understood that the disclosure of a nucleic acid consisting essentially of the genome sequence would include fragments of the genome such as isolated sequences comprising a gene or genes within the genome.

Other characteristics of nucleic acid or amino acid sequences that are not herein considered essential include, for example, junk DNA between genes or any identifiable sequence unit, e.g., promoters, enhancers, transmembrane domains, poly-adenylation sequences, signal sequences, etc., that when substituted or removed would be presumed by one skilled in the art to not significantly alter the essential characteristics of the disclosed sequence.

Thus, the nucleotides of SEQ ID NO:1 can have minor modifications and still be contemplated herein. For example, modifications that do not alter the amino acid encoded by any given codon (such as by modification of the third, "wobble," position in a codon) can readily be made, and such alterations are known in the art. Furthermore, modifications that cause a resulting neutral (conserved) amino acid substitution of a similar amino acid can be made in a coding region of the genome. Additionally, modifications as described herein for the BAAV components, such as the ITRs, the p5 promoter, etc. are contemplated herein. Furthermore, modifications to regions of SEQ ID NO:1 other than in the ITR, TRS, Rep binding site and hairpin are likely to be tolerated without serious impact on the function of the nucleic acid as a recombinant vector.

As used herein, the term "isolated" refers to a nucleic acid separated or significantly free from at least some of the other components of the naturally occurring organism, for example, the cell structural components or viral components commonly found associated with nucleic acids in the environment of the virus and/or other nucleic acids. The isolation of the native nucleic acids can be accomplished, for example, by techniques such as cell lysis followed by phenol plus chloroform extraction, followed by ethanol precipitation of the nucleic acids. The nucleic acids provided herein can be isolated from cells according to any of many methods well known in the art.

As used herein, the term "nucleic acid" refers to single- or multiple-stranded molecules which may be DNA or RNA, or any combination thereof, including modifications to those nucleic acids. The nucleic acid may represent a coding strand or its complement, or any combination thereof. Nucleic acids may be identical in sequence to the sequences which are naturally occurring for any of the genes discussed herein or may include alternative codons which encode the same amino acid as those provided herein, including that which is found in the naturally occurring sequence. These nucleic acids can also be modified from their typical structure. Such modifications include, but are not limited to, methylated nucleic acids, the substitution of a non-bridging oxygen on the phosphate residue with either a sulfur (yielding phosphorothioate deoxynucleotides), selenium (yielding phosphorselenoate deoxynucleotides), or methyl groups (yielding methylphosphonate deoxynucleotides).

Additionally provided is an isolated nucleic acid that selectively hybridizes with any nucleic acid disclosed herein, including the entire BAAV genome and any unique fragment thereof, including the Rep and capsid encoding sequences, promoters and ITRs (e.g. SEQ ID NOS: 1, 2, 4, 6, 8, 10, 12, 13, 14, 15, 16, 17). Specifically, the nucleic acid can selectively or specifically hybridize to an isolated nucleic acid consisting of the nucleotide sequence set forth in SEQ ID NO:1 (BAAV genome). Further provided is an isolated nucleic acid that selectively or specifically hybridizes with an isolated nucleic acid comprising the nucleotide sequence set forth in SEQ ID NO:1 (BAAV genome). By "selectively hybridizes" as used herein is meant a nucleic acid that hybridizes to one of the disclosed nucleic acids under sufficient stringency conditions without significant hybridization to a nucleic acid encoding an unrelated protein, and particularly, without detectably hybridizing to nucleic acids of AAV2. Thus, a nucleic acid that selectively hybridizes with a nucleic acid provided herein will not selectively hybridize under stringent conditions with a nucleic acid encoding a different protein or the corresponding protein from a different serotype of the virus, and vice versa. A "specifically hybridizing" nucleic acid is one that hybridizes under stringent conditions to only a nucleic acid found in BAAV. Therefore, nucleic acids for use, for example, as primers and probes to detect or amplify the target nucleic acids are contemplated herein. Nucleic acid fragments that selectively hybridize to any given nucleic acid can be used, e.g., as primers and or probes for further hybridization or for amplification methods (e.g., polymerase chain reaction (PCR), ligase chain reaction (LCR)). Additionally, for example, a primer or probe can be designed that selectively hybridizes with both BAAV and a gene of interest carried within the BAAV vector (i.e., a chimeric nucleic acid).

Stringency of hybridization is controlled by both temperature and salt concentration of either or both of the hybridization and washing steps. Typically, the stringency of hybridization to achieve selective hybridization involves hybridization in high ionic strength solution (6×SSC or 6×SSPE) at a temperature that is about 12-25° C. below the $T_m$ (the melting temperature at which half of the molecules dissociate from their hybridization partners) followed by washing at a combination of temperature and salt concentration chosen so that the washing temperature is about 5° C. to 20° C. below the $T_m$. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The washing temperatures can be used as described above to achieve selective stringency, as is known in the art. (Sambrook et al., *Molecular Cloning: A Laboratory Manual,* 2nd Ed., Cold Spring Harbor Laboratory, Cold Spring Harbor, N.Y., 1989; Kunkel et al. *Methods Enzymol.* 1987:154:367, 1987). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

A nucleic acid that selectively hybridizes to any portion of the BAAV genome is contemplated herein. Therefore, a nucleic acid that selectively hybridizes to BAAV can be of longer length than the BAAV genome, it can be about the same length as the BAAV genome or it can be shorter than the BAAV genome. The length of the nucleic acid is limited on the shorter end of the size range only by its specificity for hybridization to BAAV, i.e., once it is too short, typically less than about 5 to 7 nucleotides in length, it will no longer bind specifically to BAAV, but rather will hybridize to numerous background nucleic acids. Additionally contemplated herein is a nucleic acid that has a portion that specifically hybridizes to BAAV and a portion that specifically hybridizes to a gene of interest inserted within BAAV.

Provided is an isolated nucleic acid comprising a BAAV p5 promoter. The nucleic acid can consist of the sequence set forth in SEQ ID NO:15. The nucleic acid can consist essentially of the sequence set forth in SEQ ID NO:15. Further provided is a nucleic acid that selectively hybridizes with the sequence set forth in SEQ ID NO:15.

Provided is an isolated nucleic acid comprising a BAAV p19 promoter. The nucleic acid can consist of the sequence set forth in SEQ ID NO:16. The nucleic acid can consist essentially of the sequence set forth in SEQ ID NO:16. Further provided is a nucleic acid that selectively hybridizes with the sequence set forth in SEQ ID NO:16.

Provided is an isolated nucleic acid comprising a BAAV p40 promoter. The nucleic acid can consist of the sequence set forth in SEQ ID NO:17. The nucleic acid can consist essentially of the sequence set forth in SEQ ID NO:17. Further provided is a nucleic acid that selectively hybridizes with the sequence set forth in SEQ ID NO:17.

Provided is an isolated nucleic acid comprising a BAAV ITR. The isolated nucleic acid can comprise the sequence set forth in SEQ ID NO:12. The isolated nucleic acid can consist essentially of the sequence set forth in SEQ ID NO:12. Further provided is an isolated nucleic acid that selectively hybridizes with the sequence set forth in SEQ ID NO:12.

Further provided is an isolated nucleic acid encoding a bovine adeno-associated virus Rep protein. The BAAV Rep proteins are encoded by open reading frame (ORF) 1 of the BAAV genome. Examples of the BAAV Rep genes are shown in the nucleic acid set forth in SEQ ID NO:1, and include nucleic acids consisting essentially of the nucleotide sequences set forth in SEQ ID NOS:2 (rep78), 4(rep52) and nucleic acids comprising the nucleotide sequences set forth in SEQ ID NOS:2 and 4. However, it is contemplated that the Rep nucleic acid can include any one, two, three, or four of the four Rep proteins, in any order, in such a nucleic acid.

Furthermore, minor modifications are contemplated in the nucleic acid, such as silent mutations in the coding sequences, mutations that make neutral or conservative changes in the encoded amino acid sequence, and mutations in regulatory regions that do not disrupt the expression of the gene. Examples of other minor modifications are known in the art. Further modifications can be made in the nucleic acid, such as to disrupt or alter expression of one or more of the Rep proteins in order to, for example, determine the effect of such a disruption; such as to mutate one or more of the Rep proteins to determine the resulting effect, etc. However, in general, a modified nucleic acid encoding a Rep protein will have at least about 85%, about 90%, about 93%, about 95%, about 98% or 100% homology to the Rep nucleic sequences described herein e.g., SEQ ID NOS: 2, and 4, and the Rep polypeptide encoded therein will have overall about 93%, about 95%, about 98%, about 99% or 100% homology with the amino acid sequence described herein, e.g., SEQ ID NOS:3 and 5. Percent homology is determined by the techniques described herein.

Provided herein is an isolated nucleic acid that selectively or specifically hybridizes with a nucleic acid consisting essentially of the nucleotide sequence set forth in SEQ ID NOS:2 and 4, and an isolated nucleic acid that selectively hybridizes with a nucleic acid comprising the nucleotide sequence set forth in SEQ ID NOS:2 and 4. "Selectively hybridizing" and "stringency of hybridization" is defined elsewhere herein.

As described above, provided is the nucleic acid encoding a Rep 78 protein and, in particular an isolated nucleic acid comprising the nucleotide sequence set forth in SEQ ID NO: 2, an isolated nucleic acid consisting essentially of the nucleotide sequence set forth in SEQ ID NO: 2, and a nucleic acid encoding the bovine adeno-associated virus protein having the amino acid sequence set forth in SEQ ID NO: 3. Also provided is the nucleic acid encoding a Rep 52 protein, and in particular an isolated nucleic acid comprising the nucleotide sequence set forth in SEQ ID NO:4, an isolated nucleic acid consisting essentially of the nucleotide sequence set forth in SEQ ID NO:4, and a nucleic acid encoding the bovine adeno-associated virus Rep 52 protein having the amino acid sequence set forth in SEQ ID NO:5. As described elsewhere herein, these nucleic acids can have minor modifications, including silent nucleotide substitutions, mutations causing conservative amino acid substitutions in the encoded proteins, and mutations in control regions that do not or minimally affect the encoded amino acid sequence.

Further provided is an isolated nucleic acid encoding a BAAV Capsid protein. Furthermore, provided is a nucleic acid encoding each of the three BAAV capsid proteins, VP1, VP2, and VP3. Thus, provided is an isolated nucleic acid encoding BAAV VP1, a nucleic acid encoding BAAV VP2, and an isolated nucleic acid encoding BAAV VP3. Thus, provided is an isolated nucleic acid encoding the amino acid sequence set forth in SEQ ID NO:7 (VP1); an isolated nucleic acid encoding the amino acid sequence set forth in SEQ ID NO:9 (VP2), and an isolated nucleic acid encoding the amino acid sequence set forth in SEQ ID NO:11 (VP3). Also specifically provided is an isolated nucleic acid comprising SEQ ID NO:6 (VP1 gene); an isolated nucleic acid comprising SEQ ID NO:8 (VP2 gene); and an isolated nucleic acid comprising SEQ ID NO:10 (VP3 gene). Also specifically provided is an isolated nucleic acid consisting essentially of SEQ ID NO:6 (VP1 gene), an isolated nucleic acid consisting essentially of SEQ ID NO:8 (VP2 gene), and an isolated nucleic acid consisting essentially of SEQ ID NO:10 (VP3 gene). Minor modifications in the nucleotide sequences encoding the capsid, or coat, proteins are contemplated, as described above for other BAAV nucleic acids. However, in general, a modified nucleic acid encoding a capsid protein will have at least about 85%, about 90%, about 93%, about 95%, about 98% or 100% homology to the capsid nucleic sequences described herein e.g., SEQ ID NOS: 6, 8, and 10, and the capsid polypeptide encoded therein will have overall about 93%, about 95%, about 98%, about 99% or 100% homology with the amino acid sequence described herein, e.g., SEQ ID NOS:7, 9, and 11. Isolated nucleic acids that selectively hybridize with the nucleic acids of SEQ ID NOS: 6, 8 or 10 under the conditions described above are also provided.

Also provided is a cell containing one or more of the herein described nucleic acids, such as the BAAV genome, BAAV ORF1 and ORF2, each BAAV Rep protein gene, or each BAAV capsid protein gene. Such a cell can be any desired cell and can be selected based upon the use intended. For example, cells can include bacterial cells, yeast cells, insect cells, human HeLa cells and simian Cos cells as well as other human and mammalian cells and cell lines. Primary cultures as well as established cultures and cell lines can be used. Nucleic acids provided herein can be delivered into cells by any selected means, in particular depending upon the target cells. Many delivery means are well-known in the art. For example, electroporation, calcium phosphate precipitation, microinjection, cationic or anionic liposomes, and liposomes in combination with a nuclear localization signal peptide for delivery to the nucleus can be utilized, as is known in the art. Additionally, if the nucleic acids are in a viral particle, the cells can simply be transduced with the virion by standard means known in the art for AAV transduction. Small amounts of the recombinant BAAV virus can be made to infect cells and produce more of itself.

Provided herein are purified BAAV polypeptides. The term "polypeptide" as used herein refers to a polymer of amino acids and includes full-length proteins and fragments thereof. Thus, "protein," polypeptide," and "peptide" are often used interchangeably herein. Substitutions can be selected by known parameters to be neutral (see, e.g., Robinson W E Jr, and Mitchell W M., AIDS 4:S151-S162 (1990)). As will be appreciated by those skilled in the art, also provided herein are those polypeptides having slight variations in amino acid sequences or other properties. Such variations may arise naturally as allelic variations (e.g., due to genetic polymorphism) or may be produced by human intervention (e.g., by mutagenesis of cloned DNA sequences), such as induced point, deletion, insertion and substitution mutants. Minor changes in amino acid sequence are generally preferred, such as conservative amino acid replacements, small internal deletions or insertions, and additions or deletions at the ends of the molecules. Substitutions may be designed based on, for example, the model of Dayhoff, et al. (in *Atlas of Protein Sequence and Structure* 1978, Nat'l Biomed. Res. Found., Washington, D.C.). These modifications can result in changes in the amino acid sequence, provide silent mutations, modify a restriction site, or provide other specific mutations. The location of any modifications to the polypeptide will often determine its impact on function. Particularly, alterations in regions nonessential to protein function will be tolerated with fewer effects on function. Elsewhere in the application regions of the BAAV proteins are described to provide guidance as to where substitutions, additions or deletions can be made to minimize the likelihood of disturbing the function of the variant.

Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations | |
|---|---|---|
| alanine | Ala | A |
| allosoleucine | AIle | |
| arginine | Arg | R |
| asparagine | Asn | N |
| aspartic acid | Asp | D |
| cysteine | Cys | C |
| glutamic acid | Glu | E |
| glutamine | Gln | Q |
| glycine | Gly | G |
| histidine | His | H |
| isolelucine | Ile | I |
| leucine | Leu | L |
| lysine | Lys | K |
| phenylalanine | Phe | F |
| proline | Pro | P |
| pyroglutamic acid | pGlu | |
| serine | Ser | S |
| threonine | Thr | T |
| tyrosine | Tyr | Y |
| tryptophan | Trp | W |
| valine | Val | V |

TABLE 2

Amino Acid Substitutions
Original Residue Exemplary Conservative Substitutions, others are known in the art.

| | |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |

TABLE 2-continued

Amino Acid Substitutions
Original Residue Exemplary Conservative
Substitutions, others are known in the art.

| | |
|---|---|
| Trp | Tyr |
| Tyr | Trp; Phe |
| Val | Ile; Leu |

Substantial changes in function or immunological identity can result from selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Generally, a conservative substitution is a substitution of an amino acid residue for another amino acid residue having similar biochemical properties. Typically, conservative substitutions have little to no impact on the biological activity of a resulting polypeptide. In a particular example, a conservative substitution is an amino acid substitution in a peptide that does not substantially affect the biological function of the peptide. A peptide can include one or more amino acid substitutions, for example 2-10 conservative substitutions, 2-5 conservative substitutions, 4-9 conservative substitutions, such as 2, 5 or 10 conservative substitutions.

For example, a conservative substitution in VP3 peptide (such as a peptide encoded by SEQ ID NO:9) does not substantially affect the ability of VP3 peptide to confer the unique tropism of the BAAV particle. A polypeptide can be produced to contain one or more conservative substitutions by manipulating the nucleotide sequence that encodes that polypeptide using, for example, standard procedures such as site-directed mutagenesis or PCR. Alternatively, a polypeptide can be produced to contain one or more conservative substitutions by using standard peptide synthesis methods. An alanine scan can be used to identify which amino acid residues in a protein can tolerate an amino acid substitution. In one example, the biological activity of the protein is not decreased by more than 25%, for example not more than 20%, for example not more than 10%, when an alanine, or other conservative amino acid (such as those listed below), is substituted for one or more native amino acids.

Examples of amino acids which can be substituted for an original amino acid in a protein and which are regarded as conservative substitutions include, but are not limited to: Ser for Ala; Lys for Arg; Gln or H is for Asn; Glu for Asp; Ser for Cys; Asn for Gln; Asp for Glu; Pro for Gly; Asn or Gln for H is; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

Further information about conservative substitutions can be found in, among other locations in, Ben-Bassat et al., (J. Bacteriol. 169:751-7, 1987), O'Regan et al., (Gene 77:237-51, 1989), Sahin-Toth et al., (Protein Sci. 3:240-7, 1994), Hochuli et al., (Bio/Technology 6:1321-5, 1988) and in standard textbooks of genetics and molecular biology.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Enginerring Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include CH2NH—, —CH2S—, —CH2-CH2-, —CH═CH— (cis and trans), —COCH2-, —CH(OH)CH2-, and —CHH2SO— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—CH2NH—, CH2CH2-); Spatola et al. Life Sci 38:1243-

1249 (1986) (—CH H2-S); Hann J. Chem. Soc Perkin Trans. 1307-314 (1982) (—CH—CH—, cis and trans); Almquist et al. J. Med. Chem. 23:1392-1398 (1980) (—COCH2-); Jennings-White et al. Tetrahedron Lett 23:2533 (1982) (—COCH2-); Szelke et al. European Appin, EP 45665 CA (1982): 97:39405 (1982) (—CH(OH)CH2-); Holladay et al. Tetrahedron. Lett 24:4401-4404 (1983) (—C(OH)CH2-); and Hruby Life Sci 31:189-199 (1982) (—CH2-S—); each of which is incorporated herein by reference. A particularly preferred non-peptide linkage is —CH2NH—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

A polypeptide provided herein can be readily obtained by any of several means. For example, the polypeptide of interest can be synthesized chemically by standard methods. Additionally, the coding regions of the genes can be recombinantly expressed and the resulting polypeptide isolated by standard methods. Furthermore, an antibody specific for the resulting polypeptide can be raised by standard methods (see, e.g., Harlow and Lane, *Antibodies: A Laboratory Manual*, Cold Spring Harbor Laboratory, Cold Spring Harbor, N.Y., 1988), and the protein can be isolated from a cell expressing the nucleic acid encoding the polypeptide by selective hybridization with the antibody. This protein can be purified to the extent desired by standard methods of protein purification (see, e.g., Sambrook et al., *Molecular Cloning: A Laboratory Manual*, 2nd Ed., Cold Spring Harbor Laboratory, Cold Spring Harbor, N.Y., 1989).

An antigenic or immunoreactive fragment of the provided compositions and methods is typically an amino acid sequence of at least about 5 consecutive amino acids, and it can be derived from the BAAV polypeptide amino acid sequence. An antigenic BAAV fragment is any fragment unique to the BAAV protein, as described herein, against which a BAAV-specific antibody can be raised, by standard methods. Thus, the resulting antibody-antigen reaction should be specific for BAAV.

By "unique fragment thereof" is meant any smaller polypeptide fragment encoded by a BAAV rep gene that is of sufficient length to be found only in the Rep polypeptide. Substitutions and modifications of the amino acid sequence can be made as described herein and, further, can include protein processing modifications, such as glycosylation, to the polypeptide. Typically, to be unique, a polypeptide fragment provided herein will be at least about 5 amino acids in length; however, unique fragments can be 6, 7, 8, 9, 10, 20, 30, 40, 50, 60, 70, 80, 90, 100 or more amino acids in length. A unique polypeptide will typically comprise such a unique fragment; however, a unique polypeptide can also be determined by its overall homology. A unique polypeptide can be 6, 7, 8, 9, 10, 20, 30, 40, 50, 60, 70, 80, 90, 100 or more amino acids in length. Uniqueness of a polypeptide fragment can readily be determined by standard methods such as searches of computer databases of known peptide or nucleic acid sequences or by hybridization studies to the nucleic acid encoding the protein or to the protein itself, as known in the art. The uniqueness of a polypeptide fragment can also be determined immunologically as well as functionally. Uniqueness can be simply determined in an amino acid-by-amino acid comparison of the polypeptides.

Provided is an isolated BAAV Rep protein. A BAAV Rep polypeptide is encoded by ORF1 of BAAV. Also provided is each individual BAAV Rep protein. Provided is an isolated polypeptide, comprising BAAV Rep 52, or a unique fragment thereof. BAAV Rep 52 can have the amino acid sequence set forth in SEQ ID NO:5. BAAV Rep 52 protein can be encoded by the nucleic acid sequence set forth in SEQ ID NO:2, or a unique fragment thereof. Provided is an isolated polypeptide, comprising BAAV Rep 78, or a unique fragment thereof. BAAV Rep 78 can have the amino acid sequence set forth in SEQ ID NO:3. BAAV Rep 78 protein can be encoded by the nucleic acid sequence set forth in SEQ ID NO:4, or a unique fragment thereof.

Further provided is an isolated BAAV Capsid protein or a unique fragment thereof. BAAV capsid protein is encoded by ORF 2 of BAAV. Further provided are the individual BAAV capsid proteins, VP1, VP2 and VP3 or unique fragments thereof. Thus, provided is an isolated polypeptide having the amino acid sequence set forth in SEQ ID NO:7 (VP1). Further provided is an isolated polypeptide consisting essentially of the amino acid sequence set forth in SEQ ID NO:7. Additionally provided is an isolated polypeptide having the amino acid sequence set forth in SEQ ID NO:9 (VP2). Further provided is an isolated polypeptide consisting essentially of the amino acid sequence set forth in SEQ ID NO:9. Also provided is an isolated polypeptide having the amino acid sequence set forth in SEQ ID NO:11 (VP3). Further provided is an isolated polypeptide consisting essentially of the amino acid sequence set forth in SEQ ID NO:11.

By "unique fragment thereof" is meant any smaller polypeptide fragment encoded by any BAAV capsid gene that is of sufficient length to be found only in the BAAV capsid protein. Substitutions and modifications of the amino acid sequence can be made as described above and, further, can include protein processing modifications, such as glycosylation, to the polypeptide. However, a BAAV Capsid polypeptide including all three coat proteins will have greater than about 56% overall homology to the polypeptide encoded by the nucleotides set forth in SEQ ID NOS:6, 8 or 10. The protein can have about 65%, about 70%, about 75%, about 80%, about 85%, about 90%, 93%, 95%, 97% or even 100% homology to the amino acid sequence encoded by the nucleotides set forth in SEQ ID NOS:6, 8 or 10. A BAAV VP1 polypeptide can have at least about 58%, about 60%, about 70%, about 80%, about 90%, 93%, 95%, 97% or about 100% homology to the amino acid sequence set forth in SEQ ID NO:7. A BAAV VP2 polypeptide can have at least about 58%, about 60%, about 70%, about 80%, about 90%, 93%, 95%, 97% or about 100% homology to the amino acid sequence set forth in SEQ ID NO:9. A BAAV VP3 polypeptide can have at least about 60%, about 70%, about 80%, about 90%, 93%, 95%, 97% or about 100% homology to the amino acid sequence set forth in SEQ ID NO:11.

Further provided is an isolated antibody that specifically binds a BAAV Rep protein or a unique epitope thereof. Also provided are isolated antibodies that specifically bind the BAAV Rep 52 protein and the BAAV Rep 78 protein having the amino acid sequences set forth in SEQ ID NO: 5 and SEQ ID NO: 3, respectively or that specifically binds a unique fragment thereof. Clearly, any given antibody can recognize and bind one of a number of possible epitopes present in the polypeptide; thus only a unique portion of a polypeptide (having the epitope) may need to be present in an assay to determine if the antibody specifically binds the polypeptide.

Additionally provided is an isolated antibody that specifically binds any of the bovine adeno-associated virus capsid proteins (VP1, VP2 or VP3), a unique epitope thereof, or the polypeptide comprising all three BAAV coat proteins. Also provided is an isolated antibody that specifically binds the BAAV capsid protein having the amino acid sequence set forth in SEQ ID NO:7 (VP1), or that specifically binds a unique fragment thereof. Further provided is an isolated antibody that specifically binds the BAAV Capsid protein having the amino acid sequence set forth in SEQ ID NO:9 (VP2), or that specifically binds a unique fragment thereof. Additionally provided is an isolated antibody that specifically binds the BAAV Capsid protein having the amino acid sequence set forth in SEQ ID NO:11 (VP3), or that specifically binds a unique fragment thereof. Again, any given antibody can recognize and bind one of a number of possible epitopes present in the polypeptide; thus only a unique portion of a polypeptide (having the epitope) may need to be present in an assay to determine if the antibody specifically binds the polypeptide.

The antibody can be a component of a composition that comprises an antibody that specifically binds the BAAV protein. The composition can further comprise, e.g., serum, serum-free medium, or a pharmaceutically acceptable carrier such as physiological saline, etc.

By "an antibody that specifically binds" a BAAV polypeptide or protein is meant an antibody that selectively binds to an epitope on any portion of the BAAV peptide such that the antibody binds specifically to the corresponding BAAV polypeptide without significant background. Specific binding by an antibody further means that the antibody can be used to selectively remove the target polypeptide from a sample comprising the polypeptide or and can readily be determined by radioimmunoassay (RIA), bioassay, or enzyme-linked immunosorbant (ELISA) technology. An ELISA method effective for the detection of the specific antibody-antigen binding can, for example, be as follows: (1) bind the antibody to a substrate; (2) contact the bound antibody with a sample containing the antigen; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe the color change.

An antibody can include antibody fragments such as Fab fragments which retain the binding activity. Antibodies can be made as described in, e.g., Harlow and Lane, *Antibodies: A Laboratory Manual*, Cold Spring Harbor Laboratory, Cold Spring Harbor, N.Y. (1988). Briefly, purified antigen can be injected into an animal in an amount and in intervals sufficient to elicit an immune response. Antibodies can either be purified directly, or spleen cells can be obtained from the animal. The cells are then fused with an immortal cell line and screened for antibody secretion. Individual hybridomas are then propagated as individual clones serving as a source for a particular monoclonal antibody.

Additionally provided is a method of screening a cell for infectivity by BAAV, comprising contacting the cell with BAAV and detecting the presence of BAAV in the cells. BAAV particles can be detected using any standard physical or biochemical methods. For example, physical methods that can be used for this detection include DNA based methods such as 1) polymerase chain reaction (PCR) for viral DNA or RNA or 2) direct hybridization with labeled probes, and immunological methods such as by 3) antibody directed against the viral structural or non-structural proteins. Catalytic methods of viral detection include, but are not limited to, detection of site and strand specific DNA nicking activity of Rep proteins or replication of an AAV origin-containing substrate. Reporter genes can also be utilized to detect cells that transduce BAAV. For example, β-gal, green fluorescent protein or luciferase can be inserted into a recombinant BAAV. The cell can then be contacted with the recombinant BAAV, either in vitro or in vivo and a colorimetric assay could detect a color change in the cells that would indicate transduction of BAAV in the cell. Additional detection methods are outlined in Fields, *Virology*, Raven Press, New York, N.Y. 1996.

Provided is a method of screening a cell for infectivity by BAAV, wherein the presence of BAAV in the cells is determined by nucleic acid hybridization methods, a nucleic acid probe for such detection can comprise, for example, a unique fragment of any of the BAAV nucleic acids provided herein. The uniqueness of any nucleic acid probe can readily be determined as described herein. Additionally, the presence of BAAV in cells can be determined by fluorescence, antibodies to gene products, focus forming assays, plaque lifts, Western blots and chromogenic assays. The nucleic acid can be, for example, the nucleic acid whose nucleotide sequence is set forth in SEQ ID NO: 1, 3, 4, 6, 8, 10, 12, 13, 14, 15, 16, 17 or a unique fragment thereof.

Provided is a method of determining the suitability of a BAAV vector for administration to a subject comprising contacting an antibody-containing sample from the subject with an antigenic fragment of an isolated BAAV Rep or Capsid protein, and detecting an antibody-antigen reaction in the sample, the presence of a neutralizing reaction indicating the BAAV vector to be unsuitable for use in the subject. Further provided is a method of determining the presence in a subject of a BAAV-specific antibody comprising contacting an antibody-containing sample from the subject with an antigenic fragment of an isolated BAAV Rep or Capsid protein and detecting an antibody-antigen reaction in the sample, the presence of a reaction indicating the presence of a BAAV-specific antibody in the subject. The present methods of determining the suitability of a BAAV vector for administration to a subject or the presence of a BAAV-specific antibody in a subject can comprise contacting an antibody-containing sample from the subject with a unique antigenic or immunogenic fragment of a BAAV Rep protein (e.g. Rep 52, Rep 78) and detecting an antibody-antigen reaction in the sample, the presence of a reaction indicating the presence of a BAAV-specific antibody and therefore the BAAV vector to be unsuitable for use in the subject. The BAAV Rep proteins are provided herein, and their antigenic fragments are routinely determined. The BAAV capsid protein can be used to select an antigenic or immunogenic fragment, for example from the amino acid sequence set forth in SEQ ID NO:7 (VP1), the amino acid sequence set forth in SEQ ID NO: 9 (VP2) or the amino acid sequence set forth in SEQ ID NO:11 (VP3). Alternatively, or additionally, an antigenic or immunogenic fragment of an isolated BAAV Rep protein can be utilized in this determination method. The BAAV Rep protein from which an antigenic fragment is selected can have the amino acid sequence encoded by the nucleic acid set forth in SEQ ID NO:1, the amino acid sequence set forth in SEQ ID NO:2, or the amino acid sequence set forth in SEQ ID NO:4, the amino acid sequence set forth in SEQ ID NO: 3, or the amino acid sequence set forth in SEQ ID NO:5.

The BAAV polypeptide fragments can be analyzed to determine their antigenicity, immunogenicity and/or specificity. Briefly, various concentrations of a putative immunogenically specific fragment are prepared and administered to a subject and the immunological response (e.g., the production of antibodies or cell mediated immunity) of an animal to each concentration is determined. The amounts of antigen administered depend on the subject, e.g. a human, rabbit or a guinea pig, the condition of the subject, the size of the subject, etc. Thereafter an animal so inoculated with the antigen can be exposed to the BAAV viral particle or BAAV protein to test the immunoreactivity or the antigenicity of the specific immunogenic fragment. The specificity of a putative antigenic or immunogenic fragment can be ascertained by testing sera, other fluids or lymphocytes from the inoculated animal for cross reactivity with other closely related viruses, such as AAV1-8 or AAAV.

By the "suitability of a BAAV vector for administration to a subject" is meant a determination of whether the BAAV vector will elicit a neutralizing immune response upon administration to a particular subject. A vector that does not elicit a significant immune response is a potentially suitable vector, whereas a vector that elicits a significant, neutralizing immune response (e.g. at least 90%) is thus likely to be unsuitable for use in that subject. Significance of any detectable immune response is a standard parameter understood by the skilled artisan in the field. For example, one can incubate the subject's serum with the virus, then determine whether that virus retains its ability to transduce cells in culture. If such virus cannot transduce cells in culture, the vector likely has elicited a significant immune response.

Alternatively, or additionally, one skilled in the art could determine whether or not BAAV administration would be suitable for a particular cell type of a subject. For example, the artisan could culture muscle cells in vitro and transduce the cells with BAAV in the presence or absence of the subject's serum. If there is a reduction in transduction efficiency, this could indicate the presence of a neutralizing antibody or other factors that may inhibit transduction. Normally, greater than 90% inhibition would have to be observed in order to rule out the use of BAAV as a vector. However, this limitation could be overcome by treating the subject with an immunosuppressant that could block the factors inhibiting transduction.

As will be recognized by those skilled in the art, numerous types of immunoassays are available for use in the present methods to detect binding between an antibody and a BAAV polypeptide as provided herein. For instance, direct and indirect binding assays, competitive assays, sandwich assays, and the like, as are generally described in, e.g., U.S. Pat. Nos. 4,642,285; 4,376,110; 4,016,043; 3,879,262; 3,852,157; 3,850,752; 3,839,153; 3,791,932; and Harlow and Lane, *Antibodies, A Laboratory Manual*, Cold Spring Harbor Publications, N.Y. (1988). For example, enzyme immunoassays such as immunofluorescence assays (IFA), enzyme linked immunosorbent assays (ELISA) and immunoblotting can be readily adapted to accomplish the detection of the antibody. An ELISA method effective for the detection of the antibody bound to the antigen can, for example, be as follows: (1) bind the antigen to a substrate; (2) contact the bound antigen with a fluid or tissue sample containing the antibody; (3) contact the above with a secondary antibody specific for the antigen and bound to a detectable moiety (e.g., horseradish peroxidase enzyme or alkaline phosphatase enzyme); (4) contact the above with the substrate for the enzyme; (5) contact the above with a color reagent; (6) observe color change.

The antibody-containing sample of this method can comprise any biological sample which would contain the antibody or a cell containing the antibody, such as blood, plasma, serum, bone marrow, saliva and urine.

Also provided is a method of producing the BAAV virus by transducing a cell with the nucleic acid encoding the virus.

The present method further provides a method of delivering an exogenous nucleic acid to a cell comprising administering to the cell a BAAV particle containing a vector comprising the nucleic acid inserted between a pair of AAV inverted terminal repeats, thereby delivering the nucleic acid to the cell.

The AAV ITRs in the vector for the herein described delivery methods can be BAAV ITRs (SEQ ID NOS: 12). Furthermore, the AAV ITRs in the vector for the herein described nucleic acid delivery methods can also comprise AAV1, 2, 3, 4, 5, 6, 7, 8 or AAAV inverted terminal repeats.

Also provided is a method of delivering an exogenous nucleic acid to a subject comprising administering to a cell of or from the subject a BAAV particle containing a vector comprising the nucleic acid inserted between a pair of AAV inverted terminal repeats, and returning the cell to the subject, thereby delivering the nucleic acid to the subject. The AAV ITRs can be any AAV ITRs, including BAAV ITRs, AAV5 ITRs and AAV2 ITRs. For example, in an ex vivo administration, cells are isolated from a subject by standard means according to the cell type and placed in appropriate culture medium, again according to cell type (see, e.g., ATCC catalog). Viral particles are then contacted with the cells as described above, and the virus is allowed to transduce the cells. Cells can then be transplanted back into the subject's body, again by means standard for the cell type and tissue (e.g., in general, U.S. Pat. No. 5,399,346; for neural cells, Dunnett, S. B. and Björklund, A., eds., *Transplantation: Neural Transplantation-A Practical Approach*, Oxford University Press, Oxford (1992)). If desired, prior to transplantation, the cells can be studied for degree of transduction by the virus, by known detection means and as described herein. Cells for ex vivo transduction followed by transplantation into a subject can be selected from those listed above, or can be any other selected cell. Preferably, a selected cell type is examined for its capability to be transfected by BAAV. Preferably, the selected cell will be a cell readily transduced with BAAV particles; however, depending upon the application, even cells with relatively low transduction efficiencies can be useful, particularly if the cell is from a tissue or organ in which even production of a small amount of the protein or antisense RNA encoded by the vector will be beneficial to the subject.

Further provided is a method of delivering an exogenous nucleic acid to a cell in a subject comprising administering to the subject a BAAV particle containing a vector comprising the nucleic acid inserted between a pair of AAV inverted terminal repeats, thereby delivering the nucleic acid to a cell in the subject. Administration can be an ex vivo administration directly to a cell removed from a subject, such as any of the cells listed above, followed by replacement of the cell back into the subject, or administration can be in vivo administration to a cell in the subject. For ex vivo administration, cells are isolated from a subject by standard means according to the cell type and placed in appropriate culture medium, again according to cell type (see, e.g., ATCC catalog). Viral particles are then contacted with the cells as described above, and the virus is allowed to transfect the cells. Cells can then be transplanted back into the subject's body, again by means standard for the cell type and tissue (e.g., for neural cells, Dunnett, S. B. and Björklund, A., eds., *Transplantation: Neural Transplantation—A Practical Approach*, Oxford University Press, Oxford (1992)). If desired, prior to transplantation, the cells can be studied for degree of transfection by the virus, by known detection means and as described herein.

Further provided is a method of delivering a nucleic acid to a cell in a subject having neutralizing antibodies to AAV1-8 comprising administering to the subject a BAAV particle containing a vector comprising the nucleic acid, thereby delivering the nucleic acid to a cell in the subject. A subject that has neutralizing antibodies to AAV1-8 can readily be determined by any of several known means, such as contacting AAV1-8 protein(s) with an antibody-containing sample, such as blood, from a subject and detecting an antigen-antibody reaction in the sample. Delivery of the AAV1-8 particle can be by either ex vivo or in vivo administration as herein described. Thus, a subject who might have an adverse immunogenic reaction to a vector administered in an AAV2 viral particle can have a desired nucleic acid delivered using an AAV1-8 particle. This delivery system can be particularly useful for subjects who have received therapy utilizing AAV1-8 particles in the past and have developed antibodies to AAV1-8. A BAAV regimen can now be substituted to deliver the desired nucleic acid.

In any of the methods of delivering exogenous nucleic acids to a cell or subject described herein, the BAAV-conjugated nucleic acid or BAAV particle-conjugated nucleic acids described herein can be used.

In vivo administration to a human subject or an animal model can be by any of many standard means for administering viruses, depending upon the target organ, tissue or cell. Virus particles can be administered orally, parenterally (e.g., intravenously), by intramuscular injection, intrarectally, by direct tissue or organ injection, by intraperitoneal injection, topically, transdermally, via aerosol delivery, via the mucosa or the like. Viral nucleic acids (non-encapsidated) can also be administered, e.g., as a complex with cationic liposomes, or encapsulated in anionic liposomes. The present compositions can include various amounts of the selected viral particle or non-encapsidated viral nucleic acid in combination with a pharmaceutically acceptable carrier and, in addition, if desired, may include other medicinal agents, pharmaceutical agents, carriers, adjuvants, diluents, etc. Parental administration, if used, is generally characterized by injection. Injectables can be prepared in conventional forms, either as liquid solutions or suspensions, solid forms suitable for solution or suspension in liquid prior to injection, or as emulsions. Dosages will depend upon the mode of administration, the disease or condition to be treated, and the individual subject's condition, but will be that dosage typical for and used in administration of other AAV vectors, such as AAV2 vectors. Often a single dose can be sufficient; however, the dose can be repeated if desirable. Administration methods for gene delivery to the cochlea are routine and are described in Jero, J. et al. (Gene Ther. 2001 Mar. 20; 12(5):539-48) and Staecker H, et al. (Acta Otolaryngol. 2001 January; 121(2):157-63), both references herein incorporated by reference for these methods.

Administration methods can be used to treat brain disorders such as Parkinson's disease, Alzheimer's disease, and demyelination disease. Other diseases that can be treated by these methods include metabolic disorders such as musculoskeletal diseases, cardiovascular disease, cancer, and autoimmune disorders.

Administration of this recombinant BAAV virion to the cell can be accomplished by any means, including simply contacting the particle, optionally contained in a desired liquid such as tissue culture medium, or a buffered saline solution, with the cells. The virion can be allowed to remain in contact with the cells for any desired length of time, and typically the virion is administered and allowed to remain indefinitely. For such in vitro methods, the virion can be administered to the cell by standard viral transduction methods, as known in the art and as exemplified herein. Titers of virus to administer can vary, particularly depending upon the cell type, but will be typical of that used for AAV transduction in general which is well known in the art. Additionally the titers used to transduce the particular cells in the present examples can be utilized.

The cells that can be transduced by the present recombinant BAAV virion can include any desired cell, such as the following cells and cells derived from the following tissues, human as well as other mammalian tissues, such as primate, horse, sheep, goat, pig, dog, rat, and mouse and avian species: Adipocytes, Adenocyte, Adrenal cortex, Amnion, Aorta, Ascites, Astrocyte, Bladder, Bone, Bone marrow, Brain, Breast, Bronchus, Cardiac muscle, Cecum, Cervix, Chorion, Cochlear, Colon, Conjunctiva, Connective tissue, Cornea, Dermis, Duodenum, Embryonic stem cells, Endometrium, Endothelium, Endothelial cells, Epithelial tissue, Epithelial cells, Epidermis, Esophagus, Eye, Fascia, Fibroblasts, Foreskin, Gastric, Glial cells, Glioblast, Gonad, Hepatic cells, Histocyte, Hair cells in the inner ear, auditory (organ of Corti) sensory epithelia, vestibular sensory epithelia, Ileum, Intestine, small Intestine, Jejunum, Keratinocytes, Kidney, Larynx, Leukocytes, Lipocyte, Liver, Lung, Lymph node, Lymphoblast, Lymphocytes, Macrophages, Mammary alveolar nodule, Mammary gland, Mastocyte, Maxilla, Melanocytes, Mesenchymal, Monocytes, Mouth, Myelin, Myoblasts Nervous tissue, Neuroblast, Neurons, Neuroglia, Osteoblasts, Osteogenic cells, Ovary, Palate, Pancreas, Papilloma, Peritoneum, Pituicytes, Pharynx, Placenta, Plasma cells, Pleura, Prostate, Rectum, Salivary gland, Skeletal muscle, Skin, Smooth muscle, Somatic, Spleen, Squamous, Stem cells, Stomach, Submandibular gland, Submaxillary gland, Synoviocytes, Testis, Thymus, Thyroid, Trabeculae, Trachea, Turbinate, Umbilical cord, Ureter, Uterus, and vestibular hair cells.

The cell of the provided methods can be an inner ear epithelial cell. Thus, the cell of the provided method can be an inner ear hair cell. The cell of the provided methods can be an inner or outer hair cell of the organ of Corti or a vestibular hair cell. The cell of the provided methods can be an inner ear supporting cell such as Hensen's, phalangal, interdental, or vestibular supporting cells.

The cell of the provided method can be an airway epithelial cell. The cell of the provided method can be a columnar, goblet or basal cell.

The cell of the provided method can be a cell of the submandibular gland. The cell of the provided method can be a ductal or acinar cell.

Provided are recombinant vectors based on BAAV. Such vectors may be useful for transducing erythroid progenitor cells or cells resistant to transduction by other serotypes of AAV. These vectors may also be useful for transducing cells with a nucleic acid of interest in order to produce cell lines that could be used to screen for agents that interact with the gene product of the nucleic acid of interest. In addition to transduction of other cell types, transduction of erythroid cells would be useful for the treatment of cancer and genetic diseases which can be corrected by bone marrow transplants using matched donors. Some examples of this type of treatment include, but are not limited to, the introduction of a therapeutic gene such as genes encoding interferons, interleukins, tumor necrosis factors, adenosine deaminase, cellular growth factors such as lymphokines, blood coagulation factors such as factor VIII and IX, cholesterol metabolism uptake and transport protein such as EpoE and LDL receptor, and antisense sequences to inhibit viral replication of, for example, hepatitis or HIV.

Provided is a vector, comprising the BAAV virus as well as BAAV viral particles. While BAAV is similar to AAV1-8, the viruses are found herein to be physically and genetically distinct. These differences endow BAAV with some unique advantages, which better suit it as a vector for gene therapy.

Furthermore, as shown herein, BAAV capsid protein is distinct from AAV1-8 and AAAV capsid protein and exhibits different tissue tropism. AAV1-8 and BAAV likely utilize distinct cellular receptors. AAV1-8 and BAAV are serologically distinct and humans are not reported to have neutralizing antibodies to BAAV, thus in a gene therapy or gene transfer application, BAAV would allow for transduction of a patient who already possess neutralizing antibodies to AAV1-8 either as a result of natural immunological defense or from prior exposure to AAV1-8 vectors.

Vector System

Provided herein is a vector system for producing infectious virus particles having a characteristic of BAAV. As used herein, a "vector system" is a combination of one or more vectors that, when added to an appropriate cell system, can produce a recombinant BAAV virion, as provided herein.

The provided vector system can comprise: at least one vector comprising a nucleic acid selected from the group consisting of a pair of BAAV ITRs, a nucleic acid encoding a BAAV capsid protein, and a nucleic acid encoding a BAAV Rep protein.

The vector system can comprise one or more unique vectors. Thus, the vector system can comprise, for example, 1, 2, 3, 4, 5, or 6 unique vectors.

In a two-vector vector system, the first vector can comprise a nucleic acid encoding a BAAV Rep protein and the second vector can comprise a pair of BAAV ITRs. Alternatively, the first vector can comprise a nucleic acid encoding a BAAV capsid protein and a nucleic acid encoding a BAAV Rep protein and the second vector can comprise a pair of BAAV ITRs.

In another two-vector vector system, the first vector can comprise a nucleic acid encoding a BAAV capsid protein and the second vector can comprise a pair of AAV ITRs. The AAV ITRs of the second vector can be a pair of AAV1 ITRs. The AAV inverted terminal repeats can be a pair of AAV2 ITRs. The AAV ITRs can be a pair of AAV3 ITRs. The AAV ITRs can be a pair of AAV4 ITRs. The AAV ITRs can be a pair of AAV5 ITRs. The AAV ITRs can be a pair of AAV6 ITRs. The AAV ITRs can be a pair of AAV7 ITRs. The AAV ITRs can be a pair of AAV8 ITRs. The AAV ITRs can be a pair of AAAV ITRs. The AAV ITRs can be a pair of BAAV ITRs.

The first vector can further comprise a nucleic acid encoding an AAV Rep protein. The AAV Rep protein can be AAV1 Rep protein. The AAV Rep protein can be AAV2 Rep protein. The AAV Rep protein can be AAV3 Rep protein. The AAV Rep protein can be AAV4 Rep protein. The AAV Rep protein can be AAV5 Rep protein. The AAV Rep protein can be AAV6 Rep protein. The AAV Rep protein can be AAV7 Rep protein. The AAV Rep protein can be AAV8 Rep protein. The AAV Rep protein can be AAAV Rep protein. The AAV Rep protein can be BAAV Rep protein. The Rep proteins can be encoded by the nucleic acid sequence SEQ ID NOS:XX.

In another two-vector system, the first vector can comprise a nucleic acid encoding an AAV capsid protein and the second vector can comprise a pair of BAAV ITRs. The capsid protein can be an AAV1 capsid protein. The capsid protein can be an AAV2 capsid protein. The capsid protein can be an AAV3 capsid protein. The capsid protein can be an AAV4 capsid protein. The capsid protein can be an AAV5 capsid protein. The capsid protein can be an AAV6 capsid protein. The capsid protein can be a AAAV Rep protein. The capsid protein can be a BAAV Rep protein.

The second vector can further comprise a promoter between the ITRs. The promoter can be AAV2 p5 promoter. The promoter can be AAV5 p5 promoter. The promoter can be BAAV p5 promoter. More specifically, the BAAV p5 promoter can be in about the same location in SEQ ID NO: 1 as the AAV2 p5 promoter, in the corresponding AAV2 published sequence. Additionally, the p5 promoter may be enhanced by nucleotides 1-173 of SEQ ID NO:1. Furthermore, smaller fragments of p5 promoter that retain promoter activity can readily be determined by standard procedures including, for example, constructing a series of deletions in the p5 promoter, linking the deletion to a reporter gene, and determining whether the reporter gene is expressed, i.e., transcribed and/or translated. The promoter can be the BAAV p19 promoter (SEQ ID NO: 16). The promoter can be the BAAV p40 promoter (SEQ ID NO: 17). The promoter can be a promoter of any of the AAV serotypes. The promoter can be a constitutive promoter. Thus, the promoter can be CMV. The promoter can be RSV. The promoter can be LTR. The promoter can be eF1. The promoter can be beta actin promoter. The promoter can be a tissue specific promoter. The promoter can be an inducible promoter. The promoter can further be functionally linked to an exogenous nucleic acid.

Further provided is any of the disclosed vectors of the vector systems encapsidated into an AAV particle. The AAV particle can be an AAV1 virus particle comprising at least one AAV1 capsid protein. The AAV particle can be an AAV2 virus particle comprising at least one AAV2 capsid protein. The AAV particle can be an AAV3 virus particle comprising at least one AAV3 capsid protein. The AAV particle can be an AAV4 virus particle comprising at least one AAV4 capsid protein. The AAV particle can be an AAV5 virus particle comprising at least one AAV5 capsid protein. The AAV particle can be an AAV6 virus particle comprising at least one AAV6 capsid protein. The AAV particle can be an AAV7 virus particle comprising at least one AAV7 capsid protein. The AAV particle can be an AAV8 virus particle comprising at least one AAV8 capsid protein. The AAV particle can be an AAAV virus particle comprising at least one AAAV capsid protein. The AAV particle can be a BAAV virus particle comprising at least one BAAV capsid protein. The AAV particle can be a chimeric capsid virus particle (described above) comprising a capsid protein from more than one serotype of AAV.

AAV Transcytosis

Disclosed is a method of delivering an exogenous nucleic acid across an epithelial barrier, comprising delivering to the epithelial barrier an AAV vector, comprising the exogenous nucleic acid. In one aspect of the method, the AAV is AAV4, AAV5, or BAAV. In another aspect of the method, the epithelial cells are in the gut, lung, genitourinary tract, kidney, blood vessels or brain. In another aspect of the method, the epithelial cells can be selected from a group consisting of bronchial, alveolar, tracheal or upper airway epithelial cells; absorptive enterocytes or M cells; endometrial or urinary epithelial cells; renal collecting duct or proximal tubule epithelial cells; cerebral microvascular endothelial cells or Choroidal Plexus epithelial cells.

Further disclosed is a method of transcytosing epithelial cells of a human subject, comprising administering to the subject an AAV vector comprising an exogenous nucleic acid. In one aspect of the method, the vector is AAV4, AAV5, or BAAV. In another aspect of the method, the epithelial cells are selected from a group consisting of bronchial, alveolar, tracheal or upper airway epithelial cells; absorptive enterocytes or M cells; endometrial or urinary epithelial cells; renal collecting duct or proximal tubule epithelial cells; cerebral microvascular endothelial cells or Choroidal Plexus epithelial cells.

Further contemplated are methods for the delivery of molecules across epithelial cell barriers comprising coupling the molecules to non-recombinant (wild-type) AAV capsids or particles. In one aspect, the molecules are radioligands or enzymes.

The term "adeno-associated virus (AAV)" is used herein to refer to a genus of viruses in the family Parvoviridae which are all defective viruses (unable to replicate by themselves) and depend on the co-infection of their host cell by other, nondefective viruses to help them replicate.

The term "transcytosis" is used herein to mean the transport of macromolecular cargo from one side of a cell to the other within a membrane-bounded carrier(s). Tuma and Hubbard provided a review of transcytosis (Tuma P L and Hubbard A L. 2003. Physiol Rev. 83:871-932), herein incorporated by reference for its teaching regarding the nature and uses for trancytosis. Transcytosis is a strategy used by multicellular organisms to selectively move material between two different environments while maintaining the distinct compositions of those environments. N. Simionescu was the first to coin the term transcytosis to describe the vectorial transfer of macromolecular cargo within the plasmalemmal vesicles from the circulation across capillary endothelial cells to the interstitium of tissues. During this same period, another type of transcytosis was being discovered. Immunologists comparing the different types of immunoglobulins found in various secretions (e.g., serum, milk, saliva, and the intestinal lumen) speculated that the form of IgA found in external secretions (called secretory IgA, due to the presence of an additional protein component) was selectively transported across the epithelial cell barrier. More is known about transcytosis as it is expressed in epithelial tissues, which form cellular barriers between two environments. In this polarized cell type, net movement of material can be in either direction, apical to basolateral or the reverse, depending on the cargo and particular cellular context of the process. However, transcytosis is not restricted to only epithelial cells.

Since the 19th century dye experiments of Ehrlich, the brain has been known as a "privileged" organ where access is tightly regulated so that the environment remains chemically stable. The two principal gatekeepers of the brain are the cerebral capillary endothelium and the cuboidal epithelial cells of the choroid plexus. These cellular barriers are specialized for the passage of different nutrients from the blood. The capillaries move nutrients that are required rapidly and in large quantities, such as glucose and amino acids. These small molecules are transported by membrane carriers using facilitated diffusion. The choroid plexus supplies nutrients that are required less acutely and in lower quantities. These are folate and other vitamins, ascorbate, and deoxyribonucleotides.

There are two epithelial cells that participate in transcytosis in the intestine, M cells and enterocytes (adsorptive columnar cells). These cells are very different from one another and the capillary endothelial cell. Depending on the species, M cells comprise a variable but small percentage of the epithelia overlying organized mucosal-associated lymphoid tissue, making them a very minor cell population in the gastrointestinal tract. The transcytotic route across M cells is thought to be part of the mechanism by which antigens are routinely sampled along the entire mucosal surface. Not surprisingly, numerous pathogens have evolved mechanisms to exploit the transcytotic process as a means to invade and disseminate before a strong enough immune response can be mounted.

Absorptive enterocytes are simple columnar cells with several apical features in addition to their brush borders. Clathrin-coated pits are present at the base of microvilli, and a thick glycocalyx composed of integral membrane proteins with glycosaminoglycan side chains emanates from the microvillar membrane. This latter structural feature as well as the rigidity of the microvilli are thought to prohibit microorganisms from attaching and invading enterocytes. The intracellular organization of these columnar epithelial cells is also polarized, with basally located nuclei, supranuclear Golgi, and an abundance of pleiomorphic membrane compartments underlying the terminal web of the brush border. The basolateral-to-apical length of this cell is ~20 versus 0.2 µm for a capillary endothelial cell, making the transcytotic route across enterocytes potentially much longer. Furthermore, microtubules are an important structural element of the transcytotic pathway in enterocytes, but not in M or endothelial cells.

Transcytosis also occurs in the upper regions of the respiratory tract and has been demonstrated with two vector systems, pIgA-R and FcRn, but others could exist. Secretory IgA is a known constituent of the lung's immune defense system, with bronchial epithelial cells carrying out basolateral-to-apical transport of dIgA, which is secreted by local plasma cells in underlying lymphoid tissue. Albumin, which is found in lung fluid, is endocytosed specifically at the apical surface of airway epithelia but is then subsequently degraded. At the alveolar level, the question of whether albumin is transcytosed intact is uncertain.

The term "epithelia" is used herein to refer to cells which are linked tightly together by intercellular junctions to form a planar sheet. These sheets of cells form a barrier between two compartments. Epithelia therefore line all surfaces and cavities (including skin, peritoneum, linings of the intestine, airways, genitourinary tracts, glands, and blood vessels.

An epithelium has a free or apical surface facing the environment, or lumen of a cavity, and a basal surface facing the underlying connective tissue. The boundary between the basal surface of an epithelium and the underlying connective tissue is usually very sharp, and is the site where the basal lamina (BL) is present. Most BL are too thin to be seen with the light microscope. However, the BL, together with a thin layer of connective tissue, is often times seen at the epithelial/connective tissue interface. This composite layer, visible with the light microscope, was initially called the Basement Membrane. Application of the electron microscope revealed that, in most cases, this Basement Membrane actually consisted of the true basal lamina (lamina lucida plus lamina densa), along with a layer of adherent connective tissue.

For convenience of description, epithelia are classified into different types based on the number of cell layers and the cell shape.

Epithelia which are 1 cell layer thick are called "simple" epithelia. Thus, each cell rests on the basal lamina, but also has a surface facing the lumen/outside world. Epithelia which are 2 or more cell layers thick are called "stratified" epithelia. In stratified epithelia, the basal layer of cells rests on the basal lamina, but subsequent layers do not, and are simply stacked on top of the basal layer. The cells of the most superficial layer have a free surface. "squamous" cells are very flat, like a fried egg, where the yolk is the nucleus. The nucleus is distinctly flattened, the cell is often so thin that this flattened nucleus bulges the cell surface outward. "cuboidal" cells range from true cuboidal where the cell is about as high as it is wide, to a flattened cuboidal where the cell is wider than high. In cuboidal cells the nucleus is usually round, and not flattened as in squamous. "columnar" cells are 2 or more times as high as wide. Nucleus is usually elongated in the long axis of the cell.

Squamous cells form the lining of cavities such as the mouth, blood vessels, heart and lungs and make up the outer layers of the skin. Cuboidal epithelium is found in glands and in the lining of the kidney tubules as well as in the ducts of the glands. They also constitute the germinal epithelium which produces the egg cells in the female ovary and the sperm cells in the male testes. Columnar epithelium forms the lining of the stomach and intestines. Some columnar cells are specialized for sensory reception such as in the nose, ears and the taste buds of the tongue.

Ciliated columnar epithelial cells posses fine hair-like outgrowths, cilia on their free surfaces. These cilia are capable of rapid, rhythmic, wavelike beatings in a certain direction. Ciliated epithelium is usually found in the air passages like the nose. It is also found in the uterus and Fallopian tubes of females.

Columnar epithelium with goblet cells is called glandular epithelium. Some parts of the glandular epithelium consist of such a large number of goblet cells that there are only a few normal epithelial cells left. Columnar and cuboidal epithelial cells often become specialized as gland cells which are capable of synthesizing and secreting certain substances such as enzymes, hormones, milk, mucus, sweat, wax and saliva. Unicellular glands consist of single, isolated glandular cells such as the goblet cells. Sometimes a portion of the epithelial tissue becomes invaginated and a multicellular gland is formed. Multicellular glands are composed of clusters of cells. Most glands are multicellular including the salivary glands.

Where body linings have to withstand wear and tear, the epithelia are composed of several layers of cells and are then called compound or stratified epithelium. The top cells are flat and scaly and it may or may not be keratinized (i.e. containing a tough, resistant protein called keratin). The mammalian skin is an example of dry, keratinized, stratified epithelium. The lining of the mouth cavity is an example of an unkeratinized, stratified epithelium.

The use of in vitro cell models to study transcytosis has many advantages over in vivo systems. First, variation among animals is eliminated, as is the confounding issue of cargo possibly being modified or endocytosed by cell types other than the one under study. Moreover, in vitro systems can be manipulated in ways not possible in vivo, allowing investigators to measure the effects of different variables (e.g., temperatures, pharmacological agents, etc.) with greater precision and to explore the molecular mechanisms of transcytosis.

The integrity of the monolayer is obviously vital to every study of transcytosis, and there are different methods for assessing it. Transepithelial electrical resistance (TER) measurements are commonly used as an indication of tight junction integrity in a monolayer, and commercial instruments are available for these measurements.

Caco-2 cells, human primary colon carcinoma cells, are a well studied model of intestinal absorptive enterocytes. They are the most commonly used intestinal cell line because they differentiate furthest along the cryptto-villus axis and are the easiest to transfect. Caco-2 cells have been especially used to model transcytosis of bacteria, which can cross barrier epithelia in the gut and brain (Zhang J R, et al., 2000. Cell 102(6):827-37), incorporated herein by reference.

There is little evidence for in vivo transcytosis of macromolecular cargo in kidney. Nonetheless, MDCK cells, which are derived from dog kidney, are the most-studied epithelial cell model and have been used extensively to study transcytosis. These cells were originally developed by nephrologists for permeability and electrical studies. Their subsequent use by cell biologists for studies of the formation of tight junctions, establishment of polarity, and vesicle traffic have popularized MDCK cells. An advantage is that MDCK cells are easily cultured, easily transfected, and become polarized 3-5 days after seeding. They were used in the now classical studies showing that enveloped viruses bud in a polarized fashion and that the newly synthesized viral membrane glycoproteins are targeted directly from the TGN to the appropriate PM domain. Furthermore, much of the current understanding of the IgA transcytotic pathway and the sorting signals in the pIgA-R comes from the elegant studies performed in MDCK cells. Two MDCK strains with very different features were identified some time ago. The MDCK I cell has a high TER and characteristics reminiscent of the renal collecting duct, whereas the more commonly used MDCK II strain, whose TER is one order of magnitude lower than that of MDCK I cells, has phenotypic features closer to those of the renal proximal tubule.

Both primary cells and cell lines, alone and in coculture with endothelial cells, are being used to study transcytosis in the lung. Clonetics bronchial/tracheal epithelial cell systems contain normal human bronchial/treacheal epithelial cells. This cell system has been used for experimental applications in cancer research, respiratory disease, cellular function and differentiation.

The Clonetics® bovine Brain Microvascular Endothelial Cell System (bMVEC-B) is a model of the "Blood Brain Barrier". The system is designed to significantly improve a researcher's ability to study active and passive transport of drugs across the blood brain barrier, to study brain endothelial cell tight junctions, and to study the basic biology of brain microvascular endothelial cells (Schinket A H, 1999. Advanced Drug Delivery Reviews 36:179-194; Tsukita S. et al., 1998. Molecular dissection of tight junctions:occluding and ZO-1 in Introduction to the Blood—Brain Barrier. Edited by William M Partridge; Inglis et al., 2004. Brain Research 998: 218-229), each of which is incorporated by reference for its teaching of in vitro endothelial cell modeling of the blood-brain barrier.

Endometrial cells form an important barrier layer in the genitourinary tract. The cells used to model this system were developed by Kyo et al. and are derived from primary cells immortalized by the addition of the papillomiavirus E6/E7 genes and human telomerase reverse transcriptase. The isolated cells have a normal chromosomes and retain their responsiveness to sex-steriod hormones, exhibit glandular structure on three dimensional culture, and lack a transformed phenotype (Kyo S, et al. Am J. Pathol., 2003. 163(6):2259-69), incorporated herein by reference for its teaching of this endometrial model.

The provided BAAV particles and virions combine the known advantages of AAVs as vectors with distinct tropisms unique to BAAV viral particles. A further advantage of the provided compositions and methods is the ability of BAAV virions to deliver nucleic acids across epithelial barriers. Thus, the compositions and methods provided herein can be used to deliver nucleic acids to cells or cells in a subject. The provided compositions and methods can be used for the therapeutic delivery of nucleic acids to cells in a subject for the treatment of disease. The provided compositions and methods can further be used in scientific, medical or veterinary research. For example, a provided vector system can be used to deliver an exogenous nucleic acid to a cell to evaluate its interaction with other molecules in the cell. The provided vector systems can, for example, be used to study signal transduction, metabolic pathways, apoptosis, or cell cycle/growth in cells wherein the vector system is used to deliver nucleic acids to either overexpress or inhibit, e.g. by siRNAs, components of these pathways. The provided compositions and methods can further be used in vaccine production in avian or insect cultures. The provided compositions and methods can further be used in the preparation of a medicament for the delivery of a nucleic acid to a cell or cell in a subject.

The use of AAVs to deliver genes to the lung by transcytosis would be of benefit in genetic diseases like cystic fibrosis, pseudohypoaldosteronism, and immotile cilia syndrome. Furthermore, delivering genes to the lung would be of impact in several non-genetic diseases. For example, delivering genes that make antibiotic like peptides to the cells underlying the epithelia would be useful to prevent or treat bronchitis; delivering genes that make growth factors would be of value in common diseases like chronic bronchitis. Also, AAVs could be used to deliver genes that may play a role in asthma, like IL-10, or antibodies to IgE and interleukins. The use of an AAV vector to deliver genes through the alveolar epithelia would be of benefit in genetic diseases like alpha-1-antitrypsin deficiency. Furthermore, delivering genes through the alveolar epithelia would be of significance in several pulmonary non-genetic diseases. For example, delivering genes that make antibiotic like peptides would be useful to prevent or treat pneumonia (perhaps of antibiotic-resistant organisms); delivering genes that make growth factors would be of value in emphysema; delivering genes that over-express the epithelial sodium channel or the Na-K ATPase could be used to treat cardiogenic and non-cardiogenic pulmonary edema; delivering genes that have an anti-fibrosis effect like interferon for pulmonary fibrosis would also be useful. Also, AAVs could be used to deliver genes that may have a systemic effect like anti-hypertension drugs, insulin, coagulation factors, antibiotics, growth factors, hormones and others.

The use of AAVs to deliver genes to the central nervous system (CNS)/brain by transcytosis would be of benefit in neurological diseases, including Alzheimer's Disease, Parkinson's Disease, Huntington's Disease, Tourette Syndrome, schizophrenia, mania, dementia, paranoia, obsessive compulsive disorder, panic disorder, learning disabilities, ALS, triplet expansions diseases, psychoses, autism, lysosomal storage diseases, Gaucher's disease, Hurler's disease, Krabbe's disease, battens disease, and altered behaviors (e.g., disorders in feeding, sleep patterns, balance, and perception).

The use of AAVs to deliver genes to the gastrointestinal system/gut by transcytosis would be of benefit in treatment of diseases and/or Gastrointestinal Disorders such as colon cancers, inflammatory bowel disease, diabetes, or Crohn's disease.

The use of AAVs to deliver genes to the genitourinary system by transcytosis would be of benefit in treatment of diseases of the female reproductive tract, molecular defects in implantation disorders, and gynecological cancers. These methods would also have contraceptive applications.

The use of AAVs to deliver genes to the kidney by transcytosis would be of benefit in treatment of inherited renal disorders such as polycystic kidney disease, Alport's syndrome, hereditary nephritis, primary hyperoxaluria, and cystinuria.

The use of AAVs for wide-spread delivery of genes across blood vessels into the muscle would be of benefit in neuromuscular diseases like muscular dystrophy and Cardiovascular Disorders such as heart disease, restenosis, atherosclerosis, myocarditis, stoke, angina, or thrombosis.

The use of AAVs for wide-spread delivery of genes across blood vessels into any/all tissues of a subject would be of benefit in the treatment of certain cancers (e.g., gastric, ovarian, lung, bladder, liver, and breast).

The use of AAVs for wide-spread delivery of genes across blood vessels into any/all tissues of a subject would be of benefit in the treatment of certain inflammatory disorders, including, but not limited to, adrenalitis, alveolitis, angiocholecystitis, appendicitis, balanitis, blepharitis, bronchitis, bursitis, carditis, cellulitis, cervicitis, cholecystitis, chorditis, cochlitis, colitis, conjunctivitis, cystitis, dermatitis, diverticulitis, encephalitis, endocarditis, esophagitis, eustachitis, fibrositis, folliculitis, gastritis, gastroenteritis, gingivitis, glossitis, hepatosplenitis, keratitis, labyrinthitis, laryngitis, lymphangitis, mastitis, media otitis, meningitis, metritis, mucitis, myocarditis, myosititis, myringitis, nephritis, neuritis, orchitis, osteochondritis, otitis, pericarditis, peritendonitis, peritonitis, pharyngitis, phlebitis, poliomyelitis, prostatitis, pulpitis, retinitis, rhinitis, salpingitis, scleritis, sclerochoroiditis, scrotitis, sinusitis, spondylitis, steatitis, stomatitis, synovitis, syringitis, tendonitis, tonsillitis, urethritis, and vaginitis; and disorders that are characterized by inflammation such as hepatitis, rheumatoid arthritis, gout, trauma, pancreatitis, sarcoidosis, dermatitis, renal ischemia-reperfusion injury, Grave's disease, systemic lupus erythematosus, diabetes mellitus, and allogenic transplant rejection.

The use of AAVs for wide-spread delivery of genes across blood vessels into any/all tissues of a subject would be of benefit in the treatment of other diseases, syndromes and conditions, such as adenosine deaminase deficiency, sickle cell deficiency, thalassemia, hemophilia, diabetes, phenylketonuria, growth disorders, and defects of the immune system.

The present invention is more particularly described in the following examples which are intended as illustrative only since numerous modifications and variations therein will be apparent to those skilled in the art.

Example 1

Isolation, Subcloning, Sequencing and Characterization of BAAV

To understand the nature of BAAV virus and to determine its usefulness as a vector for gene transfer, it was cloned and sequenced.

Cell Culture and Virus Propagation 293T and COS cells were maintained in DMEM, supplemented with 10% FBS, 2 mM L-glutamine, 100 U/ml penicillin, and 0.1 mg/ml streptomycin. Cancer cell lines indicated in FIG. 1 were cultured in RPMI medium supplemented with 5% FBS, 2 mM L-glutamine, 100 U/ml penicillin, and 0.1 mg/ml streptomycin. MDBK cells were propagated in DMEM supplemented with 5% horse serum, 2 mM L-glutamine, 100 U/ml penicillin, and 0.1 mg/ml streptomycin. Cells were maintained at 37° C. in a 5% $CO_2$ humidified atmosphere.

Bovine Adenovirus Type 1 (ATCC VR-313) and Bovine Adenovirus Type 2 (ATCC VR-313) obtained from ATCC are reported by ATCC to be contaminated with AAV. For virus propagation, MDBK cells were infected with ATCC VR-313 or ATCC VR-314 and cultured for 5 days. At this time, first signs of an adenovirus induced cytopathic effect was observed.

Viral DNA Isolation, Cloning and Sequencing

Viral DNA was isolated from the Bovine Adenovirus Type 1 (ATCC VR-313) and Bovine Adenovirus Type 2 (ATCC VR-313) infected MDBK cells using the High Pure Viral Nucleic Acid Kit (Roche). These DNA samples were assayed for AAV contamination by PCR using the GC Rich PCR Kit (Roche), as described in Katano H, et al. Biotechniques. 2004 April; 36(4):676-80, herein incorporated by reference for its teaching of these methods. Briefly, this method detects the presence of AAV DNA by PCR using degenerative PCR primers, which were shown to amplify a fragment containing sequences of the rep and vp ORF of all known AAV serotypes. PCR using DNA isolated from ATCC VR-313 and ATCC VR-314 as template resulted in the generation of a 1.4 kb amplification product, which was subsequently cloned using the TOPO TA Cloning KIT (Invitrogen) and sequenced with an ABI Prism 3100 Genetic Analyzer (ABI) and FS dye-terminator chemistry (ABI). The obtained sequences showed homology to AAV5 rep ORF and AAV4 cap ORF but were not identical to any known AAV. This result demonstrated that ATCC VR-313 and ATCC VR-314 contained contaminations of an unknown AAV serotype, termed subsequently bovine adeno-associated virus (BAAV). The obtained sequence of BAAV was used to generate PCR primers that bind in the BAAV rep ORF in (−) orientation and in the vp ORF in (+) orientation. PCR using these primers and extrachromosomal DNA of ATCC VR-313 infected MDBK cells (isolated using the Qiagen Mini Prep Kit) resulted in amplification of a BAAV fragment spanning from the vp ORF through the ITR to the rep ORF. The PCR amplification products were subsequently cloned using the TA Cloning KIT (Invitrogen) and sequenced with an ABI Prism 3100 Genetic Analyzer (ABI) and FS dye-terminator chemistry (ABI). ITRs of 2 clones were sequenced by isothermal non-cycling sequencing chemistry using radiolabeled dCTP (Epicentre). For the generation of recombinant particles, a BAAV packaging plasmid was constructed by PCR amplifying a BAAV fragment containing the complete ORF of rep and vp using DNA isolated from ATCC VR-313 and ATCC VR-314 samples as template and inserting this fragment into an expression plasmid under the control of a MMTV promoter resulting in the plasmid pMMTV-BAAV#1-200. 10 clones were sequenced. The plasmids were assayed for the ability to generate recombinant BAAV particles by transfecting 293 T cells with an AAV5-NLS-GFP vector plasmid, pMMTV-BAAV and p449b helper plasmid. 2 days after transfection, cells were lysed by 3 freeze thaw cycles. Cleared lysate was used to infect Cos cells. 2 days after infection, cells were assayed for GFP expression by fluorescent microscopy. pMMTV-BAAV#47 generated highest titers of recombinant BAAV but diverged from the BAAV consensus sequence by 1 nucleotide change. The sequence of pMMTV-BAAV#47 was changed to the consensus sequence using the Quik Change Kit (Clontech) and named pMMTV-BAAV.

Sequence Analysis

Figure 2:
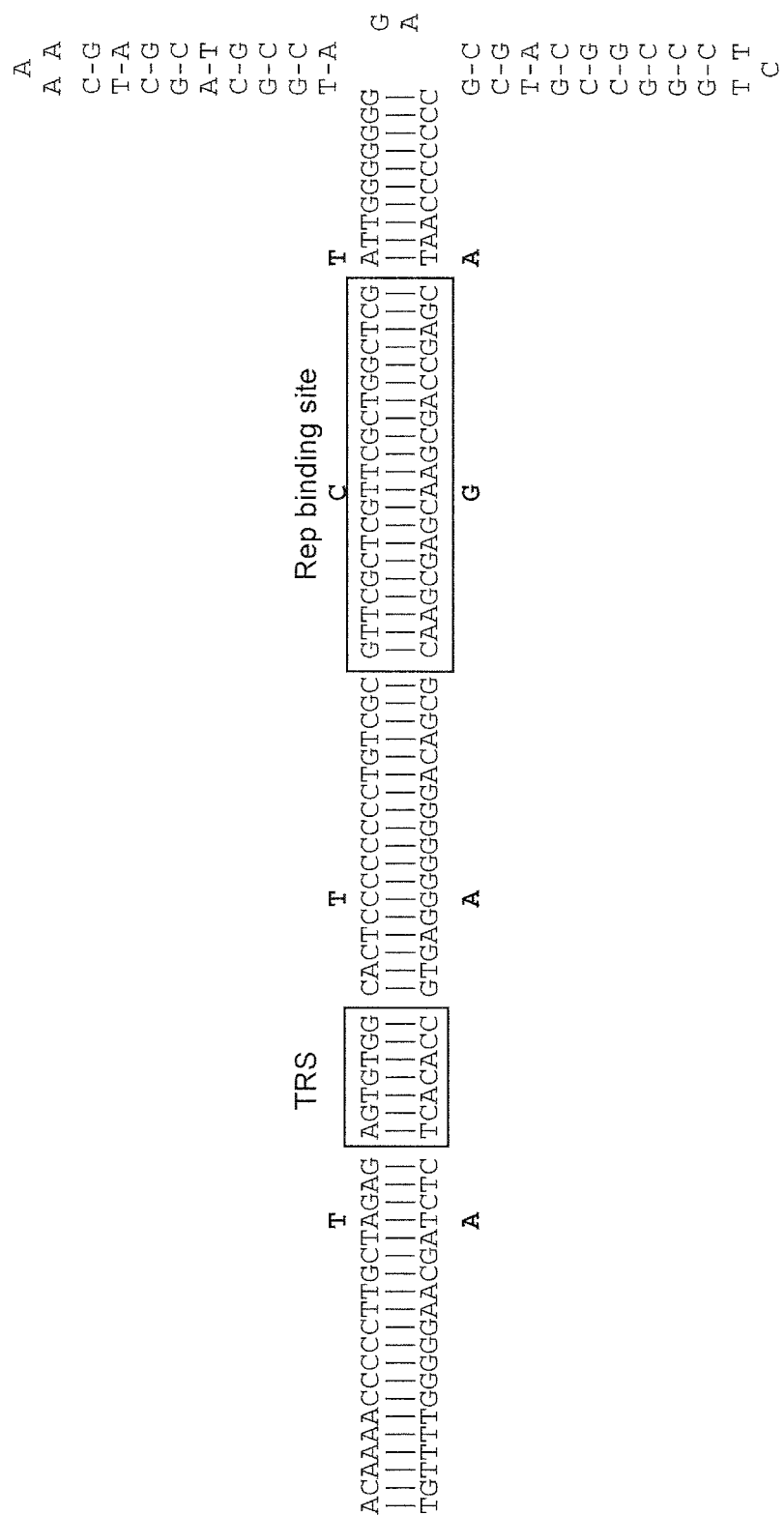
FIG. 2 shows an example of a BAAV ITR (SEQ ID NO:29). The sequence of the ITR is shown in hairpin configuration. The putative Rep binding site (SEQ ID NO:24 and SEQ ID NO:25) and TRS element (SEQ ID NO:14) are boxed. Sequence changes relative to the AAV5 ITR are annotated either above or below the BAAV sequence in bold letters.
Figure 3A:
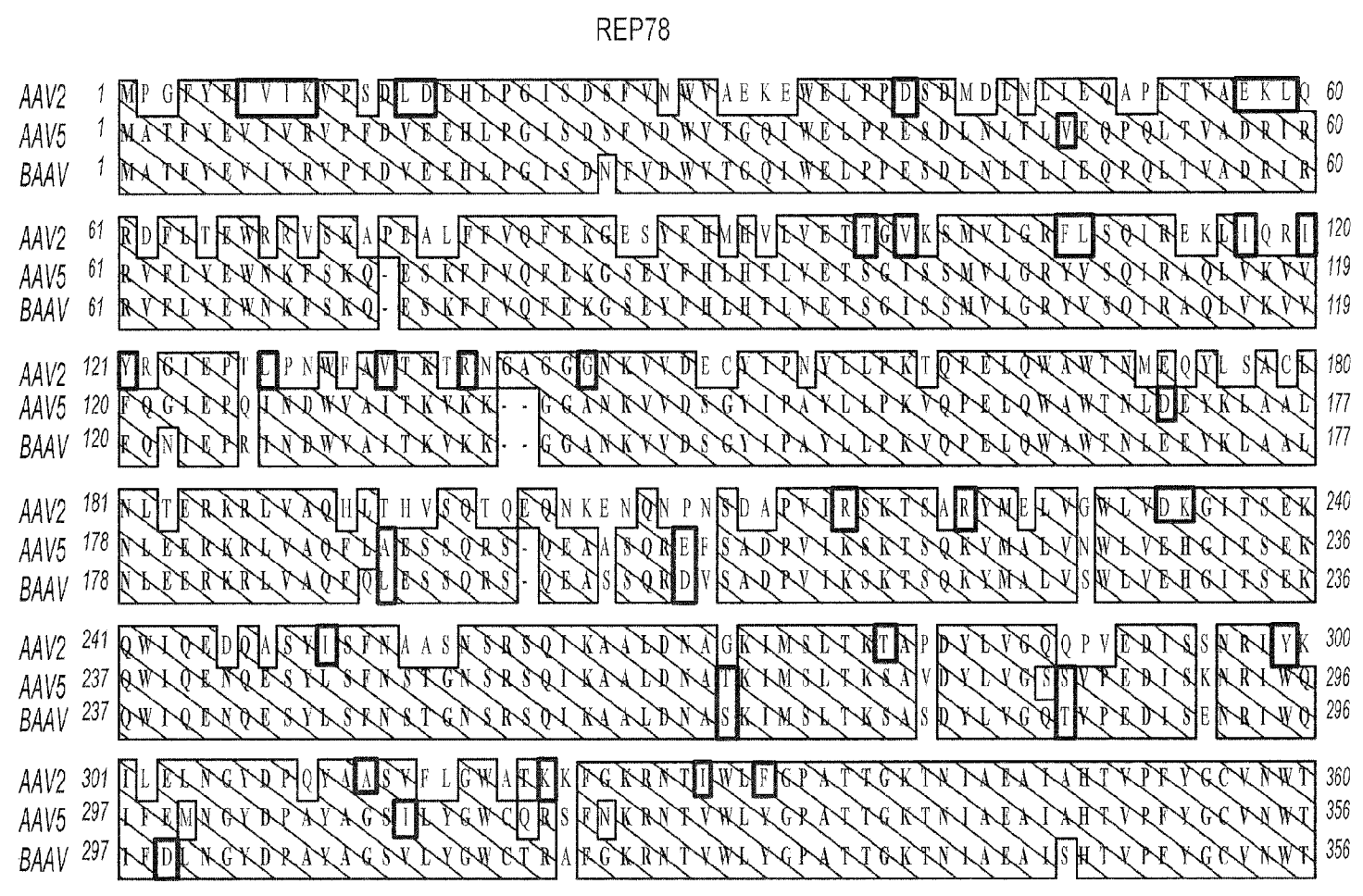
Figure 3A:
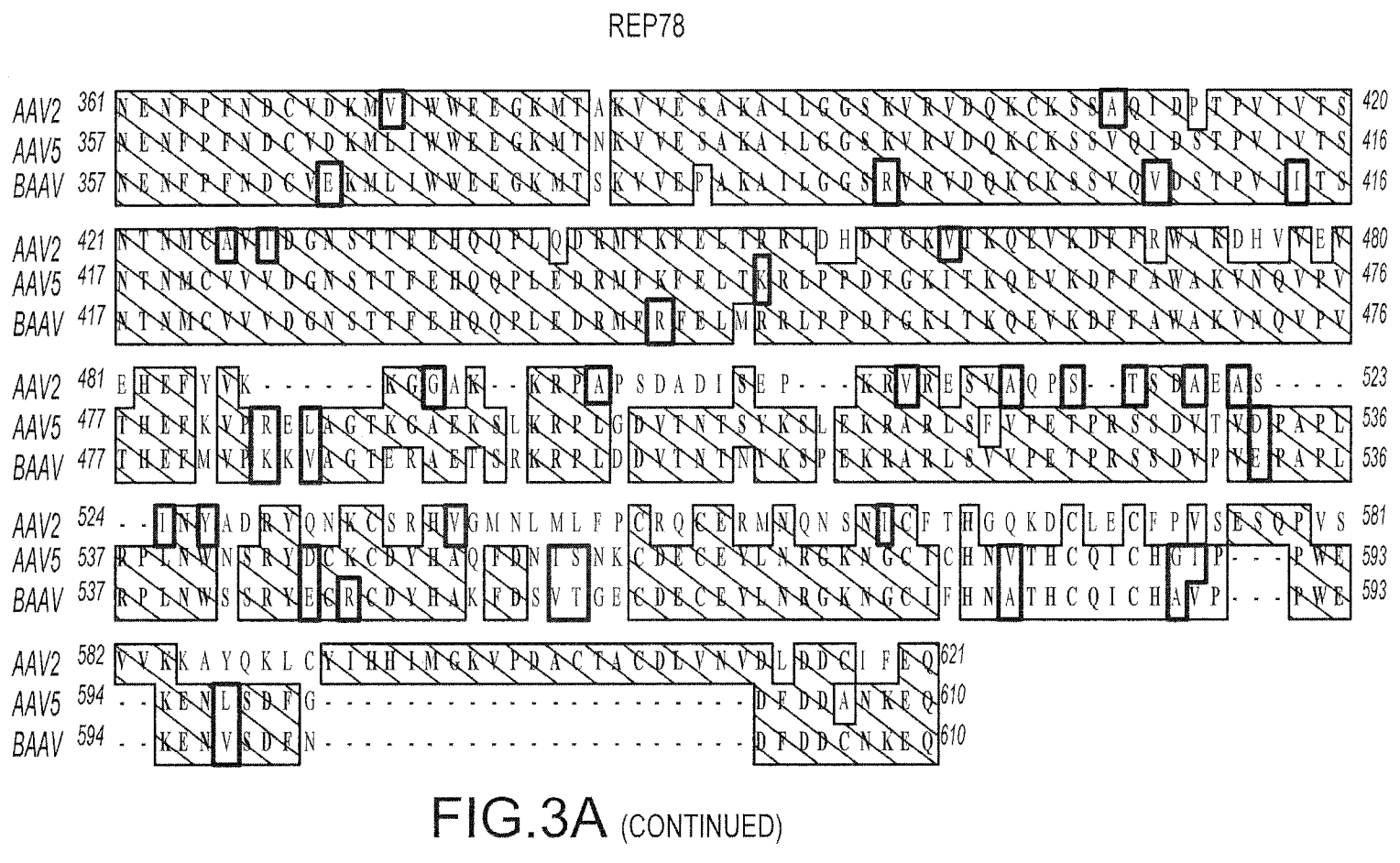
Figure 3B:
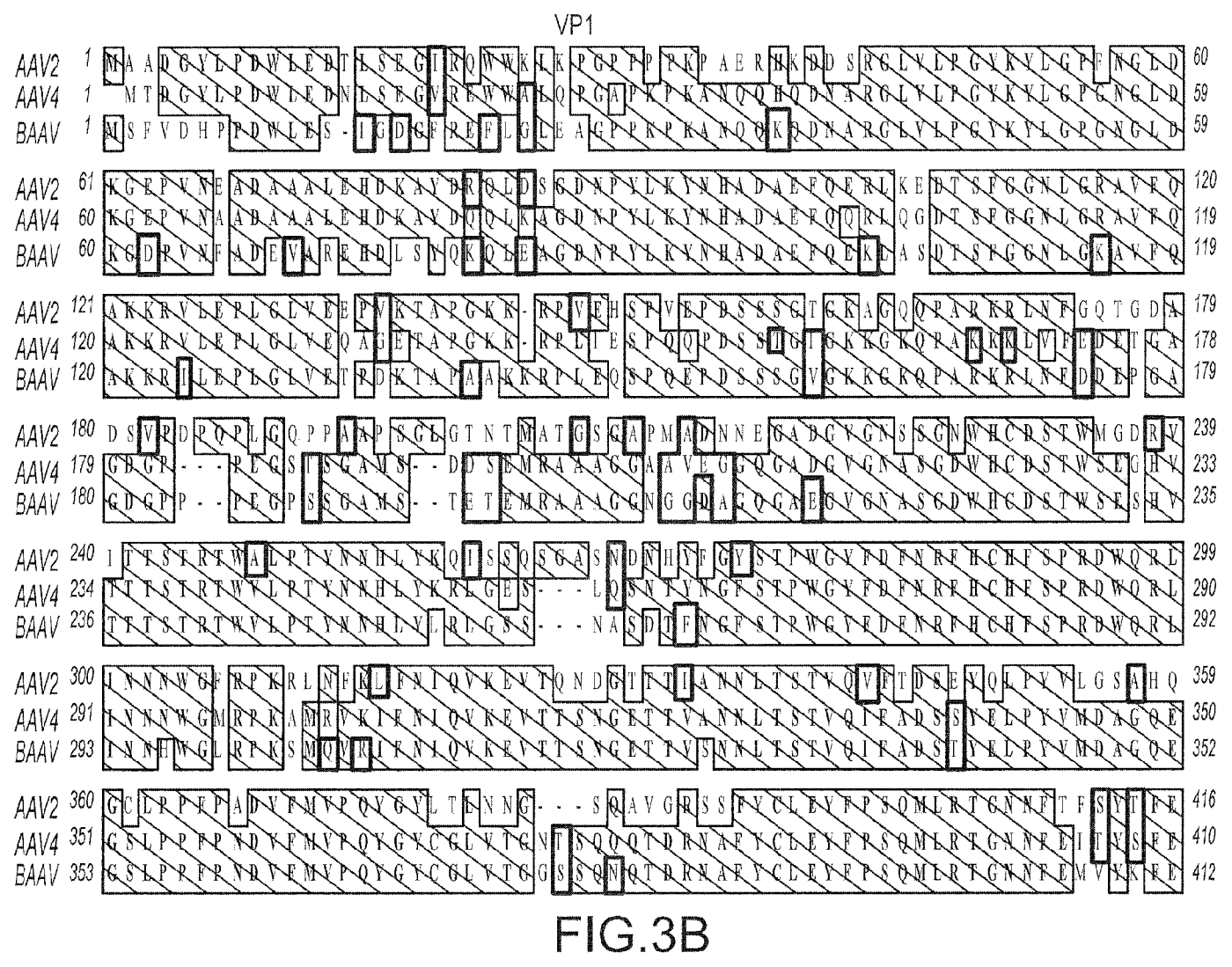
Figure 3B:
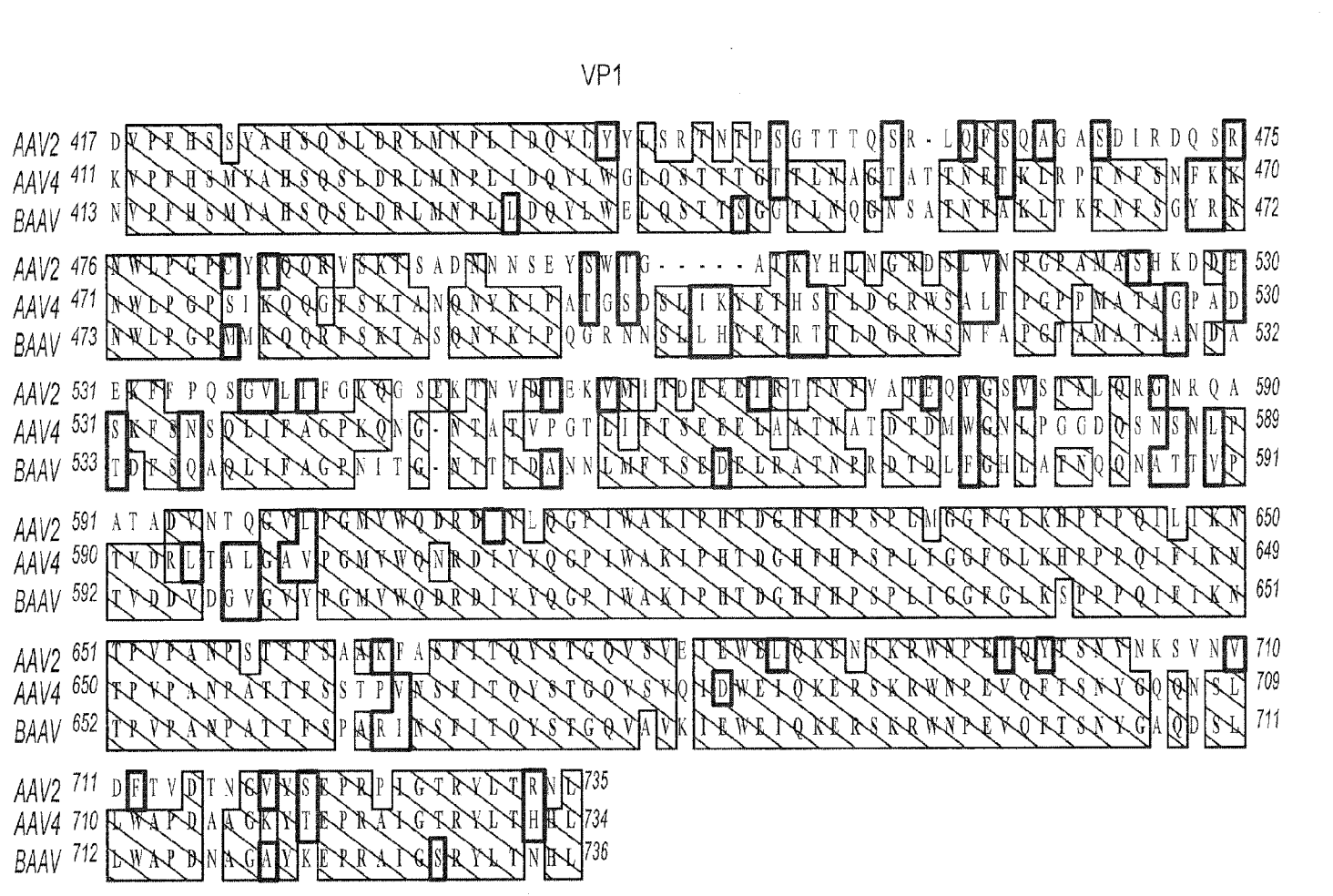
Figure 3C:
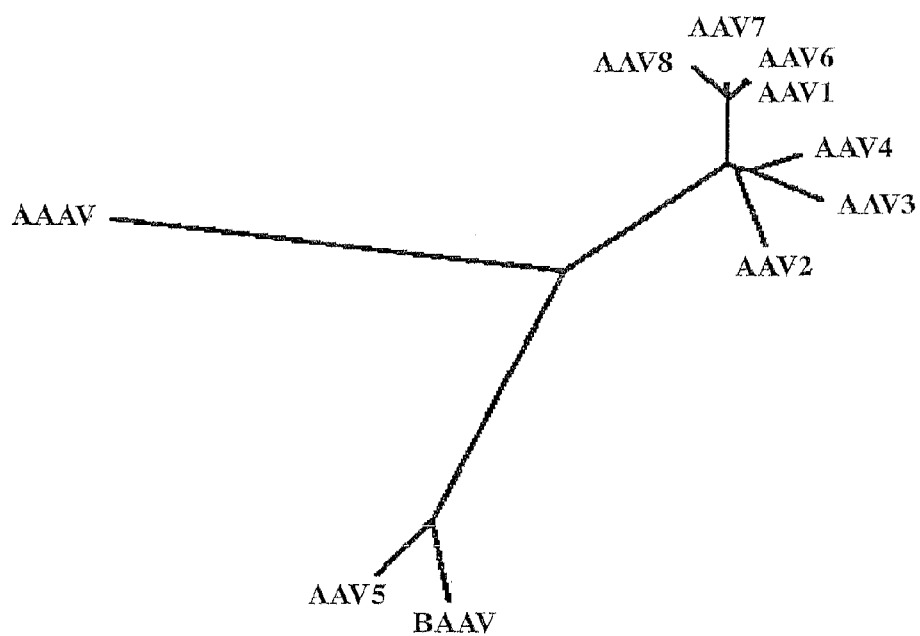
FIG. 3 illustrated comparisons of Rep and VP1 amino acid sequences. (A) Alignment of the amino acid sequences of BAAV Rep protein, AAV2 Rep protein (SEQ ID NO:30) and AAV5 Rep protein (SEQ ID NO:31) using MACVECTOR™. (B) Alignment of the amino acid sequences of BAAV VP1 protein (SEQ ID NO:7), AAV2 VP1 protein (SEQ ID NO:32) and AAV4 VP1 protein (SEQ ID NO:33) using MACVECTOR™. Identical amino acids are indicated by a dark, shaded box, similar amino acids by a light, shaded box. Dashes indicate gaps in the sequence added by the alignment program. Phylogenetic relationship of (C) BAAV Rep and (D) VP1 to other AAV serotypes is illustrated by an unrooted tree diagram.
Figure 3D:
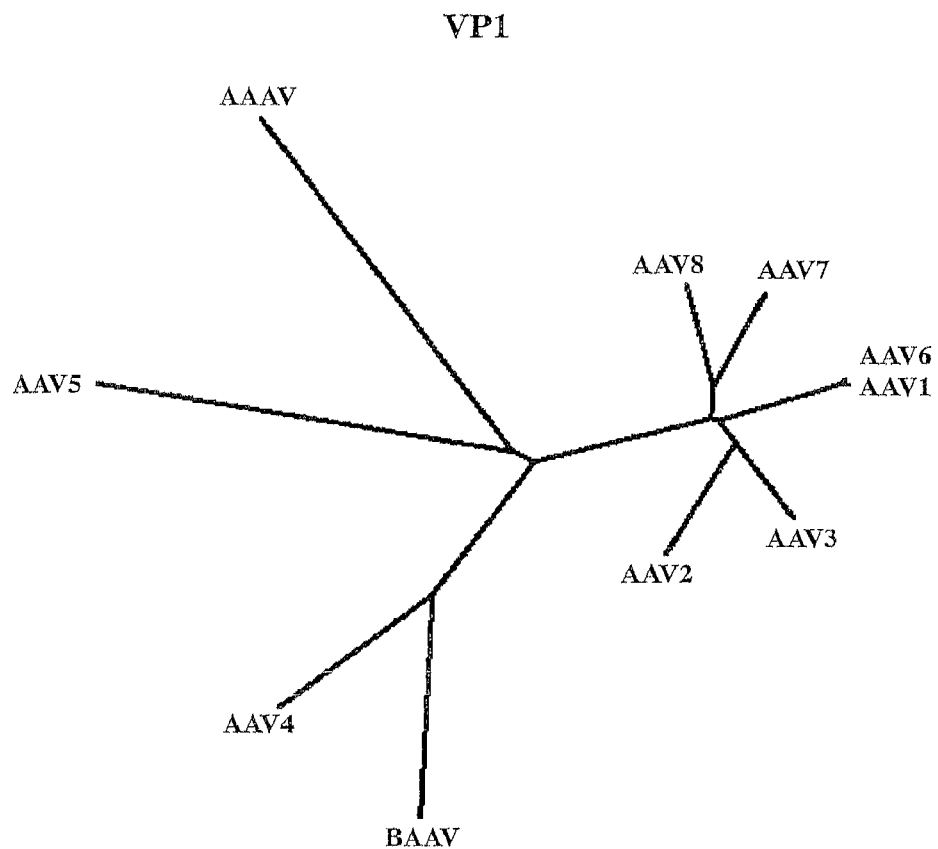

DNA and protein sequence alignments were performed using the Clustal W multiple sequence alignment tool of the Biology Workbench web based software (SDSC), MacVector 7 (Oxford Molecular). Promoters, transcription initiation and splice sites were predicted using the Neural Network Promoter Prediction web paged software (BDGP). The genome of BAAV is 4,694 nucleotides in length and has similar organization with that of other AAVs (FIG. 1A). The entire genome of BAAV displays 54-79% identity at the nucleotide level with the other known AAVs. Highest homology was observed with AAV5 (79%), lowest homology to BAAV showed AAAV with 54% (FIG. 1B). The BAAV genome has inverted terminal repeats of 150 nucleotides with are forming the characteristic T-shaped palindromic structure. The putative Rep-binding element (RBE) consists of a tandem $(GAGY)_4$ repeat, and the putative terminal resolution site (trs), AGTGTGG (FIG. 2). The BAAV ITR is greater than 95% identical to AAV5 and contains a trs that is identical to AAV5 as well as a conserved RRE. The Rep ORF of BAAV displays 48-89% identity at the amino acid level with the other AAVs, with most of the diversity clustered at the amino termini. A surprisingly high homology of 89% was found with AAV5 (FIGS. 3A and 3C). Comparison of the capsid proteins of BAAV and the primate dependoviruses revealed 55-76% identity with other known AAVs (FIGS. 3B and 3D). AAV4 showed the highest homology to BAAV with 76% while AAAV was most divergent with 55% identity to BAAV Vp1. Divergent regions in the capsid ORF are clustered in surface exposed loops.

Generation of Recombinant Virus

The high homology between the BAAV and AAV5 ITR and Rep amino acid sequence led to the assumption that BAAV can replicate and package AAV5 ITR containing vectors. This assumption was confirmed in initial experiments; AAV5 ITR containing vector plasmids containing a lacZ expression cassette were replicated and packaged with AAV5 or BAAV packaging plasmids with equal efficiency. Therefore, AAV5 ITR containing vector plasmids were used for all subsequent studies to produce recombinant BAAV.

Recombinant BAAV was generated by transfecting 293 T cells with AAV5 vector, BAAV packaging and Ad helper plasmids. 3 confluent T175 flasks of 293T cells were harvested, resuspended in 100 ml DMEM 10% FCS, seeded in 10 150 mm plates and incubated at 37° C., 5% $CO_2$ until cells are 80% confluent (typically 48 h). Cells were transfected with 15 µg pAAV5-NLS-GFP or pAAV5-RnlacZ, 15 µg pMMTV-BAAV and 30 µg p449B. 48 h after transfection, cells were harvested, washed with PBS and resuspended in 11 ml TD buffer (0.14 M NaCl, 5.0 mM KCl, 0.7 mM $K_2HPO_4$, 25.0 mM Tris, pH7.4. Cells were lysed by 3 freeze thaw cycles and incubated for 30 minutes at 37° C. after adding benzonase to a final concentration of 20 U/ml and sodium deoxycholate (final concentration of 0.5%). After adding 0.55 g CsCl/ml the lysate was fractionated using density gradient centrifugation in a SW41 rotor for 48 h at 38000 rpm. The gradients were harvested in 0.5 ml aliquots. Aliquots were assayed for infectivity and particle titer were determined by real time PCR using primers binding in the promoter region of the vectors.

Determination of Tissue Tropism

Figure 4:
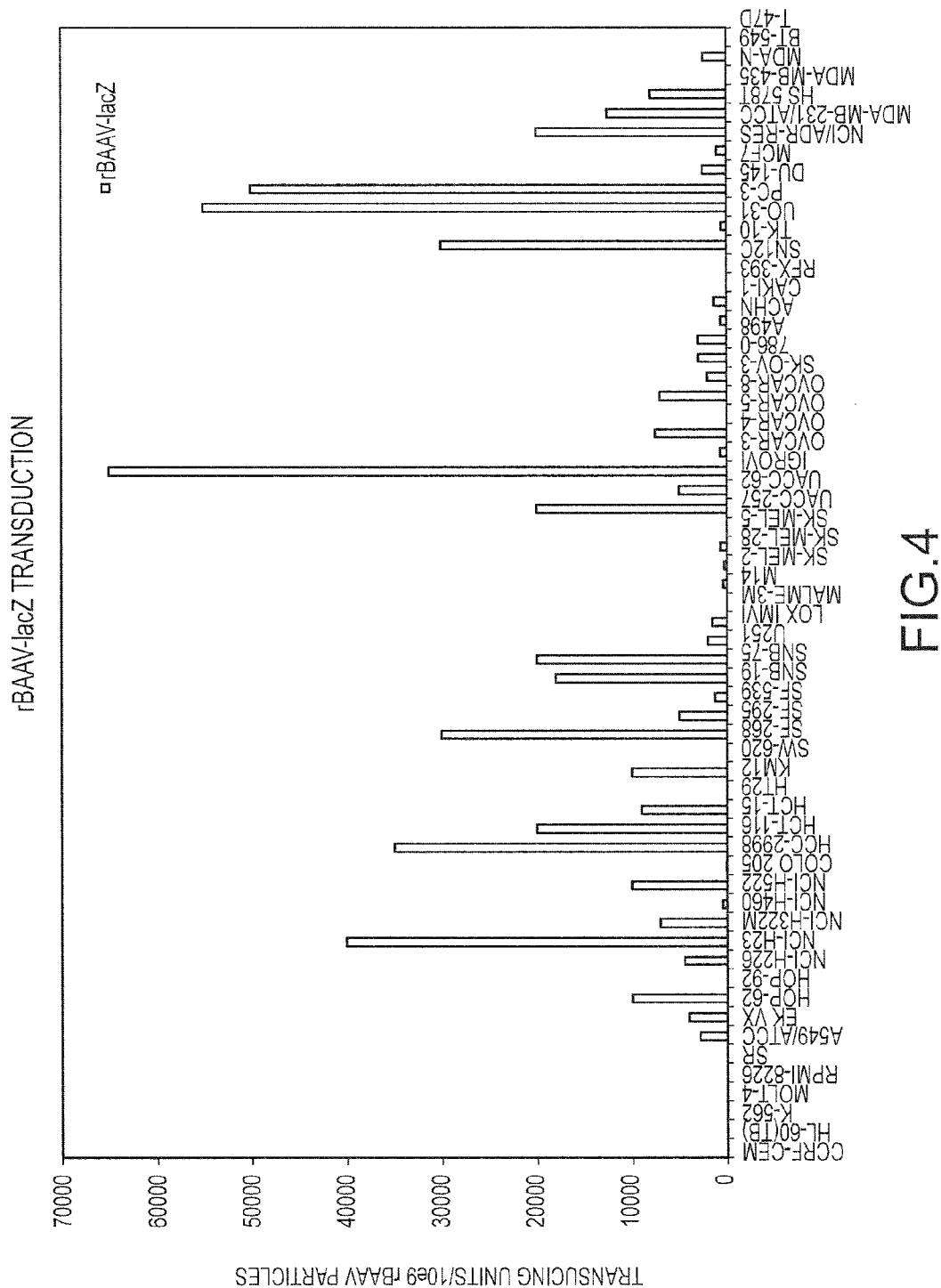
FIG. 4 shows the transduction profile of BAAV in 60 cancer cell lines. Human cell lines were infected with rBAAV expressing lacZ in serial dilutions and coinfected with a MOI of 10 with Ad5. Columns represent beta-Gal transducing units/$10^9$ DNAse resistant rAAV particles.

Transduction efficiency of recombinant BAAV vector containing an expression cassette for beta-galactosidase (rBAAV-RnlacZ) was analyzed in 60 cancer cell lines (NCI cancer cell panel). Cells were infected with an MOI of 10 with Ad5 and 2 h later with rBAAV-RnlacZ in 10 fold serial dilutions ranging from $10^2$ to $10^9$ particles/well. 48 h after infection, cells were fixed and stained for β-galactosidase activity with 5-bromo-4-chloro-3-indolyl-β-D-galactopyranoside (X-Gal) (Gold BioTechnology, Inc. St. Louis Mo.). Transduced cells were visually counted using a light microscope. GFP expressing cells were detected using fluorescent microscopy. Results were used to calculate the number of transduced cells for $10^9$ particles (FIG. 4). rBAAV efficient transduction of a wide variety of tumor cells including cells of CNS, colon, prostate, renal, breast and ovarian lineage. It is therefore a potent vector for gene transfer in a wide variety of gene therapy applications.

Due to the high homology between the BAAV and AAV5 ITR as well as Rep sequence, it was hypothesized that recombinant BAAV particles carrying a lacZ reporter gene or a GFP expression cassette could be produced by co-transfection of AAV5 ITR containing vector plasmids with BAAV packaging and an adenovirus helper plasmids in 293T cells. The recombinant particles have a buoyant density in CsCl gradients of 1.375 gm/cm$^3$ which is similar to AAV4. These recombinant particles have been used to compare the transduction efficiency of BAAV with other know AAV isolates and it was found that BAAV has a unique transduction profile compared to other isolates and is able to transduce a wide variety of tumor cells including cells of CNS, colon, prostate, renal, breast and ovarian lineage.

Figure 15:
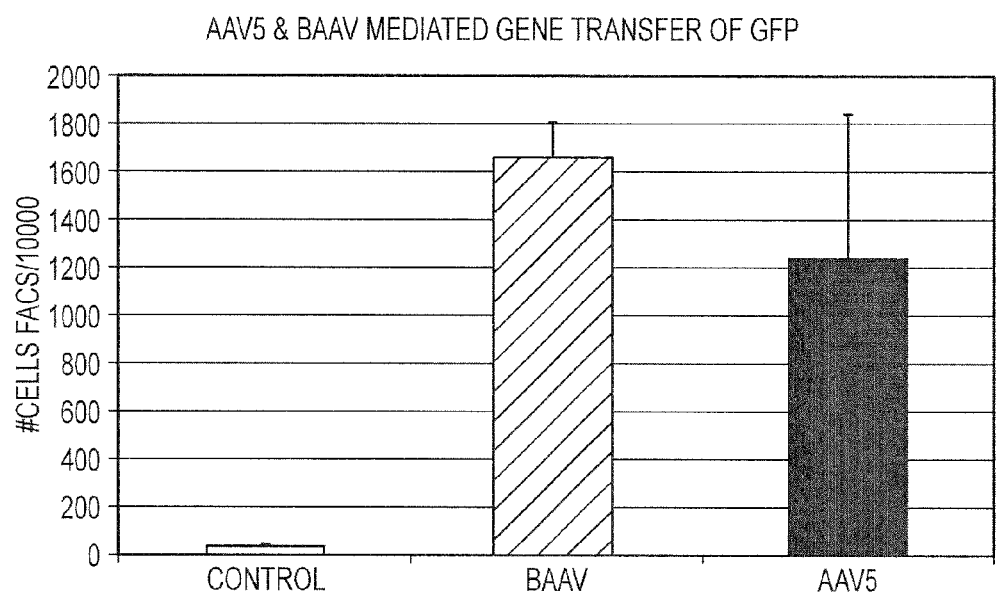
FIG. 15 shows that both AAV5 and BAAV efficiently transduce primary airway epithelia cells. These cells were cultured and plated as previously described with an equivalent number of rAAV5 or rBAAV particles containing CMV nuclear GFP—and cultured for over 10 days. GFP expression was determined by flow cytometry (FACS) and the relative transduction was compared.

To assess the tropism of BAAV in the lung, primary airway epithelia cells were cultured and plated as previously described (Zabner, J., et al. J. Virol. 2000 April; 74(8):3852-8, herein incorporated by reference for the teaching of these culturing methods) with an equivalent number of rAAV5 or rBAAV particles containing CMV nuclear GFP (MOI 10) and cultured for over 10 days. GFP expression was determined by flow cytometry (FACS) and the relative transduction was compared. Both AAV5 and BAAV efficiently transduced these cells (FIG. 15).

Neutralizing Antibody Assay

AAV isolates that are serological distinct can be distinguished by neutralization assays and are often referred to as AAV serotypes. BAAV was analyzed to determine if elicits a BAAV-specific immune response in mice that did not cross react with other AAV serotypes. BALB/c mice were injected with 10$^{10}$ particles of BAAV-RnlacZ, AAV2-RnlacZ, AAV4-RnlacZ and AAV5-RnlacZ. 4 weeks after infection serum of the infected animals was assayed in a neutralizing antibody assay.

Figure 5A:
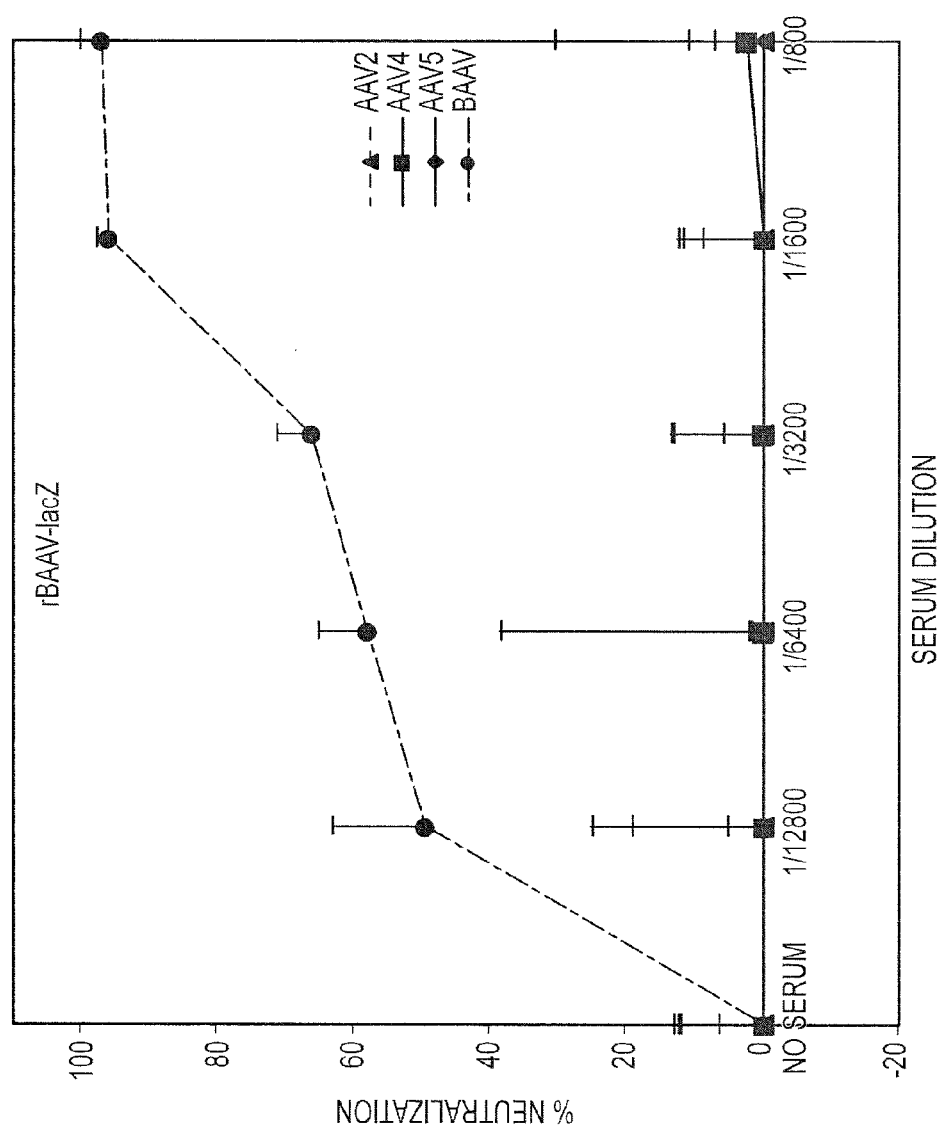
FIG. 5 shows that BAAV elicits a distinct immune response in mice. rBAAVlacZ (A) and rAAV1lacZ (B) were incubated with serial dilutions of polyclonal mice serum against rAAV2, rAAV4, rAAV5 and rBAAV. Cos cells coinfected with Ad5 (MOI=10) were incubated with the virus/serum mixture. % neutralization was calculated by the formula: 100×(1−transducing titers of serum incubated rAAV/untreated rAAV). Values of neutralization that were calculated to be below zero were adjusted to zero. Values given are means of 3 experiments, error bars represent standard deviation. BAAV transduction efficiency was unaffected by antisera against AAV2, AAV4 and AAV5. Antisera against BAAV blocked infection of BAAV but had no effect on the other AAV serotypes.
Figure 5B:
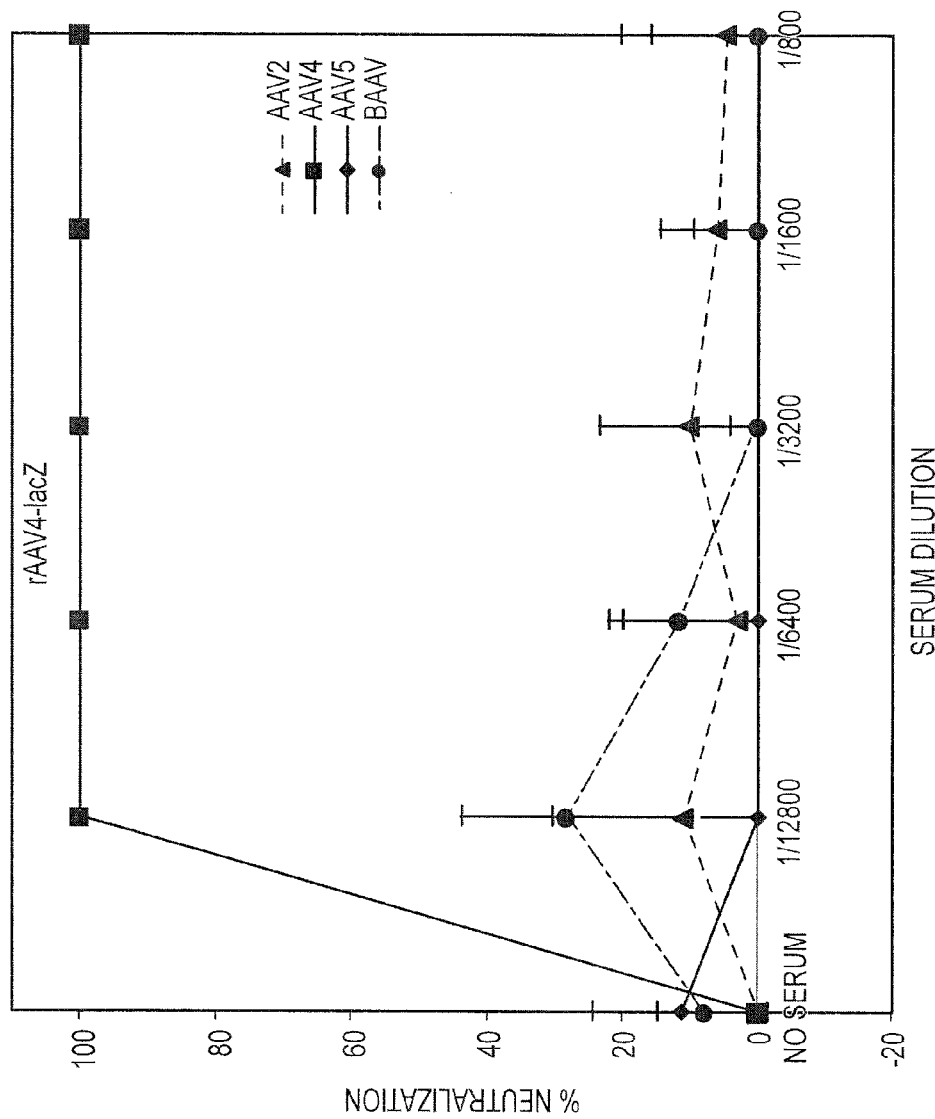

Exponentially growing COS cells (7×10$^3$) were plated in a density of 7×10$^3$/well in a flat-bottomed 96-well plate. 24 h after seeding, cells were infected with wild-type adenovirus with a MOI of 10 for 1 h. Heat inactivated sera of rAAV2, rAAV4, rAAV5 and rBAAV infected mice were serial diluted from 1:200 to a 1:12800 in RPMI containing 1% fatal calf serum (FCS). 40 transducing units of BAAV-RnlacZ (FIG. 5A) or AAV4-RnlacZ (FIG. 5B) (were added to the diluted sera and incubated for 1 h at 37° C. Subsequently, the virus/sera mixture was added to COS cells. 24 h after rAAV infection, cells were assayed for beta-galactosidase expression X-Gal staining (Gold BioTechnology, Inc. St. Louis Mo.). Transduced cells were visually counted using a light microscope. Neutralizing titers of the sera ware calculated as the highest dilution that inhibited 50% of transduction. Any serum dilution in which more than 70% reduction of positive cells compared with serum-free media remained was considered to be positive for neutralizing activity. All samples were assayed in duplicate or triplicate.

rBAAV elicited a unique immune response in mice that efficiently neutralized rBAAV, bud did not cross-react with rAAV4. Sera of rAAV2, rAAV4 and rAAV5 infected mice did not neutralize rBAAV. These results demonstrate that BAAV is a new AAV serotype.

Transduction of Submandibular Glands In Vivo

10$^{10}$ particles of AAV2-lacZ and BAAV-lacZ were injected into submandibular glands of BALB/c mice by retrograde ductal instillation as described earlier (Yamano et al., 2002). 4 weeks after infection, blood was collected form experimental animals by retro-orbital plexus bleed. Submandibular glands were excised, homogenized and lysed in 500 μL of Galact-light lysis solution (100 mM potassium phosphate (pH7.8), 0.2% TritonX-100) (Applied biosystems). PMSF and leupeptin were added to a final concentration of 0.2 mM and 5 μg/mL, respectively. The lysate was cleared by centrifugation at 10,000 rpm for 5 min. Genomic DNA was extracted from a 100-4 aliquot using the Wizard DNA extraction kit (Promega) according to the manufacturer's instructions. DNA concentrations were determined by spectrophotometry. Detection and quantification of genome copies of the AAV vectors was done by quantitative real time PCR using a TaqMan system (Applied Biosystems) with probes specific to the RSV promoter as described earlier ((Yamano et al., 2002)). Protein concentration of the lysates was determined using the BCA protein assay kit (Pierce) and β-Gal expression was quantified with a β-Gal ELISA kit (Roche Molecular Biochemicals). The β-Gal levels were normalized for total protein concentration and expressed as picograms of β-Gal per milligram of protein.

Recombinant BAAV was about ten fold more efficient than rAAV2 in the transduction of submandibular glands and expressing a gene of interest, demonstrating the feasibility of rBAAV to be used as a vector for gene therapy applications (FIG. 6A and FIG. 6B).

BAAV—Non Primate AAV Serotype

Recombinant BAAV has several attributes that make it an attractive vector for gene transfer including unique serological identity, cell tropism, and efficient gene transfer in vivo. BAAV is the third dependovirus of non-primate origin to be cloned and sequenced. The high homology between BAAV and AAV5 rep along with the biochemically distinct mechanisms of replication for these two viruses compared to other mammalian AAVs suggest that BAAV and AAV5 might form a distinct group within the dependovirus generation. The capsid of BAAV is most similar to that of AAV4, but the divergent regions are clustered mainly on the exposed surface loops that comprise the 3-fold axis of symmetry (amino acids 429-599 of SEQ ID NO:7). This region is critical for AAV2 transduction (Kern, Schmidt et al. 2003) (Opie, Warrington et al. 2003) (Schmidt, Katano et al. 2004). While differences in the capsid biochemical activity for the different serotypes of AAV are primarily responsible for their differences in transduction efficiency, some differences may be the result of the ITRs. While AAV2 and AAV4 can be packaged using AAV2 ITRs, AAV5 and BAAV rep proteins will not initiate replication of an AAV2 ITR. Therefore, these serotypes were both packaged using an AAV5 ITR. However, AAV5 and BAAV, which contain the exact same ITR, but have a significant difference in cell tropism and transduction efficiency in the inner ear, suggesting that the capsid interactions are primarily responsible for the differences in serotype tropism.

Example 2

BAAV Efficiently Transduces Neuroepithelial Cells in the Inner Ear

This example describes the tropism and transduction efficiency of a novel bovine adenoassociated virus (BAAV) vector in cultured inner ear epithelia and compares its infectivity with three, well characterized primate adenoassociated vectors: AAV2, -4, and -5. For the first time a cytoskeletal protein was used as a reporter gene for viral infection. Beta actin-GFP fusion protein is widely distributed in multiple cell types and when transiently expressed, it incorporates into hair cell stereocilia and into the apical junctional complex of hair cells and supporting cells. This example demonstrates that a novel bovine vector can efficiently transduce supporting and hair cells of cultured inner ear epithelia. Furthermore, prolonged incubation time with viral particles increases the yield of transduced cells. This novel bovine virus was significantly more effective in transducing cells of the inner ear epithelia than other tested AAV serotypes. Moreover, no pathological effects were demonstrated.

Reagents

Rhodamine/phalloidin and ProLong anti-fade mounting media were from Molecular Probes (Eugene, Oreg.). Cell Tak was from BD Biosciences (Palo Alto, Calif.). DMEM F-12, L-15 media, fetal bovine serum and ampicillin were from GIBCO (Carlsbad, Calif.).

Viral Vector Construction

The construction of the beta galactosidase and GFP expression plasmids is described above. The AAV2 beta actin-GFP fusion expression plasmid was constructed by subcloning of the CMV-beta-actin-GFP cassette from beta actin-GFP plasmid (Clontech) into the AAV2 RSV-GFP expression plasmid and replacement of the RSV GFP cassette with the CMV beta actin-GFP. The AAV5 beta actin-GFP fusion expression plasmid was produced in the same manner; however, the CMV beta-actin-GFP cassette was cloned into the AAV5 RSV-GFP plasmid.

AAV Preparation and Quantification

Recombinant AAV particles were produced by triple transfection of 293 T cells with AAV helper plasmids expressing the AAV Rep and Cap genes, a vector plasmid containing the reporter gene flanked by either type 2 ITRs (AAV2, AAV4) or AAV5 ITRs (AAV5, BAAV), and the Ad helper plasmid pAd12 (Smith, Afione et al. 2002). Recombinant vectors were purified by fractionation with CsCl-gradient centrifugation. DNAase resistant genome copy titers of the vector preparations were determined by quantitative real time PCR using the TaqMan system (Applied Biosystems) with probes specific to the RSV promoter. Viruses in CsCl were dialyzed for 24 h using 0.5 ml slide-A-Lyzer (Pierce) in 100 ml of serum free medium with changing of the medium 3-4 times.

Organotypic Cultures of Rat and Mouse Organ of Corti

Organotypic cultures of rat and mouse organ of Corti and vestibular sensory epithelia were prepared according to a published method (Sobkowicz, Loftus et al. 1993, which is hereby incorporated by reference for its teaching of the method of making organotypic cultures of rat and mouse organ of Corti and vestibular sensory epithelia). Explants from the developing inner ear harvested from neonates can be maintained for two weeks in culture during which they reach structural and functional maturity (He, Zheng et al. 2001). PD 0-1 rat pups were anaesthetized using $CO_2$ according to NIH guidelines. The skin was cleaned thoroughly with 70% ethanol. After decapitation, both temporal bones were isolated and placed into L-15 media under sterile conditions. Each otic capsule was opened and the stria vascularis, spiral ganglion, Reisner's membrane, and tectorial membrane were removed from all turns of the cochlea. In addition, the otoconial membrane was removed from the maculae utriculae and saculae. The isolated organ of Corti was divided for culturing. Subsequently, the vestibular system was finely dissected. Each sample of the organ of Corti and vestibular system was attached to a Cell Tak-coated coverslip in a culture dish. Cultures were maintained at 37 C and 5% $CO_2$ in DMEM F-12 supplemented with 7% fetal bovine serum containing 1.5 µg/ml ampicillin.

Viral Infection and Histochemistry

Cultured explants of auditory and vestibular sensory epithelia were infected with AAV2, AAV4, AAV5, and BAAV viral vectors using beta actin-GFP as a reporter gene (BD Bioscience) in 200 µl of DMEM F-12 at 37° C. and 5% $CO_2$ for the duration of the experiment. For immunohistochemistry, cultures were fixed with 4% paraformaldehyde in PBS for 1 h at room temp, permeabilized for 30 min with 0.5% Triton X-100 in PBS, and the actin filaments were counterstained with rhodamine/phalloidin (0.2 U/200 ul Molecular Probes) for 30 min. Stained explants were removed from the culture dish and mounted using ProLong anti-fade media. Fluorescence images were obtained either with a Zeiss LSM 510 confocal microscope using a 100×1.4 numerical aperture objective. Image acquisition and post acquisition analysis were performed using NIH image and Adobe Photoshop.

Statistical Analyses

Sample frames of sensory epithelia were photographed with a 40× objective. For each measurement, 5 independent frames from at least three explanted culture pieces were scored for GFP positive cells and the total number of cells was determined by scoring the rhodamine phalloidin positive cells. Single factor ANOVA and Student's t test analyses were performed using Microsoft Excel.

Characterization of Baav Transduction of Hair Cells

In order to evaluate the tropism of this non-primate bovine vector, BAAV, we incubated cultured explants of rat auditory and vestibular epithelia with BAAV expressing different reporter genes (beta galactosidase, GFP, and beta Actin-GFP). In the preliminary experiments we used a common reporter gene, GFP. The long, columnar shape of hair cells and complex cellular architecture of sensory epithelia, however, made it very difficult to estimate the type and number of transduced cells based only on the diffuse cytoplasmic labeling. To overcome this difficulty, we used beta actin-GFP fusion protein as a reporter. Beta actin-GFP can selectively incorporate into hair cells stereocilia (Schneider, Belyantseva et al. 2002) (Rzadzinska, Schneider et al. 2004) as well as into the apical junctional complex of hair cells and supporting cells. This process allows a straightforward identification of infected cells on the surface of sensory epithelia.

Hair cell maturation occurs during the first few days after birth. Previous studies have shown that for adenovirus vectors, cell tropism changed with the maturation of the auditory sensory epithelia (Kanzaki, Ogawa et al. 2002). The tropism and transduction efficiency of BAAV in developing (PD 2) and mature (PD 10) inner ear explants was evaluated. Analysis of fixed and counterstained developing cultures after 8 days of incubation with $10^{10}$ resistant particles/ml (DNAse resistant particles (DRP)/ml) of BAAV revealed transduction of both hair cells and supporting cells. Inner and outer hair cells of the organ of Corti as well as vestibular hair cells showed incorporation of beta actin-GFP into stereocilia starting from their tips. This finding is identical to results obtained with GeneGun™ plasmid delivery (Schneider, Belyantseva et al. 2002). We also observed incorporation of beta actin-GFP into apical junctional complexes of transduced hair cells and supporting cells such as Hensen's, phalangal, interdental, and vestibular supporting cells. In all of the analyzed explants (n=50) we did not observe any significant changes in the overall pattern of the reticular lamina even after a prolonged incubation of 8 days with BAAV. High magnification images of hundreds of different transduced cells also did not reveal any signs of structural damage. Because of the cellular complexity of inner ear epithelia and the lack of appropriate cellular markers, we were unable to determine accurately the total number of various supporting cell types in an explant. We estimated that 100% of the supporting Hensen's cells and vestibular supporting cells were transduced whereas approximately 40% of the phalangal and interdental cells were transduced. Hair cells were readily quantified by scoring stereocilia bundles and comparing them to the number of phalloidin stained bundles. In PD 2 cultures, BAAV successfully transfected 10% of inner (n=773) and outer (n=189) hair cells and 48% of vestibular hair cells (n=2032). Previous studies suggested that hair cell competency decreased with the maturation stage of the hair cell (Kanzaki, Ogawa et al. 2002).

Therefore, we tested whether the stage of hair cell maturation influenced BAAV tropism or transduction efficiency.

Figure 7:
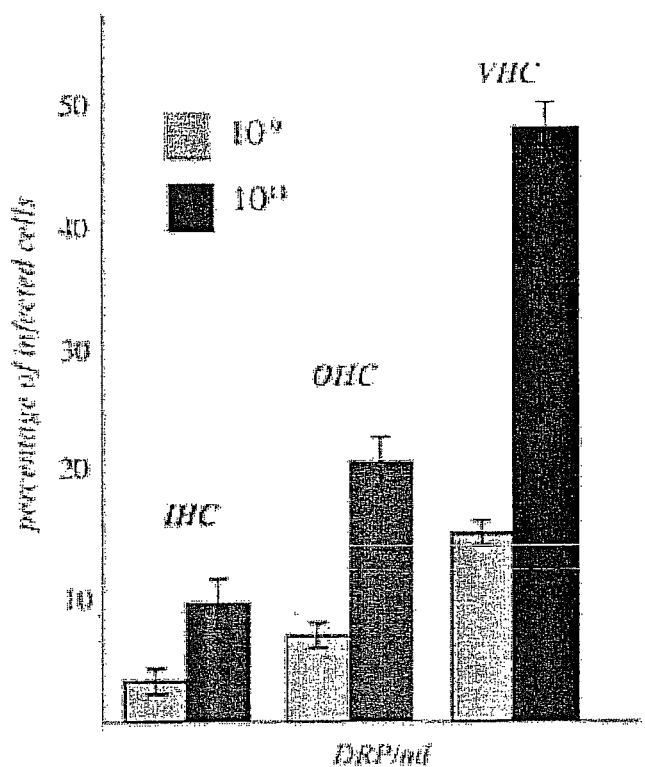
FIG. 7 is a comparison of transfection yield at increasing viral titers; At least 5 samples harvested from at least three explants were scored for transfected and not transfected hair cells at viral titers ranging from $10^9$ to $10^{11}$ DRP/ml. The transfection yield increased significantly for OHC(N=5 and 13 Respectively, Single Factor ANOVA p=0.01699) and VHC (N=6 and 10 respectively, Single Factor ANOVA p=0.000168) with a 100 fold increase in viral titer after 8 days. The differences in transfection yield of IHC were not significant (N=5 and 1, Single Factor ANOVA p=0.23987).
Figures 8A, 8B:
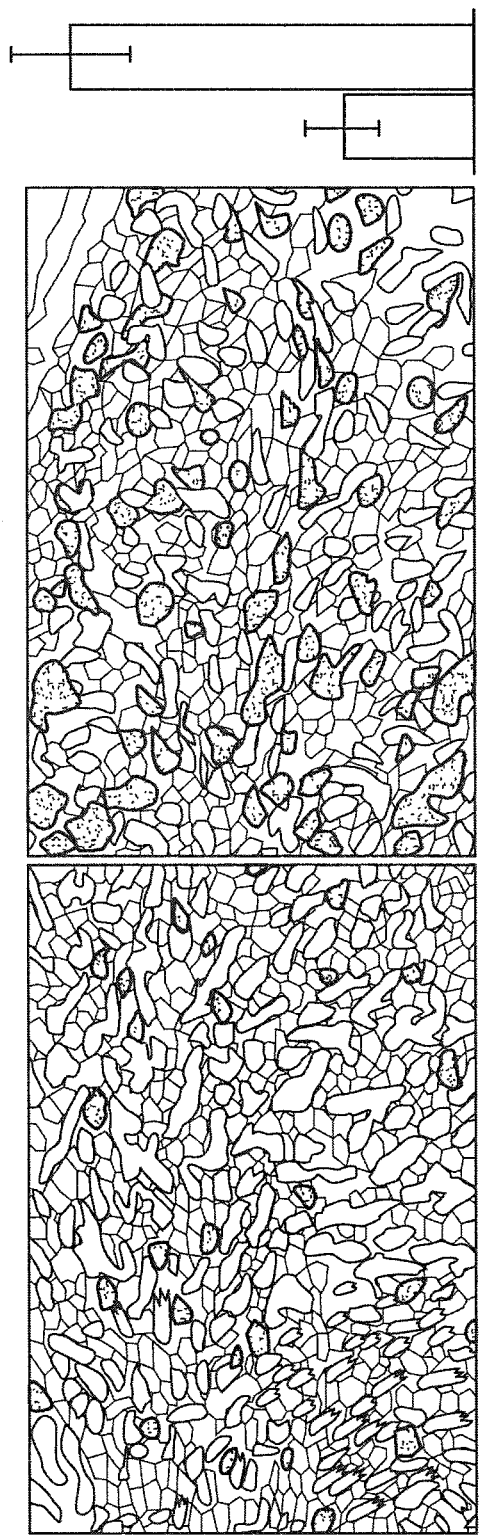
FIG. 8 shows the apparent transfection efficiency increased significantly with longer incubations with viral particles; A) Confocal image of vestibular epithelia after 5 days of BAAV infection. The positively transduced hair cells are easily scored even though the yield is sparse. B) Confocal image of vestibular epithelia after 8 days of BAAV infection demonstrating almost half the hair cells are transfected. C) Histogram of transfection yields. There is a statistically significant increase (N=7 and 10 frames respectively from at least 3 explants p>0.01) in the transfected cells after an additional three days of incubation. Size bar=20 um.

Qualitative analysis of PD 10 cultures incubated with BAAV revealed successful transfection of hair cells and the same transduction pattern observed in PD 2 cultures. The overall yield of transduced vestibular hair cells in the older cultures was significantly lower ($p<0.05$) than in PD 2 explants (17% in PD 10, n=1549 and 48%, n=2032 in PD 2 explants). Unfortunately, auditory hair cells progressively degenerate in cultures older than 15 days. Thus, we were unable to estimate number of infected inner or outer hair cells for these older cultures. Furthermore, the transduction in PD2 cultures was concentration dependent; increasing concentrations of BAAV vector resulted in a significant increase in transduction of hair cells (FIG. 7). The greatest improvement in transfection yield was observed in vestibular hair cells where almost 50% of the hair cells were transformed after 8 days. To analyze if the duration of incubation with viral particles influenced the number of BAAV transduced cells and increased the apparent transfection efficiency, we incubated PD 2 explants with viral particles for 5 or 8 days (FIG. 8A-B). We observed a significantly higher yield ($p<0.05$) of transduced vestibular and outer hair cells following a longer incubation time (FIG. 8C). The number of transduced vestibular hair cells increased from 15% on day 5 to 48% after 8 days. Transduction of outer hair cells also increased 4-fold after 8 days but no significant increase of inner hair cells transduction was observed.

This demonstrates for the first time that the present bovine adenoassociated virus vector can efficiently transduce developing and mature hair cells of the organ of Corti and vestibular epithelia as well as supporting cells of the inner ear explants. The observation that functionally mature hair cells of PD 10 explants can be transformed with BAAV is encouraging and further supports gene transfer using BAAV to transfect hair cells of adult animals.

The observation that the yield of transduced cells increased over time is consistent with similar observations in vivo AAV5, AAV4 (Davidson, Stein et al. 2000). Interestingly, closer examination of the hair bundles revealed that many of the transduced hair cells incorporated actin-GFP only at the stereocilia tips. Previous studies showed that beta actin-GFP was progressively incorporated into stereocilia starting from stereocilia tips as early as 4-6 h after transfection using a gene gun. Within 48 to 72 h the entire stereocilia bundle is labeled in auditory and vestibular hair cells respectively. The presence of hair cells showing incorporation of beta actin-GFP at the stereocilia tips after 8 days of incubation with virus may indicate that the onset of viral transduction can occur through out the course of experimental exposure.

The substantial differences in transfection efficiency between supporting cells and hair cells prompted us to evaluate the ability of BAAV to transduce other polarized epithelia. We extended the panel of epithelial cell lines previously characterized by testing MDCK (dog kidney epithelial cell line) and caco-2 (human adenocarcinoma epithelial cell line) cells because of their overall similarity to inner ear sensory epithelia (Schmidt, Katano et al. 2004). Confluent cultures of MDCK and caco-2 were incubated with BAAV expressing beta actin-GFP at the concentration $10^{10}$ DRP/ml of viral particles for 8 days. Surprisingly, we did not observe any transduction in MDCK cell cultures even after 8 days of infection; however, about 20% of caco-2 cells showed beta actin-GFP expression.

Comparison of Transduction with Different Serotypes of AAV

Figure 9:
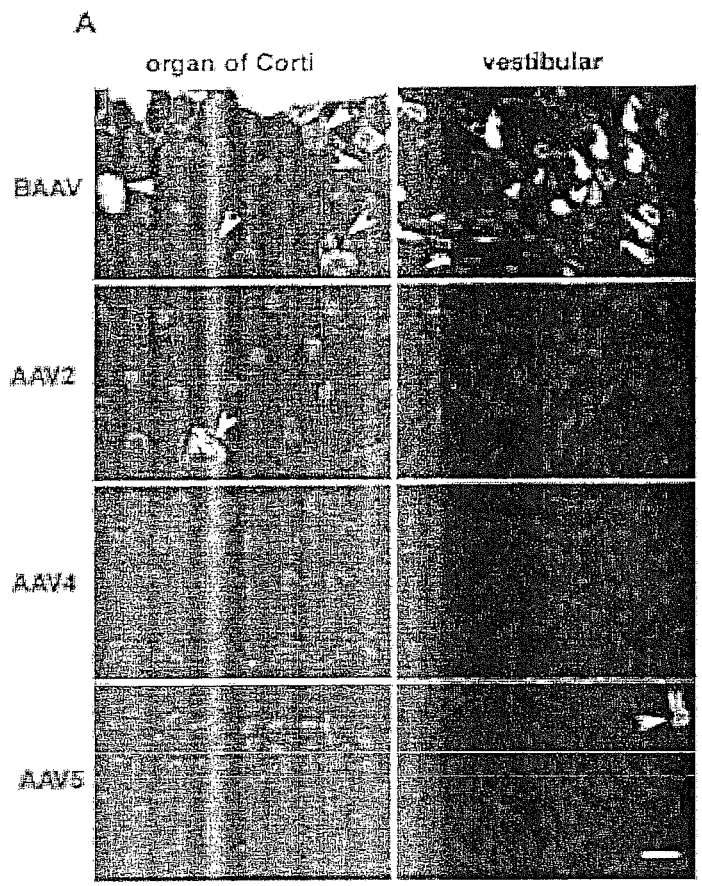
FIG. 9 is a comparison of the transfection efficiency of bovine AAV with three primate AAVs. Cochlear and vestibular explants were incubated with virus for 8 days and transfection yields were measured per sample frame. (A) BAAV transfected auditory and vestibular hair cells. (arrows) In contrast AAV2, 4 and 5 were surprisingly ineffective. (arrows) (B) 10 frames of each epithelia were measured and the transfection efficiency scored. In general the primate derived adenoassociated viruses were ineffective as vectors for hair cell. Size bar=20 um.

Previous studies concluded that AAV2 could transduce cells in the inner ear (Luebke, Steiger et al. 2001). Therefore, tropism and transduction efficiency of BAAV was compared in inner ear epithelia with other well characterized serotypes of adenoassociated viruses; AAV2, -4 and -5. Cultured explants of rat auditory and vestibular epithelia (PD2) were incubated with either AAV2, -4, -5 or BAAV expressing beta actin-GFP at a concentration of $10^{10}$ DRP/ml for 8 days. Confocal analysis of fixed and counterstained samples revealed that overall BAAV was the most effective vector for hair cell transduction and supporting cells in cultured inner ear sensory epithelia. With BAAV we counted at most 48% of the vestibular, 16% of auditory hair cells, 100% of Hensen's, and 40% of phalangal cells were transfected. On the other hand, cultures incubated with AAV2 showed transduction in 4% of inner hair cells and AAV5 transduced 1% of the vestibular hair cells. Transduction of supporting cells with either AAV2 or AAV5 or transduction with AAV4 was not observed (FIG. 9). This is in contrast to several studies using AAV2 serotypes in adult animals have demonstrated transduction-supporting cells in the inner ear (Li Duan, Bordet et al. 2002). Indeed, we found that AAV2 serotypes were much less effective at transducing hair cells then BAAV.

Beta Actin-GFP—an Optimal Reporter Gene for Inner Ear Epithelia

Beta actin-GFP used in these studies as a reporter gene for analysis of tropism and infectivity of viral vectors allowed for the identification of transduced and non-transduced cells in surface preps of sensory epithelia based on labeling of the hair bundle. In addition, localization of beta actin-GFP into the apical junctional complexes of hair cells and supporting cells indicated borders between cells in these complex mosaics of different cells and simplified counting of the transduced cells. Additionally, the ability to follow turnover of stereocilia actin in cells expressing beta actin-GFP allows for the determination of initiation of expression.

Molecular Basis of Specificity of AAV Serotypes

In contrast to BAAV, rAAV2 and rAAV5 were less effective at transducing hair cells. Our in vitro results with rAAV2 are consistent with the in vivo studies using AAV2 since less then 2% of the hair cells were transfected (Luebke, Foster et al. 2001). Efficient AAV2 transduction requires expression of heparan sulfate proteoglycan on the target cell surface. Heparan sulfate cytochemistry indicated that hair cells do not express this glycoprotein residue on their apical cell surface (Luebke, Steiger et al. 2001). Characterization of the cellular components required for transduction with AAV4 and AAV5 demonstrate that both serotypes preferentially bind to 2-3 sialic acid residues but differ in their linkage specificity. In addition, PDGFRα or PDGFRβ have been identified as protein receptors for AAV5 and their expression correlates with transduction in vivo (Di Pasquale, Davidson et al. 2003), while sialic acid residues that have been localized to the stereocilia cell surface are very sparsely distributed on the apical surface of hair cells (Suzuki, Katori et al. 1995). Furthermore, only PDGFR alpha receptors have been localized to the lateral wall of vestibular hair cells and not the apical surface (Saffer, Gu et al. 1996). Taken together, these data are consistent with the low transduction efficiency observed with primate isolates of AAV2, AAV4, and AAV5.

Summary

BAAV has a 10-fold higher transduction efficiency for neuroepithelial cells of the inner ear as compared to primate derived AAV serotypes. Efficient gene transfer to the cochlea offers both a tool needed for new therapies for deafness and the ability to study specific genes and their function. The nearly 100% gene transfer in supporting cells is expected to be useful clinically because many genetic hearing loss diseases are caused by mutations which effect the supporting cell integrity. Most importantly, the availability of a vector, which efficiently transduces hair cells in vivo, advances our ability to characterize the structure and function of the inner ear. The combination of efficiency and lack of adverse effects makes BAAV an exciting new vector choice for gene transfer to the sensory and nonsensory cells of the inner ear.

Example 3

Role of Sialic Acid and Glycosphingolipids in Baav Transduction

Figure 10:
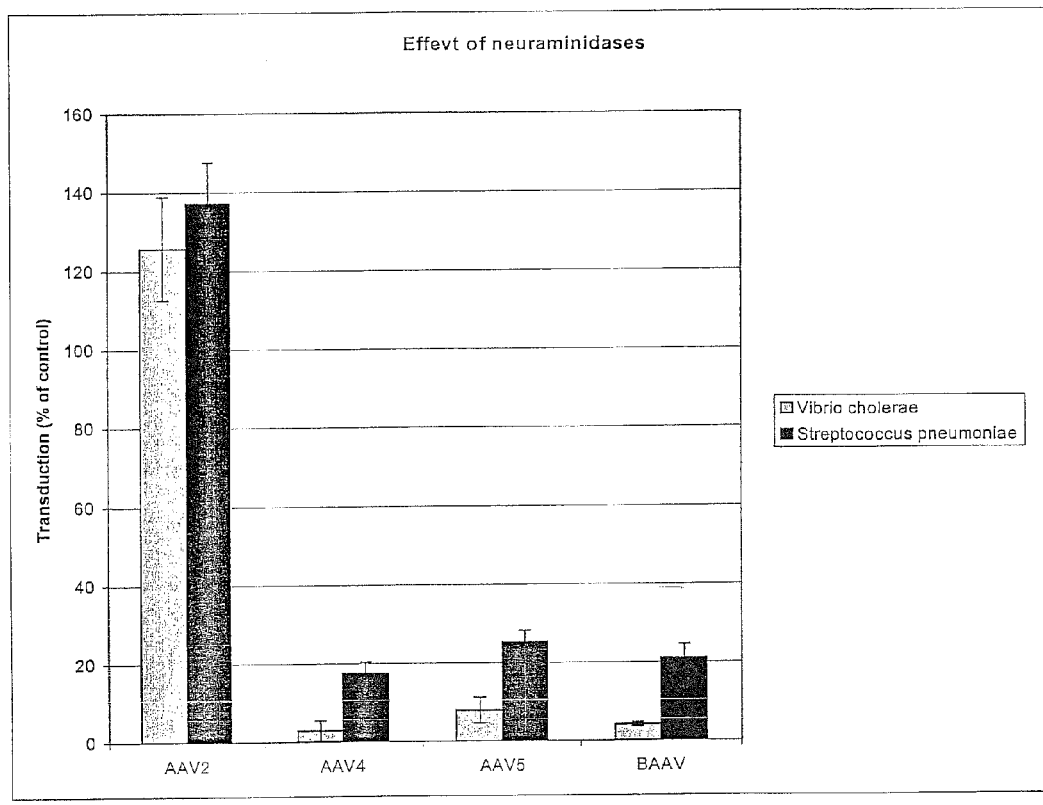
FIG. 10 shows that BAAV transduction requires 2-3 sialic acid. Cos cells were incubated with the broad spectrum neuraminidases isolated from V. cholerae, (0.05 U/ml) and a neuraminidase with high specificity for 2-3 sialyl linkages from S. pneumoniae (10 U/ml). 48 h after infection with recombinant AAV2, AAV4, AAV5, or BAAV expressing GFP, cells were analyzed for GFP expression. Neuraminidase treatment resulted in reduction of BAAV transduction, demonstrating the requirement for 2-3 linked sialic acid, bound to either a protein or lipid receptor for BAAV transduction.

The role of sialic acid in BAAV transduction was determined by treating Cos with the broad spectrum neuraminidases isolated from *V. cholerae*, (0.05 U/ml) and a neuraminidase with high specificity for 2-3 sialyl linkages from *S. pneumoniae* (10 U/ml). 48 h after infection with recombinant AAV2, AAV4, AAV5, or BAAV expressing GFP, cells were analyzed for GFP expression. Neuraminidase treatment resulted in reduction of BAAV transduction (FIG. 10), demonstrating the requirement for 2-3 linked sialic acid, bound to either a protein or lipid receptor for BAAV transduction.

Figure 11:
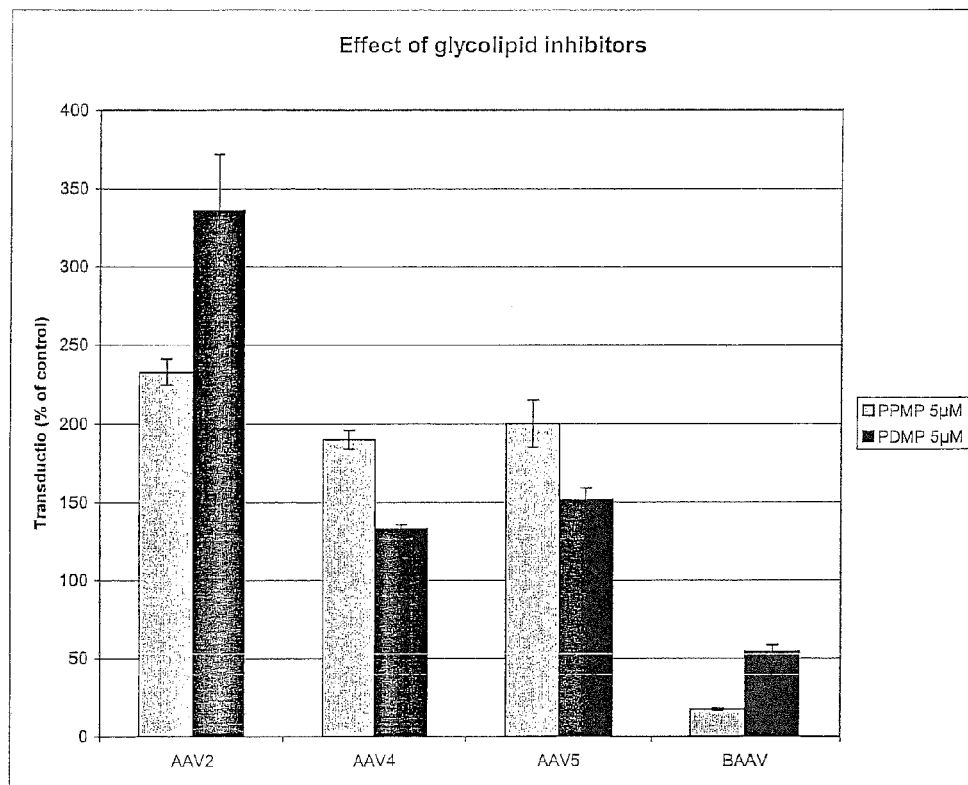
FIG. 11 shows that BAAV transduction can be inhibited with inhibitors of glycolipid synthesis. Untreated COS cells or cells incubated for 48 h with 5 μM PPMP or 5 μM PDMP were infected with recombinant AAV2, AAV4, AAV5 or BAAV expressing GFP. 48 h after infection, cells were analyzed for GFP expression. Inhibition of glycolipid synthesis resulted in clear reduction of rBAAV mediated gene transfer compared to untreated control, while rAAV2, rAAV4 and rAAV5 transduction was enhanced. This indicated the usage of phospholipids in rBAAV receptor binding or uptake.

The role of glycosphingolipids (GSL) was examined in BAAV mediated gene transfer, by treating Cos cells for 48 h with inhibitors of glycosphingolipid metabolism, PPMP (5 µM) and PDMP (5 µM), and analyzed the effect of GSL depletion on BAAV, AAV4 and AAV5 transduction. We observed a 90% and 50% inhibition of BAAV mediated gene transfer respectively, whereas AAV4 and AAV5 transduction remained uninhibited (FIG. 11). This implies that the transduction process of BAAV is significantly different from AAV4 and AAV5, and involves GSLs that act either as receptors or as essential parts of the uptake machinery.

Figure 12:
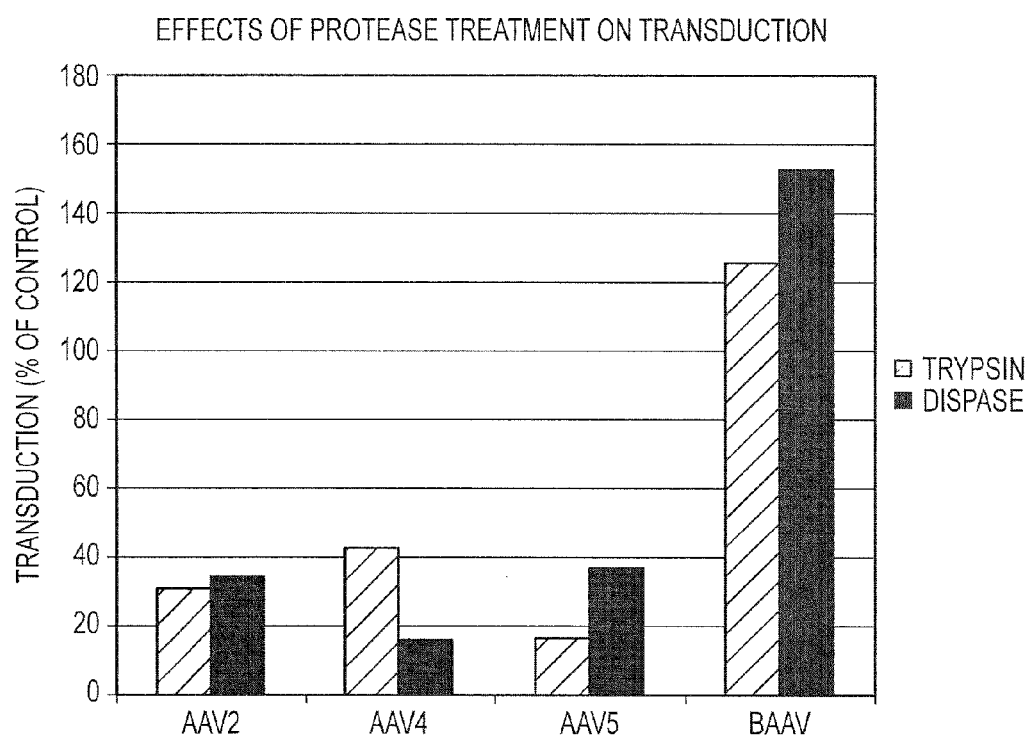
FIG. 12 shows that the receptor for BAAV is protease resistant. Cos cells were incubated with 0.025% trypsin or 1 U/ml dispase for 30 min. 48 h after infection with recombinant AAV2, AAV4, AAV5 or BAAV expressing GFP, cells were analyzed for GFP expression. Protease treatment resulted in reduction of rAAV2, rAAV4 and rAAV5 transduction, while BAAV mediated gene transfer was slightly enhanced, suggesting that either a protease resistant protein or a lipid component is essential for rBAAV binding and uptake.

It was further determined that the receptor for BAAV is protease resistant. Cos cells were incubated with 0.025% trypsin or 1 U/ml dispase for 30 min. 48 h after infection with recombinant AAV2, AAV4, AAV5 or BAAV expressing GFP, cells were analyzed for GFP expression. Protease treatment resulted in reduction of rAAV2, rAAV4 and rAAV5 transduction, while BAAV mediated gene transfer was slightly enhanced (FIG. 12), suggesting that either a protease resistant protein or a lipid component is essential for rBAAV binding and uptake.

Example 4

Transcytosis of BAAV Vectors

Previous research had demonstrated that Caco-2 and MDCK cells are model cell lines for the study of macromolecular transport via transcytosis. Furthermore these cell lines have been used to demonstrate transcytosis of both viruses and proteins. Therefore, to test if AAV can spread through tissue by transcytosis, $2 \times 10^8$ DNA resistant particles of recombinant AAV2 (rAAV2) AAV4, AAV5, AAV6, BAAV suspended in 50 ul of medium were placed in the upper (apical) side of the transwell polycarbonate filter over a monolayer of cells each of the following cells Caco-2, MDCKI, MDCKII, Human primary airways epithelia cells (Airway), Human primary immortalized epithelial endometrial, Bovine brain primary endothelia cells (BBB), or HeLa. All cultures had TERs indicating the formation of tight junctions and polarized phenotype. After 3 hours of incubation the medium in the basal side of the transwell was collected and tested for the presence of transcytosed rAAV DNA. Viral DNA was extracted from 200 ul of basal medium and quantified by qPCR.

Figure 13:
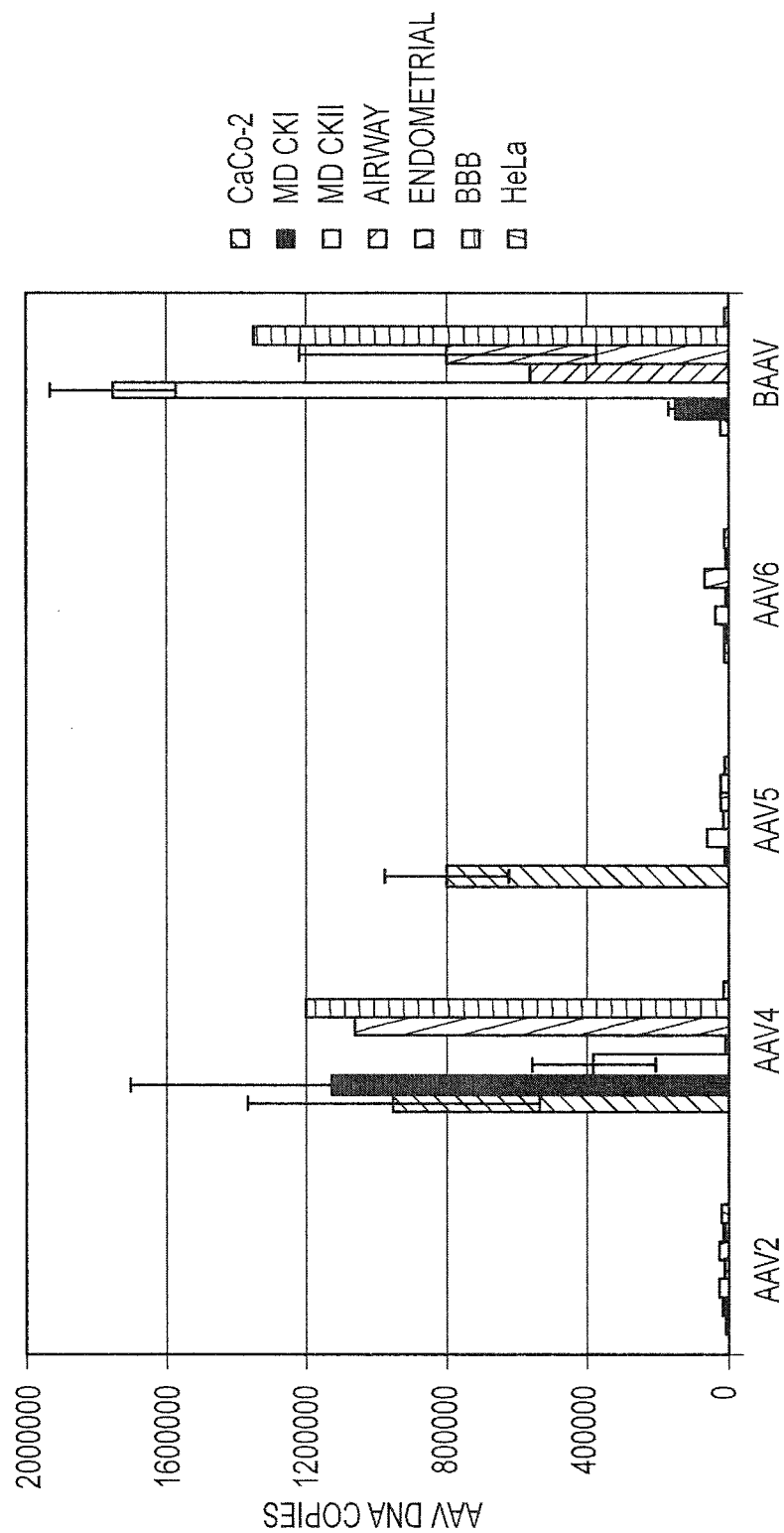
FIG. 13 shows that AAV4 transcytosed in CaCo-2, MDCKI, MDCKII, Human primary immortalized epithelial endometrial, Bovine brain primary endothelia cells (BBB). AAV5 transcytosed CaCo-2 cells, whereas BAAV transcytosed in MDCKs, Endometrial, airways epithelia, and BBB. AAV6 did not transcytose in any of cell types tested. HeLa cells do not form barrier epithelia and were used as a control.

In these cell lines, transcytosis was observed with several AAV serotypes and appeared to be both serotype and tissue-specific (FIG. 13). Three hours after the addition of AAV to the apical surface of the cells, over 800,000 particles of AAV5 were present in the media on the basal lateral side of the trans-well insert of CaCo-2 cells, but not the MDCK, airway epithelia, endometrial, or BBB cells (FIG. 13). Similarly BAAV particles were detected in the media on the basal lateral side of the MDCK, airways epithelia, endometrial, and BBB cells but not the Caco-2 cells. Interestingly, AAV4 was detected in the basal lateral media of all cell types. No virus was detected in the basal lateral media when AAV2 was added to the apical surface in either cell type. AAV6 did not transcytose in any of cell types tested, and was not tested on airway epithelia or BBB. HeLa cells do not form barrier epithelia and were used as a control.

Previous work has demonstrated that transcytosis is a temperature dependent process than can be inhibited at 4° C. Transcytosis can also be inhibited by the addition of agents that selectively fix the plasma membrane. Recently the addition of tannic acid, a mild fixative agent, to the basal lateral surface blocked the transcytosis of GPI-anchored proteins to the apical surface (Polishchuk R, *Nat Cell Biol*. 2004. 6(4): 297-307). Therefore the ability of this agent to block the transcytosis of AAV was tested. Treatment of the basal lateral surface of either Caco-2 or MDCK cells prior to virus addition to the apical surface blocked the accumulation of AAV5 or BAAV in the basal lateral media. Furthermore, quantification of the intracellular virus demonstrated inhibition of exocytosis by tannic acid treatment dramatically increase the amount of AAV DNA in the cell suggesting the viral particles detected in the basal lateral media are the result of an intracellular transport process and not a paracellular route.

Figure 14:
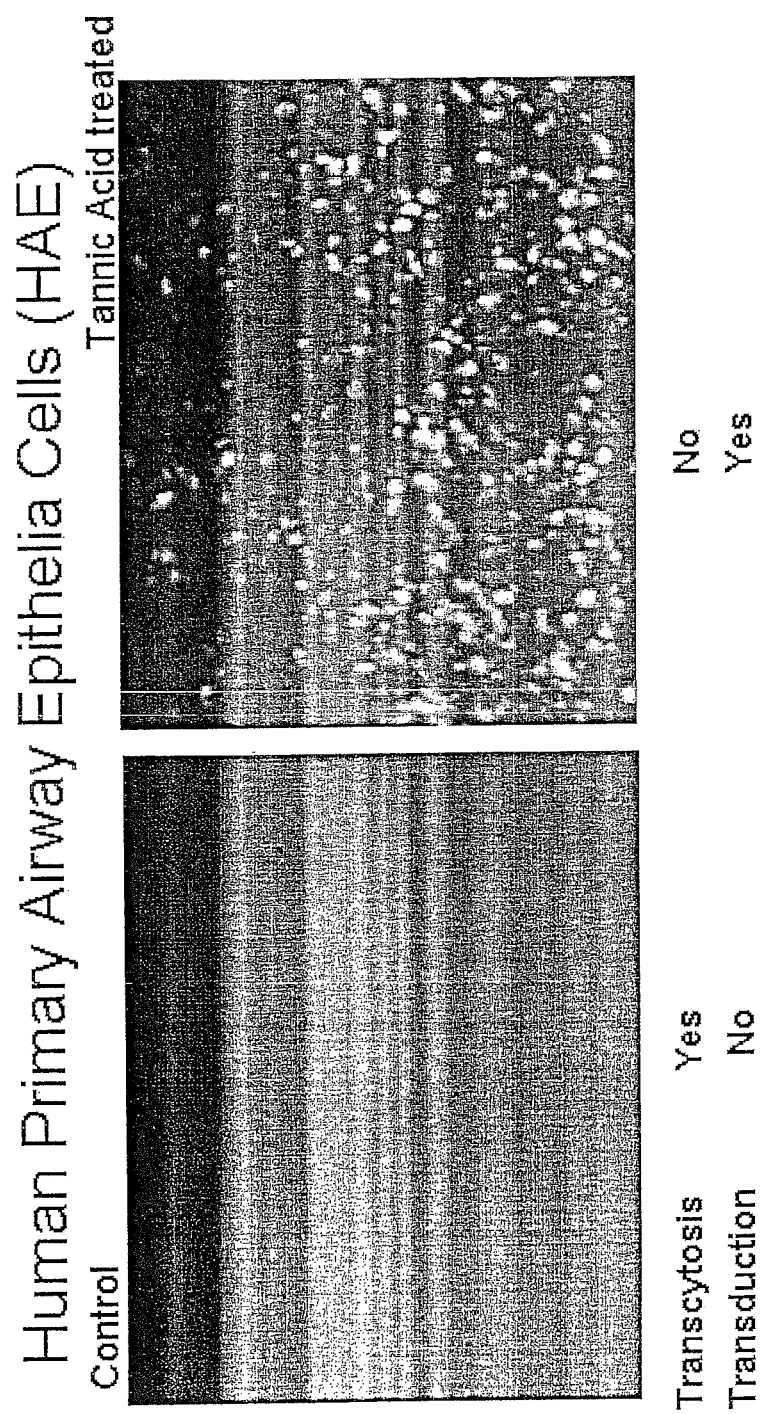
FIG. 14 shows that the treatment of the basal lateral surface of Human primary airways epithelial cell (HAE) with tannic acid blocked the transcytosis of BAAV vector containing a GFP expression cassette from the apical surface to the basal lateral. Furthermore transduction dramatically increased when assayed at 24 hrs post inoculation. In contrast no change was observed in AAV2 transduction, which did not demonstrate any transcytosis activity and has limited binding activity on HAE.

Treatment of the basal lateral surface of Human primary airways epithelial cell (HAE) with tannic acid blocked the transcytosis of BAAV or AAV4 vector containing a GFP expression cassette from the apical surface to the basal lateral (FIG. 14). Furthermore transduction dramatically increased when assayed at 24 hrs post inoculation. In contrast no change was observed in AAV2 transduction, which did not demonstrate any transcytosis activity and has limited binding activity on HAE.

To confirm the DNA detected in the basal lateral media was indeed extracted from intact virus, the material was tested for DNase resistance after treatment with heat, ionic detergent or protease. The addition of DNase alone or in combination with the ionic detergent deoxycholine had no effect on the viral DNA present in the media suggesting it was not free DNA or complexed in lipid vesicles. However, heating to 95° C. prior to treatment with DNAase completely degraded the viral DNA present in the media. This profile is identical to that of the input AAV particles and suggests the viral DNA is still encapsulated. Titration of the DNase resistant virus in the basal lateral media on Cos cells gave a similar particle to infectivity ratio to the input AAV particles.

While it would appear the AAV DNA detected in the basal lateral media is contained in intact particles, its presence on the basal lateral surface could be the result of lyses of the cells or disruption of the monolayer. Therefore the TER was carefully monitored throughout the course of these experiments and was not observed to decrease. To further confirm the integrity of the cell monolayer, mixing experiments were studied in which two viruses with different gene cassettes were added to the apical surface at the same time and three hours post addition the amount of each virus in the basal lateral media was quantified using QPCR specific for each cassette. Both BAAV and AAV5 were able to pass from the apical to the basal lateral surface of MDCK or Caco cells respectively but the AAV2 did not. Therefore the presence of viral particles in the basal lateral media does not appear to be the result of a disruption in the cell monolayer.

Taken together this data suggest that dependoviruses particles are capable of passing through barrier epithelia via transcytosis and the process is both serotype and cell type specific.

To further characterize the transcytosis activity observed with AAV5 and BAAV, transcytosis was quantified as both a time and concentration dependent event. After the addition of particles to the apical surface, samples were removed from the basal lateral media at different time points and the amount of virus was quantified by QPCR of the extracted DNA. Viral genomes could be detected as soon as 30 minutes after addition and steadily increased with time By 24 hrs, over ⅓ of the input recombinant AAV5, BAAVvirus added to Caco or MDCK cells respectively had been transported to the basal lateral surface. In contrast, none of the input AAV2 or adenovirus was detected on the basal lateral side after 24 hrs.

If transcytosis is an activity used by AAV to spread through tissue, this finding would help explain the lack of transduction of barrier epithelia reported with some isolates of AAV. Primary human bronchial airway epithelia (HAE) are known to transport albumin from the apical to the basal lateral surface by receptor-mediated transcytosis in vivo. While the interaction of BAAV with primary HAE has not been investigated, AAV4, 5 are reported to bind to HAE, however, for AAV4, this interaction does not result in transduction. Because of the interaction of AAV4 with O-link sialic acid, it was proposed, and has been demonstrated, that mucins, which contained large amounts of O-linked sialic acid and are expressed on the apical surface of HAE, can block AAV4 transduction. Alternatively the lack of transduction could be the result of transcytosis of the virus through the tissue.

To test this hypothesis, AAV2, 4, 5, BAAV were added to the apical surface of confluent monolayer cultures of primary human bronchial airway and transcytosis to the basal lateral surface was measured by QPCR after 3 hrs. All cultures had high TERs and expressed ciliated structures on their apical surface. Highly differentiated HAE cultures in contrast to immature cultures are resistant to transduction by adenoviral vectors due to a lack of integrin expression that is necessary for adenovirus entry.

Of the 4 AAVs tested for transcytosis, AAV4 and BAAV were detected in the basal lateral media. No transport of AAV2 or AAV5 was detected. As a control, adenovirus also was tested for transcytosis activity in the HAE cultures, but no transport was detected.

Epithelial cells that line the genitourinary tract form an important epithelial barrier layer and can transport proteins by transcytosis. AAV2, 4, 5 or BAAV were therefore tested to determine for the ability to penetrate this barrier epithelial layer by transcytosis. A well-characterized model of endometrial cells has been reported by Kyo et al. Following addition of the 4 AAVs to the apical surface, BAAV and AAV4 could be detected in the basal lateral media when assayed at 3 hrs post inoculation (FIG. 13).

Most AAVs were identified originally as contaminants of laboratory stocks of adenovirus, thus our understanding of their natural biology, cell tropism, and knowledge the cellular components required for virus entry is limited. For AAV5, in addition to N-linked sialic acid, the platelet derived growth factor (PDGF) receptors were identified as protein receptors for AAV5 (Di Pasquale et al., Nat. Med. 2003 October; 9(10): 1306-12). This interaction was confirmed by modulation of PDGFR expression by transfection of expression plasmids, inhibitor treatment, or competition experiments with the extracellular domain of PDGFRα. Likewise AAV5 transduction could be blocked with sialolactosamine conjugates kaludov et al 2001.

Previous research had demonstrated that transcytosis is actin dependent and occurs by a caviolin mediated pathway. Furthermore transcytosis can be blocked by treatment with tannic acid. Therefore to better characterize the transcytosis pathway utilized by AAV5 in Caco cells the cells were treated with a panel of agents known to block either transcytosis in other systems or AAV5 mediated transduction. It was noted that AAV5 transcytosis could be inhibited by filipin and nocozodol as well as treatment with tannic acid.

Caco cells, which actively transcytosis AAV5, are not reported to express PDGFR and are not transduced by AAV5. In agreement, competition experiments with sPDGFRa had little effect on AAV5 transcytosis. Furthermore, competition experiments with 200 ug/ml sialolactosamine or 200 ug/ml heparin did not inhibited AAV5 transcytosis.

Both BSA and transferrin are reported to transcytosis through Caco cells via distinct receptor mediated pathways. However competition with either agent did not inhibit AAV5 transcytosis suggesting the AAV5 could use a distinct pathway.

In addition to confirming the intracellular nature of AAV5 transcytosis in Caco cells, the above experiments suggest that AAV5 transcytosis is occurring by a pathway independent of the one described for transduction. To confirm this Caco cells were stably transfected with PDGFR$^a$ and assayed for both transcytosis and transduction activity. Caco cells were not permissive for AAV5 transduction, however transduction dramatically increase following stable expression of PDGFRa. In contrast only a minor increase in transcytosis activity was detected in the Caco/PDGFRa cells.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

Allen, J. M., Halbert, C. L. and Miller, A. D.: Improved adeno-associated virus vector production with transfection of a single helper adenovirus gene, E4orf6. Mol Ther 1 (2000) 88-95.

Bantel-Schaal, U., Hub, B. and Kartenbeck, J.: Endocytosis of adeno-associated virus type 5 leads to accumulation of virus particles in the Golgi compartment. J Virol 76 (2002) 2340-9.

Bartlett, J. S., Wilcher, R. and Samulski, R. J.: Infectious entry pathway of adeno-associated virus and adeno-associated virus vectors. J Virol 74 (2000) 2777-85.

Ben-Israel, H. and Kleinberger, T.: Adenovirus and cell cycle control. Front Biosci 7 (2002) D1369-95.

Blacklow, N. R., Hoggan, M. D. and Rowe, W. P.: Isolation of adenovirus-associated viruses from man. Proc Natl Acad Sci USA 58 (1967) 1410-5.

Blacklow, N. R., Hoggan, M. D. and Rowe, W. P.: Serologic evidence for human infection with adenovirus-associated viruses. J Natl Cancer Inst 40 (1968) 319-27.

Bossis, I. and Chiorini, J. A.: Cloning of an Avian Adeno-Associated Virus (AAAV) and Generation of Recombinant AAAV Particles. J Virol 77 (2003) 6799-810.

Chiorini, J. A., F. Kim, et al. (1999). "Cloning and characterization of adeno-associated virus type 5." J Virol 73(2): 1309-19.

Chang, L. S. and Shenk, T.: The adenovirus DNA-binding protein stimulates the rate of transcription directed by adenovirus and adeno-associated virus promoters. J Virol 64 (1990) 2103-9.

Chiorini, J. A., Wiener, S. M., Owens, R. A., Kyostio, S. R., Kotin, R. M. and Safer, B.: Sequence requirements for stable binding and function of Rep68 on the adeno-associated virus type 2 inverted terminal repeats. J Virol 68 (1994) 7448-57.

Davidson, B. L., C. S. Stein, et al. (2000). "Recombinant adeno-associated virus type 2, 4, and 5 vectors: transduction of variant cell types and regions in the mammalian central nervous system." Proc Natl Acad Sci USA 97(7): 3428-32.

Derby, M. L., M. Sena-Esteves, et al. (1999). "Gene transfer into the mammalian inner ear using HSV-1 and vaccinia virus vectors." Hear Res 134(1-2): 1-8.

Di Pasquale, G., B. L. Davidson, et al. (2003). "Identification of PDGFR as a receptor for AAV5 transduction." Nat Med 9(10): 1306-12.

Di Pasquale, G., Rzadzinska, A., Schneider, M. E., Bossis, I., Chiorini, J. A., Kachar, B., A novel bovine virus efficiently transduces inner ear neuroepithelial cells, Manuscript submitted.

Erles, K., Sebokova, P. and Schlehofer, J. R.: Update on the prevalence of serum antibodies (IgG and IgM) to adeno-associated virus (AAV). J Med Virol 59 (1999) 406-11.

Gao, G. P., Alvira, M. R., Wang, L., Calcedo, R., Johnston, J. and Wilson, J. M.: Novel adeno-associated viruses from rhesus monkeys as vectors for human gene therapy. Proc Natl Acad Sci USA 99 (2002) 11854-9.

Grimm, D. and M. A. Kay (2003). "From virus evolution to vector revolution: use of naturally occurring serotypes of adeno-associated virus (AAV) as novel vectors for human gene therapy." Curr Gene Ther 3(4): 281-304.

He, D. Z., J. Zheng, et al. (2001). "Development of acetylcholine receptors in cultured outer hair cells." Hear Res 162(1-2): 113-25.

Heister, T., Heid, I. Ackermann, M., Fraefel, C. Herpes simplex virus type l/adeno-associated virus hybrid vectors mediate site-specific integration at the adeno-associated virus preintegration site, AAVS1, on human chromosome 19. J Virol. 2002 July; 76(14):7163-73.

Hoggan, M. D.: Adenovirus associated viruses. Prog Med Virol 12 (1970) 211-39.

Holt, J. R. (2002). "Viral-mediated gene transfer to study the molecular physiology of the Mammalian inner ear." Audiol Neurootol 7(3): 157-60.

Holt, J. R., D. C. Johns, et al. (1999). "Functional expression of exogenous proteins in mammalian sensory hair cells infected with adenoviral vectors." J Neurophysiol 81(4): 1881-8.

Janik, J. E., Huston, M. M., Cho, K. and Rose, J. A.: Efficient synthesis of adeno-associated virus structural proteins requires both adenovirus DNA binding protein and VA I RNA. Virology 168 (1989) 320-9.

Jero J, Mhatre A N, Tseng C J, Stern R E, Coling D E, Goldstein J A, Hong K, Zheng W W, Hogue A T, Lalwani A K. Cochlear gene delivery through an intact round window membrane in mouse. Hum Gene Ther. 2001 Mar. 20; 12(5):539-48.

Kaludov, N., K. E. Brown, et al. (2001). "Adeno-associated virus serotype 4 (AAV4) and AAV5 both require sialic acid binding for hemagglutination and efficient transduction but differ in sialic acid linkage specificity." J Virol 75(15): 6884-93.

Kanzaki, S., K. Ogawa, et al. (2002). "Transgene expression in neonatal mouse inner ear explants mediated by first and advanced generation adenovirus vectors." Hear Res 169(1-2): 112-20.

Katano H, Afione S, Schmidt M, Chiorini J A. Identification of adeno-associated virus contamination in cell and virus stocks by PCR. Biotechniques. 2004 April; 36(4):676-80.

Kelsell, D. P., Dunlop, J., Stevens, H. P., Lench, N. J., Liang, J. N., Parry, G., Mueller, R. F., Leigh, I. M. Connexin 26 mutations in hereditary non-syndromic sensorineural deafness. Nature. 1997 May 1; 387(6628):80-3

Kern, A., K. Schmidt, et al. (2003). "Identification of a heparin-binding motif on adeno-associated virus type 2 capsids." J Virol 77(20): 11072-81.

Li Duan, M., T. Bordet, et al. (2002). "Adenoviral and adeno-associated viral vector mediated gene transfer in the guinea pig cochlea." Neuroreport 13(10): 1295-9.

Luchsinger, E., Strobbe, R., Dekegel, D. and Wellemans, G.: Use of B-IV zonal rotor centrifugation as a simple tool for the separation of adeno-associated X 7 virus (AAVX 7) from helper adenoviruses. Arch Gesamte Virusforsch 33 (1971) 251-8.

Luchsinger, E., Strobbe, R., Wellemans, G., Dekegel, D. and Sprecher-Goldberger, S.: Haemagglutinating adeno-associated virus (AAV) in association with bovine adenovirus type 1. Brief report. Arch Gesamte Virusforsch 31 (1970) 390-2.

Luebke, A. E., P. K. Foster, et al. (2001). "Cochlear function and transgene expression in the guinea pig cochlea, using adenovirus- and adeno-associated virus-directed gene transfer." Hum Gene Ther 12(7): 773-81.

Luebke, A. E., J. D. Steiger, et al. (2001). "A modified adenovirus can transfect cochlear hair cells in vivo without compromising cochlear function." Gene Ther 8(10): 789-94.

Meyers, C., Mane, M., Kokorina, N., Alam, S. and Hermonat, P. L.: Ubiquitous human adeno-associated virus type 2 autonomously replicates in differentiating keratinocytes of a normal skin model. Virology 272 (2000) 338-46.

Mouw, M. B. and Pintel, D. J.: Adeno-associated virus RNAs appear in a temporal order and their splicing is stimulated during coinfection with adenovirus. J Virol 74 (2000) 9878-88.

Muramatsu, S., H. Mizukami, et al. (1996). "Nucleotide sequencing and generation of an infectious clone of adeno-associated virus 3." Virology 221(1): 208-17.

Myrup, A. C., Mohanty, S. B. and Hetrick, F. M.: Isolation and characterization of adeno-associated viruses from bovine adenovirus types 1 and 2. Am J Vet Res 37 (1976) 907-10.

Naz, S., Griffit, h A. J., Riazuddin, S., Hampton, L. L., Battey, J. F. Jr, Khan, S. N., Riazuddin, S., Wilcox, E. R., Friedman, T. B. Mutations of ESPN cause autosomal recessive deafness and vestibular dysfunction. J Med. Genet. 2004 August; 41(8):591-5.

No D, Yao T P, Evans R M. (1996). Ecdysone-inducible gene expression in mammalian cells and transgenic mice. Proc Natl Acad Sci USA. 93(8):3346-51.

Opie, S. R., K. H. Warrington, Jr., et al. (2003). "Identification of amino acid residues in the capsid proteins of adeno-associated virus type 2 that contribute to heparan sulfate proteoglycan binding." J Virol 77(12): 6995-7006.

Rabinowitz J E, Bowles D E, Faust S M, Ledford J G, Cunningham S E, Samulski R J. Cross-dressing the virion: the transcapsidation of adeno-associated virus serotypes functionally defines subgroups. J. Virol. 2004 May; 78(9):4421-32.

Rzadzinska, A. K., M. E. Schneider, et al. (2004). "An actin molecular treadmill and myosins maintain stereocilia functional architecture and self-renewal." J Cell Biol 164(6): 887-97.

Sanlioglu, S., Benson, P. K., Yang, J., Atkinson, E. M., Reynolds, T. and Engelhardt, J. F.: Endocytosis and nuclear trafficking of adeno-associated virus type 2 are controlled by rac1 and phosphatidylinositol-3 kinase activation. J Virol 74 (2000) 9184-96.

Saffer, L. D., R. Gu, et al. (1996). "An RT-PCR analysis of mRNA for growth factor receptors in damaged and control sensory epithelia of rat utricles." Hear Res 94(1-2): 14-23.

Schmidt, M., H. Katano, et al. (2004). "Cloning and characterization of a bovine adeno-associated virus." J Virol 78(12): 6509-16.

Schneider, M. E., I. A. Belyantseva, et al. (2002). "Rapid renewal of auditory hair bundles." Nature 418(6900): 837-8.

Shou, J., J. L. Zheng, et al. (2003). "Robust generation of new hair cells in the mature mammalian inner ear by adenoviral expression of Hath1." Mol Cell Neurosci 23(2): 169-79.

Smith, R. H., S. A. Afione, et al. (2002). "Transposase-mediated construction of an integrated adeno-associated virus type 5 helper plasmid." Biotechniques 33(1): 204-6, 208, 210-1.

Sobkowicz, H. M., J. M. Loftus, et al. (1993). "Tissue culture of the organ of Corti." Acta Otolaryngol Suppl 502: 3-36.

Staecker H, Li D, O'Malley B W Jr, Van De Water T R. Gene expression in the mammalian cochlea: a study of multiple vector systems. Acta Otolaryngol. 2001 January; 121(2): 157-63.

Summerford, C. and R. J. Samulski (1998). "Membrane-associated heparan sulfate proteoglycan is a receptor for adeno-associated virus type 2 virions." J Virol 72(2): 1438-45.

Suzuki, H., Y. Katori, et al. (1995). "Carbohydrate distribution in the living utricular macula of the guinea pig detected by lectins." Hear Res 87(1-2): 32-40.

Walters, R. W., Yi, S. M., Keshavjee, S., Brown, K. E., Welsh, M. J., Chiorini, J. A. and Zabner, J.: Binding of adeno-associated virus type 5 to 2,3-linked sialic acid is required for gene transfer. J Biol Chem 276 (2001) 20610-6.

Yakinoglu, A. O., Heilbronn, R., Burkle, A., Schlehofer, J. R. and zur Hausen, H.: DNA amplification of adeno-associated virus as a response to cellular genotoxic stress. Cancer Res 48 (1988) 3123-9.

Yakobson, B., Hrynko, T. A., Peak, M. J. and Winocour, E.: Replication of adeno-associated virus in cells irradiated with UV light at 254 nm. J Virol 63 (1989) 1023-30.

Yamano, S., Huang, L. Y., Ding, C., Chiorini, J. A., Goldsmith, C. M., Wellner, R. B., Golding, B., Kotin, R. M., Scott, D. E. and Baum, B. J.: Recombinant adeno-associated virus serotype 2 vectors mediate stable interleukin 10 secretion from salivary glands into the bloodstream. Hum Gene Ther 13 (2002) 287-98.

Zabner, J., Seiler, M., Walters, R., Kotin, R. M., Fulgeras, W., Davidson, B. L., Chiorini, J. A. Adeno-associated virus type 5 (AAV5) but not AAV2 binds to the apical surfaces of airway epithelia and facilitates gene transfer. J Virol. 2000 April; 74(8):3852-8.

---

What is claimed is:

1. A vector comprising a nucleic acid molecule encoding a protein comprising an amino acid sequence selected from the group consisting of SEQ ID NO:7, SEQ ID NO:9 and SEQ ID NO:11.

2. The vector of claim 1, wherein the nucleic acid molecule comprises a sequence selected from the group consisting of SEQ ID NO:6, SEQ ID NO:8 and SEQ ID NO:10.

\* \* \* \* \*

SEQUENCE LISTING

```
<160> NUMBER OF SEQ ID NOS: 25

<210> SEQ ID NO 1
<211> LENGTH: 4694
<212> TYPE: DNA
<213> ORGANISM: Artificial Sequence
<220> FEATURE:
<223> OTHER INFORMATION: synthetic construct

<400> SEQUENCE: 1
gtggcactcc ccccctgtc gcgttcgctc gttcgctggc tcgattgggg gggtggcagc      60
tcaaagagct gccagacgac ggccctctgg gccgtcgccc ccccaatcga gccagcgaac    120
gagcgaacgc gacaggggg ggagtgccac actctctagc aaggggggttt tgtaggtggt    180 gatgtcattg ttgatgtcat tatagttgtc acgcgatagt taatgattaa cagtcatgtg    240
atgtgtgtta tccaatagga tgaaagcgcg cgaatgagat ctcgcgagac ttccggggta    300
taaaaggggt gagtgaacga gcccgccgcc attctctgct ctggactgct agaggaccct    360
cgctgccatg gctaccttct atgaagtcat tgttcgcgtt ccatttgatg tggaagagca    420
cctgcctgga atttctgaca actttgtaga ctgggtaact ggtcaaattt gggagctgcc    480
tcccgagtca gatttgaatt tgactctgat tgagcagcct cagctgacgg tggctgacag    540
```

```
aattcgccgc gtgttcctgt acgagtggaa caaattttcc aagcaggaga gcaaattctt      600
tgtgcagttt gaaaagggat ctgaatattt tcatctgcac acgctcgtgg agacctccgg      660
catctcttct atggtccttg ccgctacgt gagtcagatt cgcgcccagc tggtgaaggt       720
ggtgttccag aacattgagc cgcggattaa cgactgggtc gccatcacca aggtaaagaa      780
gggcggagcc aataaggtgg tggattctgg gtatattccc gcctacctgc tgccgaaggt      840
ccaaccagag cttcagtggg cgtggactaa cctcgaagag tataaattgg ccgccctcaa      900
tctggaggag cgcaaacggc tcgtcgctca gtttcagctt gagtcctcgc agcgctcgca      960
agaggcatct tcccagaggg acgtttcggc tgacccggtc atcaagagca agacttccca     1020
gaaatacatg gcgctggtaa gctggctggt ggaacatggc atcacttccg agaagcagtg     1080
gattcaggag aatcaggaga gctacctgtc cttcaactcc acgggaaact ctcggagcca     1140
gattaaagcc gcgcttgaca acgcgtcaaa aattatgagt ctgaccaaat ctgcctcaga     1200
ctatctcgtg ggacagactg ttccagagga catttctgaa aacagaatct ggcagatttt     1260
tgatctcaac ggctacgacc cggcatacgc gggctctgtt ctctacggct ggtgcactcg     1320
cgcctttgga aagaggaaca ccgtctggct gtatggaccc cgcgaccacg gaaagaccaa     1380
catcgcggaa gccatctctc acaccgtgcc cttttatggc tgtgtgaact ggactaatga     1440
gaactttccc tttaatgact gtgtggaaaa aatgttgatc tggtgggagg agggaaagat     1500
gaccagcaag gtggtggaac ccgccaaggc catcttgggg gggtctagag tacgagtgga     1560
tcaaaaatgt aaatcctctg tacaagtaga ctctaccccg gtgattatca cctccaatac     1620
taacatgtgt gtggtggtgg atgggaactc cacgaccttt gaacaccagc agccgctgga     1680
agaccgcatg ttcagatttg aactcatgcg gcggctcccg ccagattttg caagattac      1740
caagcaggaa gtcaaagact ttttttgcttg gcaaaggtc aaccaggtgc cggtgactca     1800
cgagtttatg gttcccaaga agtggcggg aactgagagg cgcgagactt ctagaaaacg      1860
cccactggat gacgtcacca ataccaacta taaaagtccg gagaagcggg cccggctctc     1920
agttgttcct gagacgcctc gcagttcaga cgtgcctgta gagcccgctc ctctgcgacc     1980
tctcaactgg tcttccaggt atgaatgcag atgtgactat catgctaaat ttgactctgt     2040
aacgggggaa tgtgacgagt gtgaatattt gaatcggggc aaaaatggct gtatctttca     2100
taatgctaca cattgtcaaa tttgtcacgc tgttcctcca tgggaaaagg aaaatgtgtc     2160
agattttaat gattttgatg actgtaataa agagcagtaa ataaagtgag tagtcatgtc     2220
ttttgttgac caccctccag attggttgga atcgatcggc gacggctttc gtgaatttct     2280
cggccttgag gcgggtcccc cgaaacccaa ggccaatcaa cagaagcaag ataacgctcg     2340
aggtcttgtg cttcctgggt acaagtatct tggtcctggg aacggccttg ataagggcga     2400
tcctgtcaat tttgctgacg aggttgcccg agagcacgac ctctcctacc agaaacagct     2460
tgaggcgggc gataaccctt acctcaagta caaccacgcg gacgcagagt tcaggagaa      2520
actcgcttct gacacttctt ttgggggaaa ccttgggaag gctgttttcc aggctaaaaa     2580
gaggattctc gaacctcttg gcctggttga cgcccggat aaaacggcgc ctgcggcaaa      2640
aaagaggcct ctagagcaga gtcctcaaga gccagactcc tcgagcggag ttggcaagaa     2700
aggcaaacag cctgccagaa agagactcaa cttttgacgac gaacctggag ccggagacgg     2760
gcctcccccc gaaggaccat cttccggagc tatgtctact gagactgaaa tgcgtgcagc     2820
agctggcgga aatggtggcg atgcgggaca aggtgccgag ggagtgggta atgcctccgg     2880
tgattggcat tgcgattcca cttggtcaga gagccacgtc accaccacct caacccgcac     2940
```

```
ctgggtcctg ccgacctaca acaaccacct gtacctgcgg ctcggctcga gcaacgccag    3000
cgacaccttc aacggattct ccacccctg gggatacttt gactttaacc gcttccactg     3060
ccacttctcg ccaagagact ggcaaaggct catcaacaac cactggggac tgcgccccaa    3120
aagcatgcaa gtccgcatct tcaacatcca agttaaggag gtcacgacgt ctaacgggga    3180
gacgaccgta tccaacaacc tcaccagcac ggtccagatc tttgcggaca gcacgtacga    3240
gctcccgtac gtgatggatg caggtcagga gggcagcttg cctcctttcc ccaacgacgt    3300
gttcatggtg cctcagtacg ggtactgcgg actggtaacc ggaggcagct ctcaaaacca    3360
gacagacaga aatgccttct actgtctgga gtactttccc agccagatgc tgagaaccgg    3420
aaacaacttt gagatggtgt acaagtttga aaacgtgccc ttccactcca tgtacgctca    3480
cagccagagc ctggataggc tgatgaaccc gctgctggac cagtacctgt gggagctcca    3540
gtctaccacc tctggaggaa ctctcaacca gggcaattca gccaccaact ttgccaagct    3600
gaccaaaaca aacttttctg gctaccgcaa aaactggctc ccggggccca tgatgaagca    3660
gcagagattc tccaagactg ccagtcaaaa ctacaagatt ccccagggaa gaaacaacag    3720
tctgctccat tatgagacca gaactaccct cgacggaaga tggagcaatt ttgccccggg    3780
aacggccatg gcaaccgcag ccaacgacgc caccgacttc tctcaggccc agctcatctt    3840
tgcggggccc aacatcaccg gcaacaccac cacagatgcc aataacctga tgttcacttc    3900
agaagatgaa cttagggcca ccaacccccg ggacactgac ctgtttggcc acctggcaac    3960
caaccagcaa aacgccacca ccgttcctac cgtagacgac gtggacgagt cggcgtgta    4020 cccgggaatg gtgtggcagg acagagacat ttactaccaa gggcccattt gggccaaaat    4080
tccacacacg gatggacact ttcacccgtc tcctctcatt ggcggatttg gactgaaaag    4140
cccgcctcca caaatattca tcaaaaacac tcctgtaccc gccaatcccg caacgacctt    4200
ctctccggcc agaatcaaca gcttcatcac ccagtacagc accggacagg tggctgtcaa    4260
aatagaatgg gaaatccaga aggagcggtc caagagatgg aacccagagg tccagttcac    4320
gtccaactac ggagcacagg actcgcttct ctgggctccc gacaacgccg gagcctacaa    4380
agagcccagg gccattggat cccgatacct caccaaccac ctctagccca attctgttgc    4440 atacctcaa taaaccgtgt attcgtttca gtaaaatact gcctcttgtg gtcattcggc     4500
gtacaacagc ttcaacaac aacaaaaccc ccttgctaga gagtgtggca ctccccccc     4560 tgtcgcgttc gctcgttcgc tggctcgatt gggggggtgg cagctcaaag agctgccaga    4620
cgacggccct ctgggccgtc gcccccccaa tcgagccagc gaacgagcga acgcgacagg    4680 gggggagtg ccac                                                      4694
```

<210> SEQ ID NO 2
<211> LENGTH: 1833
<212> TYPE: DNA
<213> ORGANISM: Artificial Sequence
<220> FEATURE:
<223> OTHER INFORMATION: synthetic construct

<400> SEQUENCE: 2

```
atggctacct tctatgaagt cattgttcgc gttccatttg atgtggaaga gcacctgcct      60
ggaatttctg acaactttgt agactgggta actggtcaaa tttgggagct gcctcccgag    120
tcagatttga atttgactct gattgagcag cctcagctga cggtggctga cagaattcgc    180 ccgtgttcc tgtacgagtg aacaaattt tccaagcagg agagcaaatt ctttgtgcag     240
tttgaaaagg gatctgaata ttttcatctg cacacgctcg tggagacctc cggcatctct    300
```

```
tctatggtcc ttggccgcta cgtgagtcag attcgcgccc agctggtgaa ggtggtgttc    360
cagaacattg agccgcggat taacgactgg gtcgccatca ccaaggtaaa gaagggcgga    420
gccaataagg tggtggattc tgggtatatt cccgcctacc tgctgccgaa ggtccaacca    480
gagcttcagt gggcgtggac taacctcgaa gagtataaat tggccgccct caatctggag    540
gagcgcaaac ggctcgtcgc tcagtttcag cttgagtcct cgcagcgctc gcaagaggca    600
tcttcccaga gggacgtttc ggctgacccg gtcatcaaga gcaagacttc ccagaaatac    660
atggcgctgg taagctggct ggtggaacat ggcatcactt ccgagaagca gtggattcag    720
gagaatcagg agagctacct gtccttcaac tccacgggaa actctcggag ccagattaaa    780
gccgcgcttg acaacgcgtc aaaaattatg agtctgacca atctgcctc agactatctc     840 gtgggacaga ctgttccaga ggacatttct gaaaacagaa tctggcagat ttttgatctc    900
aacggctacg acccggcata cgcgggctct gttctctacg ctggtgcac tcgcgccttt     960 ggaaagagga acaccgtctg gctgtatgga cccgcgacca ccggaaagac caacatcgcg   1020
gaagccatct ctcacaccgt gccctttat ggctgtgtga actggactaa tgagaacttt    1080
ccctttaatg actgtgtgga aaaaatgttg atctggtggg aggagggaaa gatgaccagc   1140
aaggtggtgg aacccgccaa ggccatcttg gggggtcta gagtacgagt ggatcaaaaa    1200
tgtaaatcct ctgtacaagt agactctacc ccggtgatta tcacctccaa tactaacatg   1260
tgtgtggtgg tggatgggaa ctccacgacc tttgaacacc agcagccgct ggaagaccgc   1320
atgttcagat ttgaactcat gcggcggctc ccgccagatt ttggcaagat taccaagcag   1380
gaagtcaaag actttttgc ttgggcaaag gtcaaccagg tgccggtgac tcacgagttt    1440
atggttccca gaaagtggc gggaactgag agggcggaga cttctagaaa acgcccactg    1500
gatgacgtca ccaataccaa ctataaaagt ccggagaagc gggcccggct ctcagttgtt   1560
cctgagacgc ctcgcagttc agacgtgcct gtagagcccg ctcctctgcg acctctcaac   1620
tggtcttcca ggtatgaatg cagatgtgac tatcatgcta aatttgactc tgtaacgggg   1680
gaatgtgacg agtgtgaata tttgaatcgg ggcaaaaatg gctgtatctt tcataatgct   1740
acacattgtc aaatttgtca cgctgttcct ccatgggaaa aggaaaatgt gtcagatttt   1800
aatgattttg atgactgtaa taagagcag  taa                                1833
```

<210> SEQ ID NO 3
<211> LENGTH: 610
<212> TYPE: PRT
<213> ORGANISM: Artificial Sequence
<220> FEATURE:
<223> OTHER INFORMATION: synthetic construct

<400> SEQUENCE: 3

```
Met Ala Thr Phe Tyr Glu Val Ile Val Arg Val Pro Phe Asp Val Glu
1               5                   10                  15

Glu His Leu Pro Gly Ile Ser Asp Asn Phe Val Asp Trp Val Thr Gly
            20                  25                  30

Gln Ile Trp Glu Leu Pro Pro Glu Ser Asp Leu Asn Leu Thr Leu Ile
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95
```

```
Ser Gly Ile Ser Ser Met Val Leu Gly Arg Tyr Val Ser Gln Ile Arg
        100                 105                 110

Ala Gln Leu Val Lys Val Val Phe Gln Asn Ile Glu Pro Arg Ile Asn
        115                 120                 125

Asp Trp Val Ala Ile Thr Lys Val Lys Lys Gly Gly Ala Asn Lys Val
        130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Glu Glu Tyr Lys Leu Ala Ala
                165                 170                 175

Leu Asn Leu Glu Glu Arg Lys Arg Leu Val Ala Gln Phe Gln Leu Glu
            180                 185                 190

Ser Ser Gln Arg Ser Gln Glu Ala Ser Ser Gln Arg Asp Val Ser Ala
        195                 200                 205

Asp Pro Val Ile Lys Ser Lys Thr Ser Gln Lys Tyr Met Ala Leu Val
        210                 215                 220

Ser Trp Leu Val Glu His Gly Ile Thr Ser Glu Lys Gln Trp Ile Gln
225                 230                 235                 240

Glu Asn Gln Glu Ser Tyr Leu Ser Phe Asn Ser Thr Gly Asn Ser Arg
                245                 250                 255

Ser Gln Ile Lys Ala Ala Leu Asp Asn Ala Ser Lys Ile Met Ser Leu
            260                 265                 270

Thr Lys Ser Ala Ser Asp Tyr Leu Val Gly Gln Thr Val Pro Glu Asp
        275                 280                 285

Ile Ser Glu Asn Arg Ile Trp Gln Ile Phe Asp Leu Asn Gly Tyr Asp
        290                 295                 300

Pro Ala Tyr Ala Gly Ser Val Leu Tyr Gly Trp Cys Thr Arg Ala Phe
305                 310                 315                 320

Gly Lys Arg Asn Thr Val Trp Leu Tyr Gly Pro Ala Thr Thr Gly Lys
                325                 330                 335

Thr Asn Ile Ala Glu Ala Ile Ser His Thr Val Pro Phe Tyr Gly Cys
            340                 345                 350

Val Asn Trp Thr Asn Glu Asn Phe Pro Phe Asn Asp Cys Val Glu Lys
        355                 360                 365

Met Leu Ile Trp Trp Glu Glu Gly Lys Met Thr Ser Lys Val Val Glu
        370                 375                 380

Pro Ala Lys Ala Ile Leu Gly Gly Ser Arg Val Arg Val Asp Gln Lys
385                 390                 395                 400

Cys Lys Ser Ser Val Gln Val Asp Ser Thr Pro Val Ile Ile Thr Ser
                405                 410                 415

Asn Thr Asn Met Cys Val Val Asp Gly Asn Ser Thr Thr Phe Glu
            420                 425                 430

His Gln Gln Pro Leu Glu Asp Arg Met Phe Arg Phe Glu Leu Met Arg
        435                 440                 445

Arg Leu Pro Pro Asp Phe Gly Lys Ile Thr Lys Gln Glu Val Lys Asp
        450                 455                 460

Phe Phe Ala Trp Ala Lys Val Asn Gln Val Pro Val Thr His Glu Phe
465                 470                 475                 480

Met Val Pro Lys Lys Val Ala Gly Thr Glu Arg Ala Glu Thr Ser Arg
                485                 490                 495

Lys Arg Pro Leu Asp Asp Val Thr Asn Thr Asn Tyr Lys Ser Pro Glu
            500                 505                 510

Lys Arg Ala Arg Leu Ser Val Val Pro Glu Thr Pro Arg Ser Ser Asp
```

```
                515              520                 525
Val Pro Val Glu Pro Ala Pro Leu Arg Pro Leu Asn Trp Ser Ser Arg
    530                 535                 540

Tyr Glu Cys Arg Cys Asp Tyr His Ala Lys Phe Asp Ser Val Thr Gly
545                 550                 555                 560

Glu Cys Asp Glu Cys Glu Tyr Leu Asn Arg Gly Lys Asn Gly Cys Ile
                565                 570                 575

Phe His Asn Ala Thr His Cys Gln Ile Cys His Ala Val Pro Pro Trp
                580                 585                 590

Glu Lys Glu Asn Val Ser Asp Phe Asn Asp Phe Asp Asp Cys Asn Lys
            595                 600                 605

Glu Gln
    610

<210> SEQ ID NO 4
<211> LENGTH: 1173
<212> TYPE: DNA
<213> ORGANISM: Artificial Sequence
<220> FEATURE:
<223> OTHER INFORMATION: synthetic construct

<400> SEQUENCE: 4
atggcgctgg taagctggct ggtggaacat ggcatcactt ccgagaagca gtggattcag        60
gagaatcagg agagctacct gtccttcaac tccacgggaa actctcggag ccagattaaa       120
gccgcgcttg acaacgcgtc aaaaattatg agtctgacca atctgcctc agactatctc        180 gtgggacaga ctgttccaga ggacatttct gaaaacagaa tctggcagat ttttgatctc       240
aacggctacg acccggcata cgcgggctct gttctctacg gctggtgcac tcgcgccttt       300
ggaaagagga acaccgtctg gctgtatgga cccgcgacca ccggaaagac caacatcgcg       360
gaagccatct ctcacaccgt gccctttat ggctgtgtga actggactaa tgagaacttt        420
ccctttaatg actgtgtgga aaaaatgttg atctggtggg aggagggaaa gatgaccagc       480
aaggtggtgg aacccgccaa ggccatcttg gggggtcta gagtacgagt ggatcaaaaa       540
tgtaaatcct ctgtacaagt agactctacc ccggtgatta tcacctccaa tactaacatg       600
tgtgtggtgg tggatgggaa ctccacgacc tttgaacacc agcagccgct ggaagaccgc       660
atgttcagat ttgaactcat gcggcggctc ccgccagatt ttggcaagat taccaagcag       720
gaagtcaaag actttttgc ttgggcaaag gtcaaccagg tgccggtgac tcacgagttt        780
atggttccca gaaagtggc gggaactgag agggcggaga cttctagaaa acgcccactg        840
gatgacgtca ccaataccaa ctataaaagt ccggagaagc gggcccggct ctcagttgtt       900
cctgagacgc ctcgcagttc agacgtgcct gtagagcccg ctcctctgcg acctctcaac       960
tggtcttcca ggtatgaatg cagatgtgac tatcatgcta aatttgactc tgtaacgggg      1020
gaatgtgacg agtgtgaata tttgaatcgg ggcaaaaatg gctgtatctt catctaatgct    1080 acacattgtc aaatttgtca cgctgttcct ccatgggaaa aggaaaatgt gtcagatttt      1140
aatgattttg atgactgtaa taagagcag taa                                    1173

<210> SEQ ID NO 5
<211> LENGTH: 390
<212> TYPE: PRT
<213> ORGANISM: Artificial Sequence
<220> FEATURE:
<223> OTHER INFORMATION: synthetic construct

<400> SEQUENCE: 5
```

```
Met Ala Leu Val Ser Trp Leu Val Glu His Gly Ile Thr Ser Glu Lys
 1               5                  10                  15

Gln Trp Ile Gln Glu Asn Gln Glu Ser Tyr Leu Ser Phe Asn Ser Thr
            20                  25                  30

Gly Asn Ser Arg Ser Gln Ile Lys Ala Ala Leu Asp Asn Ala Ser Lys
        35                  40                  45

Ile Met Ser Leu Thr Lys Ser Ala Ser Asp Tyr Leu Val Gly Gln Thr
 50                  55                  60

Val Pro Glu Asp Ile Ser Glu Asn Arg Ile Trp Gln Ile Phe Asp Leu
 65                  70                  75                  80

Asn Gly Tyr Asp Pro Ala Tyr Ala Gly Ser Val Leu Tyr Gly Trp Cys
                85                  90                  95

Thr Arg Ala Phe Gly Lys Arg Asn Thr Val Trp Leu Tyr Gly Pro Ala
            100                 105                 110

Thr Thr Gly Lys Thr Asn Ile Ala Glu Ala Ile Ser His Thr Val Pro
        115                 120                 125

Phe Tyr Gly Cys Val Asn Trp Thr Asn Glu Asn Phe Pro Phe Asn Asp
    130                 135                 140

Cys Val Glu Lys Met Leu Ile Trp Trp Glu Glu Gly Lys Met Thr Ser
145                 150                 155                 160

Lys Val Val Glu Pro Ala Lys Ala Ile Leu Gly Gly Ser Arg Val Arg
                165                 170                 175

Val Asp Gln Lys Cys Lys Ser Ser Val Gln Val Asp Ser Thr Pro Val
            180                 185                 190

Ile Ile Thr Ser Asn Thr Asn Met Cys Val Val Asp Gly Asn Ser
        195                 200                 205

Thr Thr Phe Glu His Gln Gln Pro Leu Glu Asp Arg Met Phe Arg Phe
    210                 215                 220

Glu Leu Met Arg Arg Leu Pro Pro Asp Phe Gly Lys Ile Thr Lys Gln
225                 230                 235                 240

Glu Val Lys Asp Phe Phe Ala Trp Ala Lys Val Asn Gln Val Pro Val
                245                 250                 255

Thr His Glu Phe Met Val Pro Lys Lys Val Ala Gly Thr Glu Arg Ala
            260                 265                 270

Glu Thr Ser Arg Lys Arg Pro Leu Asp Asp Val Thr Asn Thr Asn Tyr
        275                 280                 285

Lys Ser Pro Glu Lys Arg Ala Arg Leu Ser Val Val Pro Glu Thr Pro
    290                 295                 300

Arg Ser Ser Asp Val Pro Val Glu Pro Ala Pro Leu Arg Pro Leu Asn
305                 310                 315                 320

Trp Ser Ser Arg Tyr Glu Cys Arg Cys Asp Tyr His Ala Lys Phe Asp
                325                 330                 335

Ser Val Thr Gly Glu Cys Asp Glu Cys Glu Tyr Leu Asn Arg Gly Lys
            340                 345                 350

Asn Gly Cys Ile Phe His Asn Ala Thr His Cys Gln Ile Cys His Ala
        355                 360                 365

Val Pro Pro Trp Glu Lys Glu Asn Val Ser Asp Phe Asn Asp Phe Asp
    370                 375                 380

Asp Cys Asn Lys Glu Gln
385                 390

<210> SEQ ID NO 6
<211> LENGTH: 2211
<212> TYPE: DNA
<213> ORGANISM: Artificial Sequence
```

<220> FEATURE:
<223> OTHER INFORMATION: synthetic construct

<400> SEQUENCE: 6

| | | | | | |
|---|---|---|---|---|---|
| atgtcttttg | ttgaccaccc | tccagattgg | ttggaatcga | tcggcgacgg | ctttcgtgaa | 60 |
| tttctcggcc | ttgaggcggg | tccccgaaa | cccaaggcca | atcaacagaa | gcaagataac | 120 |
| gctcgaggtc | ttgtgcttcc | tgggtacaag | tatcttggtc | ctgggaacgg | ccttgataag | 180 |
| ggcgatcctg | tcaattttgc | tgacgaggtt | gcccgagagc | acgacctctc | ctaccagaaa | 240 |
| cagcttgagg | cgggcgataa | cccttacctc | aagtacaacc | acgcggacgc | agagtttcag | 300 |
| gagaaactcg | cttctgacac | ttcttttggg | ggaaaccttg | ggaaggctgt | tttccaggct | 360 |
| aaaaagagga | ttctcgaacc | tcttggcctg | gttgagacgc | cggataaaac | ggcgcctgcg | 420 |
| gcaaaaaaga | ggcctctaga | gcagagtcct | caagagccag | actcctcgag | cggagttggc | 480 |
| aagaaaggca | aacagcctgc | cagaaagaga | ctcaactttg | acgacgaacc | tggagccgga | 540 |
| gacgggcctc | cccagaagg | accatcttcc | ggagctatgt | ctactgagac | tgaaatgcgt | 600 |
| gcagcagctg | gcggaaatgg | tggcgatgcg | ggacaaggtg | ccgagggagt | gggtaatgcc | 660 |
| tccggtgatt | ggcattgcga | ttccacttgg | tcagagagcc | acgtcaccac | cacctcaacc | 720 |
| cgcacctggg | tcctgccgac | ctacaacaac | cacctgtacc | tgcggctcgg | ctcgagcaac | 780 |
| gccagcgaca | ccttcaacgg | attctccacc | ccctggggat | actttgactt | taaccgcttc | 840 |
| cactgccact | tctcgccaag | agactggcaa | aggctcatca | acaaccactg | ggactgcgc | 900 |
| cccaaaagca | tgcaagtccg | catcttcaac | atccaagtta | aggaggtcac | gacgtctaac | 960 |
| ggggagacga | ccgtatccaa | caacctcacc | agcacggtcc | agatctttgc | ggacagcacg | 1020 |
| tacgagctcc | cgtacgtgat | ggatgcaggt | caggagggca | gcttgcctcc | tttccccaac | 1080 |
| gacgtgttca | tggtgcctca | gtacgggtac | tgcggactgg | taaccggagg | cagctctcaa | 1140 |
| aaccagacag | acagaaatgc | cttctactgt | ctggagtact | ttcccagcca | gatgctgaga | 1200 |
| accggaaaca | actttgagat | ggtgtacaag | tttgaaaacg | tgcccttcca | ctccatgtac | 1260 |
| gctcacagcc | agagcctgga | taggctgatg | aacccgctgc | tggaccagta | cctgtgggag | 1320 |
| ctccagtcta | ccacctctgg | aggaactctc | aaccagggca | attcagccac | caactttgcc | 1380 |
| aagctgacca | aaacaaactt | ttctggctac | cgcaaaaact | ggctcccggg | gcccatgatg | 1440 |
| aagcagcaga | gattctccaa | gactgccagt | caaaactaca | agattcccca | gggaagaaac | 1500 |
| aacagtctgc | tccattatga | gaccagaact | acccctgacg | gaagatggag | caattttgcc | 1560 |
| ccgggaacgg | ccatggcaac | cgcagccaac | gacgccaccg | acttctctca | ggcccagctc | 1620 |
| atctttgcgg | ggcccaacat | caccggcaac | accaccacag | atgccaataa | cctgatgttc | 1680 |
| acttcagaag | atgaacttag | ggccaccaac | ccccgggaca | ctgacctgtt | tggccacctg | 1740 |
| gcaaccaacc | agcaaaacgc | caccaccgtt | cctaccgtag | acgacgtgga | cggagtcggc | 1800 |
| gtgtacccgg | gaatggtgtg | gcaggacaga | gacatttact | accaagggcc | catttgggcc | 1860 |
| aaaattccac | acacgatgg | acactttcac | ccgtctcctc | tcattggcgg | atttggactg | 1920 |
| aaaagcccgc | ctcacaaat | attcatcaaa | aacactcctg | tacccgccaa | tcccgcaacg | 1980 |
| accttctctc | cggccagaat | caacagcttc | atcacccagt | acagcaccgg | acaggtggct | 2040 |
| gtcaaaatag | aatgggaaat | ccagaaggag | cggtccaaga | gatggaaccc | agaggtccag | 2100 |
| ttcacgtcca | actacggagc | acaggactcg | cttctctggg | ctcccgacaa | cgccggagcc | 2160 |
| tacaaagagc | ccagggccat | tggatcccga | tacctcacca | ccacctcta | g | 2211 |

```
<210> SEQ ID NO 7
<211> LENGTH: 736
<212> TYPE: PRT
<213> ORGANISM: Artificial Sequence
<220> FEATURE:
<223> OTHER INFORMATION: synthetic construct

<400> SEQUENCE: 7

Met Ser Phe Val Asp His Pro Pro Asp Trp Leu Glu Ser Ile Gly Asp
1               5                   10                  15

Gly Phe Arg Glu Phe Leu Gly Leu Glu Ala Gly Pro Pro Lys Pro Lys
            20                  25                  30

Ala Asn Gln Gln Lys Gln Asp Asn Ala Arg Gly Leu Val Leu Pro Gly
        35                  40                  45

Tyr Lys Tyr Leu Gly Pro Gly Asn Gly Leu Asp Lys Gly Asp Pro Val
    50                  55                  60

Asn Phe Ala Asp Glu Val Ala Arg Glu His Asp Leu Ser Tyr Gln Lys
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Ser Asp Thr Ser Phe Gly Gly Asn
            100                 105                 110

Leu Gly Lys Ala Val Phe Gln Ala Lys Lys Arg Ile Leu Glu Pro Leu
        115                 120                 125

Gly Leu Val Glu Thr Pro Asp Lys Thr Ala Pro Ala Ala Lys Lys Arg
    130                 135                 140

Pro Leu Glu Gln Ser Pro Gln Glu Pro Asp Ser Ser Ser Gly Val Gly
145                 150                 155                 160

Lys Lys Gly Lys Gln Pro Ala Arg Lys Arg Leu Asn Phe Asp Asp Glu
                165                 170                 175

Pro Gly Ala Gly Asp Gly Pro Pro Glu Gly Pro Ser Ser Gly Ala
            180                 185                 190

Met Ser Thr Glu Thr Glu Met Arg Ala Ala Ala Gly Gly Asn Gly Gly
        195                 200                 205

Asp Ala Gly Gln Gly Ala Glu Gly Val Gly Asn Ala Ser Gly Asp Trp
    210                 215                 220

His Cys Asp Ser Thr Trp Ser Glu Ser His Val Thr Thr Thr Ser Thr
225                 230                 235                 240

Arg Thr Trp Val Leu Pro Thr Tyr Asn Asn His Leu Tyr Leu Arg Leu
                245                 250                 255

Gly Ser Ser Asn Ala Ser Asp Thr Phe Asn Gly Phe Ser Thr Pro Trp
            260                 265                 270

Gly Tyr Phe Asp Phe Asn Arg Phe His Cys His Phe Ser Pro Arg Asp
        275                 280                 285

Trp Gln Arg Leu Ile Asn Asn His Trp Gly Leu Arg Pro Lys Ser Met
    290                 295                 300

Gln Val Arg Ile Phe Asn Ile Gln Val Lys Glu Val Thr Thr Ser Asn
305                 310                 315                 320

Gly Glu Thr Thr Val Ser Asn Asn Leu Thr Ser Thr Val Gln Ile Phe
                325                 330                 335

Ala Asp Ser Thr Tyr Glu Leu Pro Tyr Val Met Asp Ala Gly Gln Glu
            340                 345                 350

Gly Ser Leu Pro Pro Phe Pro Asn Asp Val Phe Met Val Pro Gln Tyr
        355                 360                 365

Gly Tyr Cys Gly Leu Val Thr Gly Gly Ser Ser Gln Asn Gln Thr Asp
    370                 375                 380
```

Arg Asn Ala Phe Tyr Cys Leu Glu Tyr Phe Pro Ser Gln Met Leu Arg
385                 390                 395                 400

Thr Gly Asn Asn Phe Glu Met Val Tyr Lys Phe Glu Asn Val Pro Phe
            405                 410                 415

His Ser Met Tyr Ala His Ser Gln Ser Leu Asp Arg Leu Met Asn Pro
        420                 425                 430

Leu Leu Asp Gln Tyr Leu Trp Glu Leu Gln Ser Thr Thr Ser Gly Gly
    435                 440                 445

Thr Leu Asn Gln Gly Asn Ser Ala Thr Asn Phe Ala Lys Leu Thr Lys
450                 455                 460

Thr Asn Phe Ser Gly Tyr Arg Lys Asn Trp Leu Pro Gly Pro Met Met
465                 470                 475                 480

Lys Gln Gln Arg Phe Ser Lys Thr Ala Ser Gln Asn Tyr Lys Ile Pro
                485                 490                 495

Gln Gly Arg Asn Asn Ser Leu Leu His Tyr Glu Thr Arg Thr Thr Leu
            500                 505                 510

Asp Gly Arg Trp Ser Asn Phe Ala Pro Gly Thr Ala Met Ala Thr Ala
        515                 520                 525

Ala Asn Asp Ala Thr Asp Phe Ser Gln Ala Gln Leu Ile Phe Ala Gly
    530                 535                 540

Pro Asn Ile Thr Gly Asn Thr Thr Thr Asp Ala Asn Asn Leu Met Phe
545                 550                 555                 560

Thr Ser Glu Asp Glu Leu Arg Ala Thr Asn Pro Arg Asp Thr Asp Leu
                565                 570                 575

Phe Gly His Leu Ala Thr Asn Gln Gln Asn Ala Thr Thr Val Pro Thr
            580                 585                 590

Val Asp Asp Val Asp Gly Val Gly Val Tyr Pro Gly Met Val Trp Gln
        595                 600                 605

Asp Arg Asp Ile Tyr Tyr Gln Gly Pro Ile Trp Ala Lys Ile Pro His
    610                 615                 620

Thr Asp Gly His Phe His Pro Ser Pro Leu Ile Gly Gly Phe Gly Leu
625                 630                 635                 640

Lys Ser Pro Pro Pro Gln Ile Phe Ile Lys Asn Thr Pro Val Pro Ala
                645                 650                 655

Asn Pro Ala Thr Thr Phe Ser Pro Ala Arg Ile Asn Ser Phe Ile Thr
            660                 665                 670

Gln Tyr Ser Thr Gly Gln Val Ala Val Lys Ile Glu Trp Glu Ile Gln
        675                 680                 685

Lys Glu Arg Ser Lys Arg Trp Asn Pro Glu Val Gln Phe Thr Ser Asn
    690                 695                 700

Tyr Gly Ala Gln Asp Ser Leu Leu Trp Ala Pro Asp Asn Ala Gly Ala
705                 710                 715                 720

Tyr Lys Glu Pro Arg Ala Ile Gly Ser Arg Tyr Leu Thr Asn His Leu
                725                 730                 735

<210> SEQ ID NO 8
<211> LENGTH: 1803
<212> TYPE: DNA
<213> ORGANISM: Artificial Sequence
<220> FEATURE:
<223> OTHER INFORMATION: synthetic construct

<400> SEQUENCE: 8
acggcgcctg cggcaaaaaa gaggcctcta gagcagagtc ctcaagagcc agactcctcg     60
agcggagttg gcaagaaagg caaacagcct gccagaaaga gactcaactt tgacgacgaa    120

```
cctggagccg agacgggcc tcccccagaa ggaccatctt ccggagctat gtctactgag      180
actgaaatgc gtgcagcagc tggcggaaat ggtggcgatg cgggacaagg tgccgaggga      240
gtgggtaatg cctccggtga ttggcattgc gattccactt ggtcagagag ccacgtcacc      300
accacctcaa cccgcacctg gtcctgccg acctacaaca accacctgta cctgcggctc       360
ggctcgagca acgccagcga cacttcaac ggattctcca cccctgggg atactttgac        420 tttaaccgct tccactgcca cttctcgcca agagactggc aaaggctcat caacaaccac      480 tgggactgc gccccaaaag catgcaagtc cgcatcttca acatccaagt taaggaggtc       540
acgacgtcta cgggagac gaccgtatcc aacaacctca ccagcacggt ccagatcttt        600
gcggacagca cgtacgagct cccgtacgtg atggatgcag gtcaggaggg cagcttgcct      660 cctttccca acgacgtgtt catggtgcct cagtacgggt actgcggact ggtaaccgga       720
ggcagctctc aaaaccagac agacagaaat gccttctact gtctggagta ctttcccagc     780
cagatgctga gaaccggaaa caactttgag atggtgtaca agtttgaaaa cgtgcccttc      840
cactccatgt acgctcacag ccagagcctg ataggctga tgaacccgct gctggaccag       900
tacctgtggg agctccagtc taccacctct ggaggaactc tcaaccaggg caattcagcc      960
accaactttg ccaagctgac caaaacaaac ttttctggct accgcaaaaa ctggctcccg      1020
gggcccatga tgaagcagca gagattctcc aagactgcca gtcaaaacta caagattccc      1080
cagggaagaa acaacagtct gctccattat gagaccagaa ctaccctcga cggaagatgg      1140
agcaattttg ccccgggaac ggccatggca accgcagcca acgacgccac cgacttctct      1200
caggcccagc tcatctttgc ggggcccaac atcaccggca caccaccac agatgccaat      1260 aacctgatgt tcacttcaga agatgaactt agggccacca accccgga cactgacctg       1320 tttggccacc tggcaaccaa ccagcaaaac gccaccaccg ttcctaccgt agacgacgtg     1380
gacggagtcg gcgtgtaccc gggaatggtg tggcaggaca gagacattta ctaccaaggg     1440
cccatttggg ccaaaattcc acacacggat ggacactttc acccgtctcc tctcattggc    1500
ggatttggac tgaaaagccc gcctccacaa atattcatca aaaacactcc tgtacccgcc    1560
aatcccgcaa cgaccttctc tccggccaga atcaacagct tcatcaccca gtacagcacc    1620
ggacaggtgg ctgtcaaaat agaatgggaa atccagaagg agcggtccaa gagatggaac   1680
ccagaggtcc agttcacgtc caactacgga gcacaggact cgcttctctg gctcccgac     1740 aacgccggag cctacaaaga gcccagggcc attggatccc gatacctcac caaccacctc   1800
tag                                                                  1803
```

<210> SEQ ID NO 9
<211> LENGTH: 600
<212> TYPE: PRT
<213> ORGANISM: Artificial Sequence
<220> FEATURE:
<223> OTHER INFORMATION: synthetic construct

<400> SEQUENCE: 9

Thr Ala Pro Ala Ala Lys Lys Arg Pro Leu Glu Gln Ser Pro Gln Glu
1               5                   10                  15

Pro Asp Ser Ser Ser Gly Val Gly Lys Lys Gly Lys Gln Pro Ala Arg
            20                  25                  30

Lys Arg Leu Asn Phe Asp Asp Glu Pro Gly Ala Gly Asp Gly Pro Pro
        35                  40                  45

Pro Glu Gly Pro Ser Ser Gly Ala Met Ser Thr Glu Thr Glu Met Arg
    50                  55                  60

```
Ala Ala Ala Gly Gly Asn Gly Gly Asp Ala Gly Gln Gly Ala Glu Gly
 65                  70                  75                  80

Val Gly Asn Ala Ser Gly Asp Trp His Cys Asp Ser Thr Trp Ser Glu
                 85                  90                  95

Ser His Val Thr Thr Thr Ser Thr Arg Thr Trp Val Leu Pro Thr Tyr
            100                 105                 110

Asn Asn His Leu Tyr Leu Arg Leu Gly Ser Ser Asn Ala Ser Asp Thr
            115                 120                 125

Phe Asn Gly Phe Ser Thr Pro Trp Gly Tyr Phe Asp Phe Asn Arg Phe
    130                 135                 140

His Cys His Phe Ser Pro Arg Asp Trp Gln Arg Leu Ile Asn Asn His
145                 150                 155                 160

Trp Gly Leu Arg Pro Lys Ser Met Gln Val Arg Ile Phe Asn Ile Gln
                165                 170                 175

Val Lys Glu Val Thr Thr Ser Asn Gly Glu Thr Thr Val Ser Asn Asn
            180                 185                 190

Leu Thr Ser Thr Val Gln Ile Phe Ala Asp Ser Thr Tyr Glu Leu Pro
            195                 200                 205

Tyr Val Met Asp Ala Gly Gln Glu Gly Ser Leu Pro Pro Phe Pro Asn
    210                 215                 220

Asp Val Phe Met Val Pro Gln Tyr Gly Tyr Cys Gly Leu Val Thr Gly
225                 230                 235                 240

Gly Ser Ser Gln Asn Gln Thr Asp Arg Asn Ala Phe Tyr Cys Leu Glu
                245                 250                 255

Tyr Phe Pro Ser Gln Met Leu Arg Thr Gly Asn Asn Phe Glu Met Val
            260                 265                 270

Tyr Lys Phe Glu Asn Val Pro Phe His Ser Met Tyr Ala His Ser Gln
            275                 280                 285

Ser Leu Asp Arg Leu Met Asn Pro Leu Leu Asp Gln Tyr Leu Trp Glu
    290                 295                 300

Leu Gln Ser Thr Thr Ser Gly Gly Thr Leu Asn Gln Gly Asn Ser Ala
305                 310                 315                 320

Thr Asn Phe Ala Lys Leu Thr Lys Thr Asn Phe Ser Gly Tyr Arg Lys
                325                 330                 335

Asn Trp Leu Pro Gly Pro Met Met Lys Gln Gln Arg Phe Ser Lys Thr
            340                 345                 350

Ala Ser Gln Asn Tyr Lys Ile Pro Gln Gly Arg Asn Asn Ser Leu Leu
            355                 360                 365

His Tyr Glu Thr Arg Thr Thr Leu Asp Gly Arg Trp Ser Asn Phe Ala
    370                 375                 380

Pro Gly Thr Ala Met Ala Thr Ala Ala Asn Asp Ala Thr Asp Phe Ser
385                 390                 395                 400

Gln Ala Gln Leu Ile Phe Ala Gly Pro Asn Ile Thr Gly Asn Thr Thr
                405                 410                 415

Thr Asp Ala Asn Asn Leu Met Phe Thr Ser Glu Asp Glu Leu Arg Ala
            420                 425                 430

Thr Asn Pro Arg Asp Thr Asp Leu Phe Gly His Leu Ala Thr Asn Gln
            435                 440                 445

Gln Asn Ala Thr Thr Val Pro Thr Val Asp Val Asp Gly Val Gly
    450                 455                 460

Val Tyr Pro Gly Met Val Trp Gln Asp Arg Asp Ile Tyr Tyr Gln Gly
465                 470                 475                 480

Pro Ile Trp Ala Lys Ile Pro His Thr Asp Gly His Phe His Pro Ser
```

|  |  |  | 485 |  |  |  | 490 |  |  |  | 495 |  |
|---|---|---|---|---|---|---|---|---|---|---|---|---|

Pro Leu Ile Gly Gly Phe Gly Leu Lys Ser Pro Pro Gln Ile Phe
            500                 505                 510

Ile Lys Asn Thr Pro Val Pro Ala Asn Pro Ala Thr Thr Phe Ser Pro
        515                 520                 525

Ala Arg Ile Asn Ser Phe Ile Thr Gln Tyr Ser Thr Gly Gln Val Ala
    530                 535                 540

Val Lys Ile Glu Trp Glu Ile Gln Lys Glu Arg Ser Lys Arg Trp Asn
545                 550                 555                 560

Pro Glu Val Gln Phe Thr Ser Asn Tyr Gly Ala Gln Asp Ser Leu Leu
                565                 570                 575

Trp Ala Pro Asp Asn Ala Gly Ala Tyr Lys Glu Pro Arg Ala Ile Gly
            580                 585                 590

Ser Arg Tyr Leu Thr Asn His Leu
            595                 600

<210> SEQ ID NO 10
<211> LENGTH: 1617
<212> TYPE: DNA
<213> ORGANISM: Artificial Sequence
<220> FEATURE:
<223> OTHER INFORMATION: synthetic construct

<400> SEQUENCE: 10

```
atgcgtgcag cagctggcgg aaatggtggc gatgcgggac aaggtgccga gggagtgggt      60
aatgcctccg gtgattggca ttgcgattcc acttggtcag agagccacgt caccaccacc     120
tcaacccgca cctgggtcct gccgacctac aacaaccacc tgtacctgcg gctcggctcg     180
agcaacgcca gcgacacctt caacggattc tccaccccct ggggatactt tgactttaac     240
cgcttccact gccacttctc gccaagagac tggcaaaggc tcatcaacaa ccactgggga     300
ctgcgcccca aaagcatgca agtccgcatc ttcaacatcc aagttaagga ggtcacgacg     360
tctaacgggg agacgaccgt atccaacaac ctcaccagca cggtccagat cttttgcggac    420
agcacgtacg agctcccgta cgtgatggat gcaggtcagg agggcagctt gcctcctttc     480
cccaacgacg tgttcatggt gcctcagtac gggtactgcg gactggtaac cggaggcagc     540
tctcaaaacc agacagacag aaatgccttc tactgtctgg agtactttcc cagccagatg     600
ctgagaaccg gaaacaactt tgagatggtg tacaagtttg aaaacgtgcc cttccactcc     660
atgtacgctc acagccagag cctggatagg ctgatgaacc cgctgctgga ccagtacctg     720
tgggagctcc agtctaccac ctctggagga actctcaacc agggcaattc agccaccaac     780
tttgccaagc tgaccaaaac aaacttttct ggctaccgca aaaactgcct cccggggccc     840
atgatgaagc agcagagatt ctccaagact gccagtcaaa actacaagat cccccaggga     900
agaaacaaca gtctgctcca ttatgagacc agaactaccc tcgacggaag atggagcaat     960
tttgccccgg aacggccat ggcaaccgca gccaacgacg ccaccgactt ctctcaggcc    1020
cagctcatct tgcggggcc caacatcacc ggcaacacca ccacagatgc caataacctg    1080
atgttcactt cagaagatga acttaggccc accaaccccc gggacactga cctgtttggc    1140
cacctggcaa ccaaccagca aaacgccacc accgttccta ccgtagacga cgtggacgga    1200
gtcggcgtgt acccgggaat ggtgtggcag gacagagaca tttactacca agggccatt     1260
tgggccaaaa ttccacacac ggatggacac tttcacccgt ctcctctcat tggcggattt    1320
ggactgaaaa gccgcctcc acaaatattc atcaaaaaca ctcctgtacc cgccaatccc    1380
gcaacgacct tctctccggc cagaatcaac agcttcatca cccagtacag caccggacag    1440
```

```
gtggctgtca aaatagaatg ggaaatccag aaggagcggt ccaagagatg gaacccagag      1500
gtccagttca cgtccaacta cggagcacag gactcgcttc tctgggctcc cgacaacgcc      1560
ggagcctaca aagagcccag ggccattgga tcccgatacc tcaccaacca cctctag         1617
```

```
<210> SEQ ID NO 11
<211> LENGTH: 538
<212> TYPE: PRT
<213> ORGANISM: Artificial Sequence
<220> FEATURE:
<223> OTHER INFORMATION: synthetic construct

<400> SEQUENCE: 11
```

```
Met Arg Ala Ala Ala Gly Gly Asn Gly Gly Asp Ala Gly Gln Gly Ala
1               5                   10                  15

Glu Gly Val Gly Asn Ala Ser Gly Asp Trp His Cys Asp Ser Thr Trp
            20                  25                  30

Ser Glu Ser His Val Thr Thr Thr Ser Thr Arg Thr Trp Val Leu Pro
        35                  40                  45

Thr Tyr Asn Asn His Leu Tyr Leu Arg Leu Gly Ser Ser Asn Ala Ser
    50                  55                  60

Asp Thr Phe Asn Gly Phe Ser Thr Pro Trp Gly Tyr Phe Asp Phe Asn
65                  70                  75                  80

Arg Phe His Cys His Phe Ser Pro Arg Asp Trp Gln Arg Leu Ile Asn
                85                  90                  95

Asn His Trp Gly Leu Arg Pro Lys Ser Met Gln Val Arg Ile Phe Asn
            100                 105                 110

Ile Gln Val Lys Glu Val Thr Thr Ser Asn Gly Glu Thr Thr Val Ser
        115                 120                 125

Asn Asn Leu Thr Ser Thr Val Gln Ile Phe Ala Asp Ser Thr Tyr Glu
    130                 135                 140

Leu Pro Tyr Val Met Asp Ala Gly Gln Glu Gly Ser Leu Pro Pro Phe
145                 150                 155                 160

Pro Asn Asp Val Phe Met Val Pro Gln Tyr Gly Tyr Cys Gly Leu Val
                165                 170                 175

Thr Gly Gly Ser Ser Gln Asn Gln Thr Asp Arg Asn Ala Phe Tyr Cys
            180                 185                 190

Leu Glu Tyr Phe Pro Ser Gln Met Leu Arg Thr Gly Asn Asn Phe Glu
        195                 200                 205

Met Val Tyr Lys Phe Glu Asn Val Pro Phe His Ser Met Tyr Ala His
    210                 215                 220

Ser Gln Ser Leu Asp Arg Leu Met Asn Pro Leu Leu Asp Gln Tyr Leu
225                 230                 235                 240

Trp Glu Leu Gln Ser Thr Thr Ser Gly Gly Thr Leu Asn Gln Gly Asn
                245                 250                 255

Ser Ala Thr Asn Phe Ala Lys Leu Thr Lys Thr Asn Phe Ser Gly Tyr
            260                 265                 270

Arg Lys Asn Trp Leu Pro Gly Pro Met Met Lys Gln Gln Arg Phe Ser
        275                 280                 285

Lys Thr Ala Ser Gln Asn Tyr Lys Ile Pro Gln Gly Arg Asn Asn Ser
    290                 295                 300

Leu Leu His Tyr Glu Thr Arg Thr Thr Leu Asp Gly Arg Trp Ser Asn
305                 310                 315                 320

Phe Ala Pro Gly Thr Ala Met Ala Thr Ala Asn Asp Ala Thr Asp
                325                 330                 335
```

Phe Ser Gln Ala Gln Leu Ile Phe Ala Gly Pro Asn Ile Thr Gly Asn
            340                 345                 350

Thr Thr Thr Asp Ala Asn Asn Leu Met Phe Thr Ser Glu Asp Glu Leu
        355                 360                 365

Arg Ala Thr Asn Pro Arg Asp Thr Asp Leu Phe Gly His Leu Ala Thr
370                 375                 380

Asn Gln Gln Asn Ala Thr Thr Val Pro Thr Val Asp Val Asp Gly
385                 390                 395                 400

Val Gly Val Tyr Pro Gly Met Val Trp Gln Asp Arg Asp Ile Tyr Tyr
                405                 410                 415

Gln Gly Pro Ile Trp Ala Lys Ile Pro His Thr Asp Gly His Phe His
                420                 425                 430

Pro Ser Pro Leu Ile Gly Gly Phe Gly Leu Lys Ser Pro Pro Pro Gln
            435                 440                 445

Ile Phe Ile Lys Asn Thr Pro Val Pro Ala Asn Pro Ala Thr Thr Phe
450                 455                 460

Ser Pro Ala Arg Ile Asn Ser Phe Ile Thr Gln Tyr Ser Thr Gly Gln
465                 470                 475                 480

Val Ala Val Lys Ile Glu Trp Glu Ile Gln Lys Glu Arg Ser Lys Arg
                485                 490                 495

Trp Asn Pro Glu Val Gln Phe Thr Ser Asn Tyr Gly Ala Gln Asp Ser
            500                 505                 510

Leu Leu Trp Ala Pro Asp Asn Ala Gly Ala Tyr Lys Glu Pro Arg Ala
            515                 520                 525

Ile Gly Ser Arg Tyr Leu Thr Asn His Leu
            530                 535

<210> SEQ ID NO 12
<211> LENGTH: 150
<212> TYPE: DNA
<213> ORGANISM: Artificial Sequence
<220> FEATURE:
<223> OTHER INFORMATION: synthetic construct

<400> SEQUENCE: 12
gtggcactcc ccccctgtc gcgttcgctc gttcgctggc tcgattgggg gggtggcagc        60
tcaaagagct gccagacgac ggccctctgg gccgtcgccc ccccaatcga gccagcgaac      120
gagcgaacgc gacagggggg ggagtgccac                                       150

<210> SEQ ID NO 13
<211> LENGTH: 20
<212> TYPE: DNA
<213> ORGANISM: Artificial Sequence
<220> FEATURE:
<223> OTHER INFORMATION: synthetic construct

<400> SEQUENCE: 13
ctctagcaag ggggttttgt                                                   20

<210> SEQ ID NO 14
<211> LENGTH: 7
<212> TYPE: DNA
<213> ORGANISM: Artificial Sequence
<220> FEATURE:
<223> OTHER INFORMATION: synthetic construct

<400> SEQUENCE: 14 agtgtgg                                                                  7

```
<210> SEQ ID NO 15
<211> LENGTH: 158
<212> TYPE: DNA
<213> ORGANISM: Artificial Sequence
<220> FEATURE:
<223> OTHER INFORMATION: synthetic construct

<400> SEQUENCE: 15
aggtggtgat gtcattgttg atgtcattat agttgtcacg cgatagttaa tgattaacag      60
tcatgtgatg tgtgttatcc aataggatga aagcgcgcga atgagatctc gcagacttc     120 cggggtataa aagggtgag tgaacgagcc cgccgcca                             158

<210> SEQ ID NO 16
<211> LENGTH: 112
<212> TYPE: DNA
<213> ORGANISM: Artificial Sequence
<220> FEATURE:
<223> OTHER INFORMATION: synthetic construct

<400> SEQUENCE: 16
ggtggattct gggtatattc ccgcctacct gctgccgaag gtccaaccag agcttcagtg      60
ggcgtggact aacctcgaag agtataaatt ggccgccctc aatctggagg ag            112

<210> SEQ ID NO 17
<211> LENGTH: 169
<212> TYPE: DNA
<213> ORGANISM: Artificial Sequence
<220> FEATURE:
<223> OTHER INFORMATION: synthetic construct

<400> SEQUENCE: 17
agtcaaagac tttttttgctt gggcaaaggt caaccaggtg ccggtgactc acgagttat      60 ggttcccaag aaagtggcgg gaactgagag ggcggagact tctagaaaac gcccactgga    120
tgacgtcacc aataccaact ataaaagtcc ggagaagcgg gcccggctc                169

<210> SEQ ID NO 18
<211> LENGTH: 8
<212> TYPE: PRT
<213> ORGANISM: Artificial Sequence
<220> FEATURE:
<223> OTHER INFORMATION: synthetic construct

<400> SEQUENCE: 18

Gly Ser Ser Asn Ala Ser Asp Thr
1               5

<210> SEQ ID NO 19
<211> LENGTH: 14
<212> TYPE: PRT
<213> ORGANISM: Artificial Sequence
<220> FEATURE:
<223> OTHER INFORMATION: synthetic construct

<400> SEQUENCE: 19

Thr Thr Ser Gly Gly Thr Leu Asn Gln Gly Asn Ser Ala Thr
1               5                   10

<210> SEQ ID NO 20
<211> LENGTH: 6
<212> TYPE: PRT
<213> ORGANISM: Artificial Sequence
<220> FEATURE:
<223> OTHER INFORMATION: synthetic construct

<400> SEQUENCE: 20
```

```
Asn Gly Arg Ala His Ala
1               5

<210> SEQ ID NO 21
<211> LENGTH: 7
<212> TYPE: PRT
<213> ORGANISM: Artificial Sequence
<220> FEATURE:
<223> OTHER INFORMATION: synthetic construct

<400> SEQUENCE: 21

Ser Ile Gly Tyr Pro Leu Pro
1               5

<210> SEQ ID NO 22
<211> LENGTH: 10
<212> TYPE: PRT
<213> ORGANISM: Artificial Sequence
<220> FEATURE:
<223> OTHER INFORMATION: synthetic construct

<400> SEQUENCE: 22

Lys Phe Asn Lys Pro Phe Val Phe Leu Ile
1               5                   10

<210> SEQ ID NO 23
<211> LENGTH: 22
<212> TYPE: PRT
<213> ORGANISM: Artificial Sequence
<220> FEATURE:
<223> OTHER INFORMATION: synthetic construct

<400> SEQUENCE: 23

Asn Ile Ser Leu Asp Asn Pro Leu Glu Asn Pro Ser Ser Leu Phe Asp
1               5                   10                  15

Leu Val Ala Arg Ile Lys
            20

<210> SEQ ID NO 24
<211> LENGTH: 21
<212> TYPE: DNA
<213> ORGANISM: Artificial Sequence
<220> FEATURE:
<223> OTHER INFORMATION: synthetic construct

<400> SEQUENCE: 24
gttcgctcgt tcgctggctc g                                          21

<210> SEQ ID NO 25
<211> LENGTH: 21
<212> TYPE: DNA
<213> ORGANISM: Artificial Sequence
<220> FEATURE:
<223> OTHER INFORMATION: synthetic construct

<400> SEQUENCE: 25
cgagccagcg aacgagcgaa c                                          21
```